(12) United States Patent
Carroll et al.

(10) Patent No.: US 7,276,377 B2
(45) Date of Patent: Oct. 2, 2007

(54) METHOD AND APPARATUS FOR DETERMINING ANTICOAGULANT THERAPY FACTORS

(75) Inventors: Wallace E. Carroll, Santa Barbara, CA (US); R. David Jackson, Rio Ranchero, NM (US)

(73) Assignee: Wada, Inc., Santa Barbara, CA (US)

( * ) Notice: Subject to any disclaimer, the term of this patent is extended or adjusted under 35 U.S.C. 154(b) by 0 days.

(21) Appl. No.: 11/359,667

(22) Filed: Feb. 22, 2006

(65) Prior Publication Data

US 2006/0149483 A1 Jul. 6, 2006

Related U.S. Application Data

(63) Continuation-in-part of application No. 10/662,043, filed on Sep. 12, 2003, now abandoned, which is a continuation-in-part of application No. 10/428,708, filed on May 2, 2003, now abandoned.

(60) Provisional application No. 60/679,423, filed on May 10, 2005.

(51) Int. Cl.
*G01N 33/86* (2006.01)

(52) U.S. Cl. .................. 436/69; 436/149; 436/150; 436/164; 422/73; 422/82.01; 422/82.05; 422/82.09; 73/64.41; 73/64.43; 600/369

(58) Field of Classification Search .................. 436/69, 436/149, 150, 164; 422/68.1, 73, 82.01, 422/82.05, 82.09; 73/64.41, 64.43; 600/369
See application file for complete search history.

(56) References Cited

U.S. PATENT DOCUMENTS

| | | | |
|---|---|---|---|
| 3,905,769 A * | 9/1975 | Carroll et al. ................ 436/69 |
| 4,217,107 A * | 8/1980 | Saito et al. ................... 436/69 |
| 4,252,536 A * | 2/1981 | Kishimoto et al. ........... 356/36 |
| 4,720,787 A * | 1/1988 | Lipscomb ................... 600/369 |
| 5,197,017 A * | 3/1993 | Carroll et al. ................ 702/19 |
| 5,502,651 A * | 3/1996 | Jackson et al. ............. 702/108 |
| 5,981,285 A * | 11/1999 | Carroll et al. ................ 436/69 |
| 6,706,536 B1* | 3/2004 | Carroll et al. .............. 436/164 |

* cited by examiner

*Primary Examiner*—Maureen M. Wallenhorst
(74) *Attorney, Agent, or Firm*—John F. A. Earley, III; Frank J. Bonini, Jr.; Harding, Earley, Follmer & Frailey

(57) ABSTRACT

Methods and apparatus are disclosed for determining a new anticoagulant therapy factor (nATF) for monitoring oral anticoagulant therapy to help prevent excessive bleeding or deleterious blood clots that might otherwise occur before, during or after surgery. In one embodiment, the new anticoagulant therapy factor is based upon a determination of a new fibrinogen transformation rate (nFTR) which, in turn, is dependent on a maximum acceleration point (MAP) for fibrinogen (FBG) conversion. The new anticoagulant therapy factor quantity is also based upon the time to maximum acceleration from the time of reagent injection (TX) into a plasma sample, but does not require the difficulty of obtaining prior art International Normalized Ratio (INR) and International Sensitivity Index (ISI) parameters. Other embodiments provide methods and apparatus for determining an anticoagulant therapy factor without requiring use of a mean normal prothrombin time determination or ISI.

45 Claims, 5 Drawing Sheets

METHOD AND APPARATUS FOR DETERMINING ANTICOAGULANT THERAPY FACTORS

CROSS-REFERENCE TO RELATED APPLICATIONS

This application is a continuation-in-part of U.S. application Ser. No. 10/662,043, filed on Sep. 12, 2003 now abandoned, which is a continuation of U.S. application Ser. No. 10/428,708 filed on May 2, 2003 now abandoned; the application also claims priority to U.S. Provisional application Ser. No. 60/679,423, filed on May 10, 2005, the disclosures of which are herein incorporated by reference.

BACKGROUND OF THE INVENTION

1. Field of the Invention

This invention relates to analyzing blood for carrying out coagulation studies and other chemistry procedures, including monitoring oral anticoagulant therapy to take into account the platelet count in determining prothrombin times (PT), and a new Anticoagulant Therapy Factor (nATF).

2. Description of the Prior Art

Testing of blood and other body fluids is commonly done in hospitals, labs, clinics and other medical facilities. For example, to prevent excessive bleeding or deleterious blood clots, a patient may receive oral anticoagulant therapy before, during and after surgery. Oral anticoagulant therapy generally involves the use of oral anticoagulants—a class of drugs which inhibit blood clotting. To assure that the oral anticoagulant therapy is properly administered, strict monitoring is accomplished and is more fully described in various medical technical literature, such as the articles entitled "PTs, PR, ISIs and INRs: A Primer on Prothrombin Time Reporting Parts I and II" respectively published November, 1993 and December, 1993 issues of *Clinical Hemostasis Review*, and herein incorporated by reference.

These technical articles disclose anticoagulant therapy monitoring that takes into account three parameters which are: International Normalized Ratio (INR), International Sensitivity Index (ISI) and prothrombin time (PT), reported in seconds. The prothrombin time (PT) indicates the level of prothrombin and blood factors V, VII, and X in a plasma sample and is a measure of the coagulation response of a patient. Also affecting this response may be plasma coagulation inhibitors, such as, for example, protein C and protein S. Some individuals have deficiencies of protein C and protein S. The INR and ISI parameters are needed so as to take into account various differences in instrumentation, methodologies and in thromboplastins' (Tps) sensitivities used in anticoagulant therapy. In general, thromboplastins (Tps) used in North America are derived from rabbit brain, those previously used in Great Britain from human brain, and those used in Europe from either rabbit brain or bovine brain. The INR and ISI parameters take into account all of these various factors, such as the differences in thromboplastins (Tps), to provide a standardized system for monitoring oral anticoagulant therapy to reduce serious problems related to prior, during and after surgery, such as excessive bleeding or the formation of blood clots.

The ISI itself according to the WHO 1999 guidelines, Publication no. 889-1999, have coefficients of variation ranging from 1.7% to 8.1%. Therefore, if the ISI is used exponentially to determine the INR of a patient, then the coefficients of variation for the INR's must be even greater than those for the ISI range.

As reported in Part I (Calibration of Thromboplastin Reagents and Principles of Prothrombin Time Report) of the above technical article of the *Clinical Hemostasis Review*, the determination of the INR and ISI parameters are quite involved, and as reported in Part II (Limitation of INR Reporting) of the above technical article of the *Clinical Hemostasis Review*, the error yielded by the INR and ISI parameters is quite high, such as about up to 10%. The complexity of the interrelationship between the International Normalized Ratio (INR), the International Sensitivity Index (ISI) and the patient's prothrombin time (PT) may be given by the below expression (A), wherein the quantity $$\left[ \frac{\text{Patient's } PT}{\text{Mean of } PT \text{ Normal Range}} \right] \quad (A)$$

is commonly referred to as prothrombin ratio (PR):

$$INR = \left[ \frac{\text{Patient's } PT}{\text{Mean of } PT \text{ Normal Range}} \right]^{ISI} \quad (B)$$

The possible error involved with the use of International Normalized Ratio (INR) is also discussed in the technical article entitled "Reliability and Clinical Impact of the Normalization of the Prothrombin Times in Oral Anticoagulant Control" of E. A. Loeliger et al., published in *Thrombosis and Hemostasis* 1985; 53: 148-154, and herein incorporated by reference. As can be seen in the above expression (B), ISI is an exponent of INR which leads to the possible error involved in the use of INR to be about 10% or possibly even more. A procedure related to the calibration of the ISI is described in a technical article entitled "Failure of the International Normalized Ratio to Generate Consistent Results within a Local Medical Community" of V. L. Ng et al., published in Am. J. Clin. Pathol. 1993; 99: 689-694, and herein incorporated by reference.

The unwanted INR deviations are further discussed in the technical article entitled "Minimum Lyophilized Plasma Requirement for ISI Calibration" of L. Poller et al. published in *Am. J. Clin. Pathol.* February 1998, Vol. 109, No. 2, 196-204, and herein incorporated by reference. As discussed in this article, the INR deviations became prominent when the number of abnormal samples being tested therein was reduced to fewer than 20 which leads to keeping the population of the samples to at least 20. The paper of L. Poller et al. also discusses the usage of 20 high lyophilized INR plasmas and 7 normal lyophilized plasmas to calibrate the INR. Further, in this article, a deviation of +/−10% from means was discussed as being an acceptable limit of INR deviation. Further still, this article discusses the evaluation techniques of taking into account the prothrombin ratio (PR) and the mean normal prothrombin time (MNPT), i.e., the geometric mean of normal plasma samples.

The discrepancies related to the use of the INR are further studied and described in the technical article of V. L. NG et al. entitled, "Highly Sensitive Thromboplastins Do Not Improve INR Precision," published in *Am. J. Clin. Pathol.*, 1998; 109, No. 3, 338-346 and herein incorporated by reference. In this article, the clinical significance of INR discordance is examined with the results being tabulated in Table 4 therein and which are analyzed to conclude that the level of discordance for paired values of individual specimens tested with different thromboplastins disadvantageously range from 17% to 29%.

U.S. Pat. No. 5,981,285 issued on Nov. 9, 1999 to Wallace E. Carroll et al., which discloses a "Method and Apparatus for Determining Anticoagulant Therapy Factors" provides an accurate method for taking into account varying prothrombin times (PT) caused by different sensitivities of various thromboplastin formed from rabbit brain, bovine brain or other sources used for anticoagulant therapy. This method does not suffer from the relatively high (10%) error sometimes occurring because of the use of the INR and ISI parameters with the exponents used in their determination.

The lack of existing methods to provide reliable results for physicians to utilize in treatment of patients has been discussed, including in a paper by Davis, Kent D., Danielson, Constance F. M., May, Lawrence S., and Han, Zi-Qin, "Use of Different Thromboplastin Reagents Causes Greater Variability in International Normalized Ratio Results Than Prolonged Room Temperature Storage of Specimens," *Archives of Pathol. and Lab. Medicine*, November 1998. The authors observed that a change in the thromboplastin reagent can result in statistically and clinically significant differences in the INR.

Considering the current methods for determining anticoagulant therapy factors, there are numerous opportunities for error. For example, it has been reported that patient deaths have occurred at St. Agnes Hospital in Philadelphia, Pa. There the problem did not appear to be the thromboplastin reagent, but rather, was apparently due to a failure to enter the correct ISI in the instrument used to carry out the prothrombin times when the reagent was changed. This resulted in the incorrect INR's being reported. Doses of coumadin were given to already overanticoagulated patients based on the faulty INR error, and it is apparent that patient deaths were caused by excessive bleeding due to coumadin overdoses.

But even in addition to errors where a value is not input correctly, the known methods for determining anticoagulant therapy factors still may be prone to errors, even when the procedure is carried out in accordance with the reagent manufacturer's ISI data. One can see this in that current methods have reported that reagents used to calculate prothrombin times, may, for healthy (i.e., presumed normal) subjects, give rise to results ranging from 9.7 to 12.3 seconds at the 95th % reference interval for a particular reagent, and 10.6 to 12.4 for another. The wide ranges for normal patients illustrates the mean normal prothrombin time differences. When the manufacturer reference data ranges are considered, if indeed 20 presumed normal patients' data may be reported within a broad range, then there is the potential for introduction of this range into the current anticoagulation therapy factor determinations, since they rely on the data for 20 presumed normal patients. Considering the reagent manufacturer expected ranges for expected normal prothrombin times, INR units may vary up to 30%. This error is apparently what physicians must work with when treating patients. A way to remove the potential for this type of error is needed.

This invention relates to the inventions disclosed in U.S. Pat. No. 3,905,769 ('769) of Sep. 16, 1975; U.S. Pat. No. 5,197,017 ('017) dated Mar. 23, 1993; and U.S. Pat. No. 5,502,651 ('651) dated Mar. 26, 1996, all issued to Wallace E. Carroll and R. David Jackson, and all of which are incorporated herein by reference. The present invention provides apparatus and methods for monitoring anticoagulant therapy.

SUMMARY OF THE INVENTION

Methods and apparatus useful for processing coagulation studies, and other chemistry procedures involving blood and blood components. The apparatus and methods may be used to determine anticoagulant therapy factors which are designated herein, in particular, to determine new Anticoagulant Therapy Factors (nATF's) which preferably may replace International Normalized Ratio (INR) in anticoagulation therapy management. Previously, anticoagulation therapy involved the use of International Normalized Ratios (INR's). The International Normalized Ratio (INR) was utilized in order to arrive at an anticoagulant therapy factor (ATF). The INR based ATF was dependent on the prothrombin time (PT), the prothrombin ratio (PR), a fibrinogen transformation rate (FTR), and a maximum acceleration point (MAP) having an associated time to maximum acceleration (TMA).

Methods and apparatus are disclosed for determining a new anticoagulant therapy factor (nATF) for monitoring oral anticoagulant therapy to help prevent excessive bleeding or deleterious blood clots that might otherwise occur before, during or after surgery. In one embodiment, a new anticoagulant therapy factor (nATF) is based upon a determination of the fibrinogen transformation rate (FTR) which, in turn, is dependent on a maximum acceleration point (MAP) for fibrinogen (FBG) conversion. The nATF quantity is also based upon the time to maximum acceleration from the time of reagent injection (TX) into a plasma sample, but does not require the difficulty of obtaining prior art International Normalized Ratio (INR) and International Sensitivity Index (ISI) parameters. The International Normalized Ratio (INR) was created to relate all species' clotting material to human clotting material, and nATF can replace INR in anticoagulant therapy management.

In accordance with other embodiments, methods and apparatus are provided for determining an anticoagulation therapy factor, which do not require the use of a mean normal prothrombin time (MNPT) and ISI data. In other words, the need to obtain and calculate the prothrombin time of 20 presumed normal patients, is not required to determine an anticoagulant therapy factor.

In accordance with the present invention, there is provided apparatus and methods for carrying out coagulation studies and other chemical procedures and analyses.

DETAILED DESCRIPTION

Figure 1:
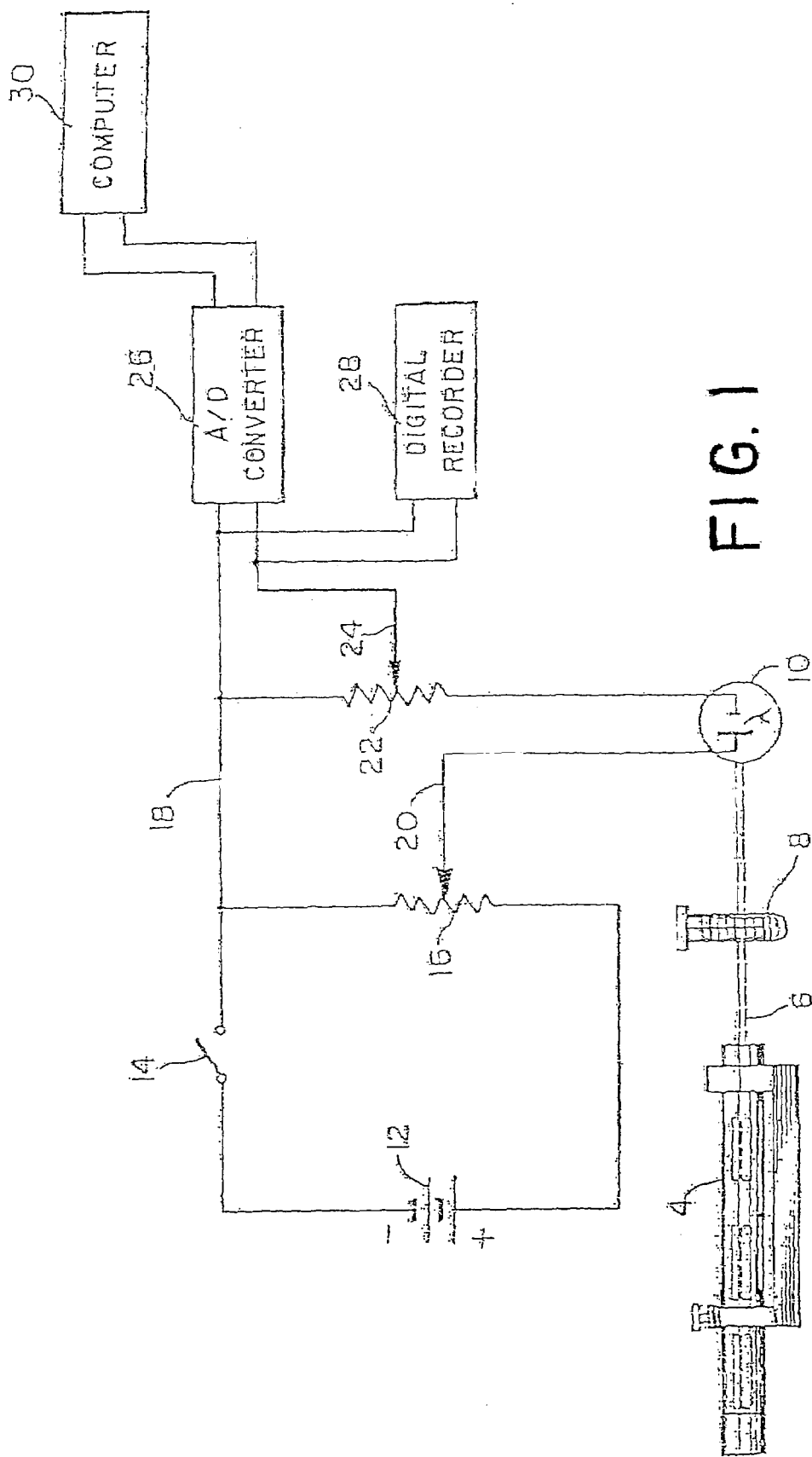
FIG. 1 is a diagram of potentiophotometric apparatus constructed in accordance with one embodiment of the present invention for determining blood chemistry analyses such as coagulation studies, including determination of the new anticoagulant therapy factor (nATF), where the output of the analog/digital (A/D) converter is applied to a computer.

Referring to the drawings, wherein the same reference numbers indicate the same elements throughout, there is shown in FIG. 1 a light source 4 which may be a low power gas laser, or other light producing device, producing a beam of light 6 which passes through a sample test tube, such as the container 8, and is received by detection means which is preferably a silicon or selenium generating photocell 10 (photovoltaic cell). Battery 12 acts as a constant voltage DC source. Its negative terminal is connected through switch 14 to one end of variable resistor 16 and its positive terminal is connected directly to the opposite end of variable resistor 16. The combination of battery 12 and variable resistor 16 provides a variable DC voltage source, the variable voltage being derivable between line 18 at the upper terminal of resistor 16 and wiper 20. This variable DC voltage source is connected in series with detection means photocell 10, the positive output of detection means photocell 10 being connected to the wiper 20 of variable resistor 16 so that the voltage produced by the variable voltage DC source opposes the voltage produced by the detection means photocell 10. The negative output of detection means photocell 10 is connected through variable resistor 22 to line 18. Thus, the voltage across variable resistor 22 is the difference between the voltage produced by the variable voltage DC source and the voltage produced by the photovoltaic cell 10. The output of the electrical network is taken between line 18 and wiper 24 of variable resistor 22. Thus, variable resistor 22 acts as a multiplier, multiplying the voltage produced as a result of the aforesaid subtraction by a selective variable depending on the setting of variable resistor 22. The potentiophotometer just described embodies the electrical-analog solution to Beer's Law and its output is expressed directly in the concentration of the substance being measured.

Wiper 24 is illustrated placed at a position to give a suitable output and is not varied during the running of the test. The output between line 18 and wiper 24 is delivered to an A/D converter 26 and digital recorder 28. As is known, the A/D converter 26 and the digital recorder 28 may be combined into one piece of equipment and may, for example, be a device sold commercially by National Instrument of Austin, Tex. as their type Lab-PC+. The signal across variable resistor 22 is an analog signal and hence the portion of the signal between leads 18 and wiper 24, which is applied to the A/D converter 26 and digital recorder 28, is also analog. A computer 30 is connected to the output of the A/D converter 26, is preferably IBM compatible, and is programmed in a manner described hereinafter.

For example, preferably, the detector cell 10 is positioned adjacent an opposite wall of the sample container 8, and the emitter light source 4 positioned adjacent on opposite wall, so the light 6 emitted from the light source 4 passes through the container 8. The light source 4 is preferably selected to produce light 6 which can be absorbed by one or more components which are to be measured.

The apparatus can be used to carry out coagulation studies in accordance with the invention. In accordance with a preferred embodiment of the present invention, the light source 4 may, for example, comprise a light emitting diode (LED) emitting a predetermined wavelength, such as for example, a wavelength of 660 nm, and the detector cell 10 may, for example, comprise a silicon photovoltaic cell detector. Optionally, though not shown, a bar code reader may also be provided to read bar code labels placed on the sample container 8. The bar code reader may produce a signal which can be read by the computer 30 to associate a set of data with a particular sample container 8.

To carry out a coagulation study on blood plasma, the citrated blood is separated from the red blood cell component of the blood. Conventional methods of separation, which include centrifugation, may be employed. Also, the use of a container device such as that disclosed in our issued U.S. Pat. No. 6,706,536, may also be used, and the method disclosed therein for reading the plasma volume relative to the sample volume may also be employed.

Illustrative of an apparatus and method according to one embodiment is a coagulation study which can be carried out therewith. A reagent, such as, for example, Thromboplastin-Calcium (Tp-Ca), is added to the plasma sample which is maintained at about 37° C. by any suitable temperature control device, such as a heated sleeve or compartment (not shown). The reagent addition is done by dispensing an appropriate amount of the reagent into the plasma portion of the blood. The plasma portion may be obtained by any suitable separation technique, such as for example, centrifugation. In one embodiment illustrated herein, the container 8 is vented when reagent is added. The reagent for example, may comprise thromboplastin, which is added in an amount equal to twice the volume of the plasma. The reagent is mixed with the plasma. It is preferable to minimize air bubbles so as not to interfere with the results. The plasma sample to which the reagent has been added is heated to maintain a 37° C. temperature, which, for example, may be done by placing the container holding the plasma and reagent in a heating chamber (not shown).

Readings are taken of the optical activity of the components in the sample container 8.

Reaction kinematics may be studied by observing changes in the optical density of the plasma layer. For example, an amount of reagent, such as Thromboplastin-Calcium (Tp-Ca), may be added to the plasma sample in the container. The plasma sample in the container may comprise a known amount of volume. Alternately, the plasma volume may be ascertained through the method and apparatus described in our U.S. Pat. No. 6,706,536. A controlled amount of Tp-Ca reagent is added to the plasma sample. The amount of reagent added corresponds to the amount of plasma volume. The detector cell 10 and emitter light source 4 are preferably positioned so the absorbance of the plasma sample may be read, including when the reagent is added and the sample volume is thereby increased.

Figure 2:
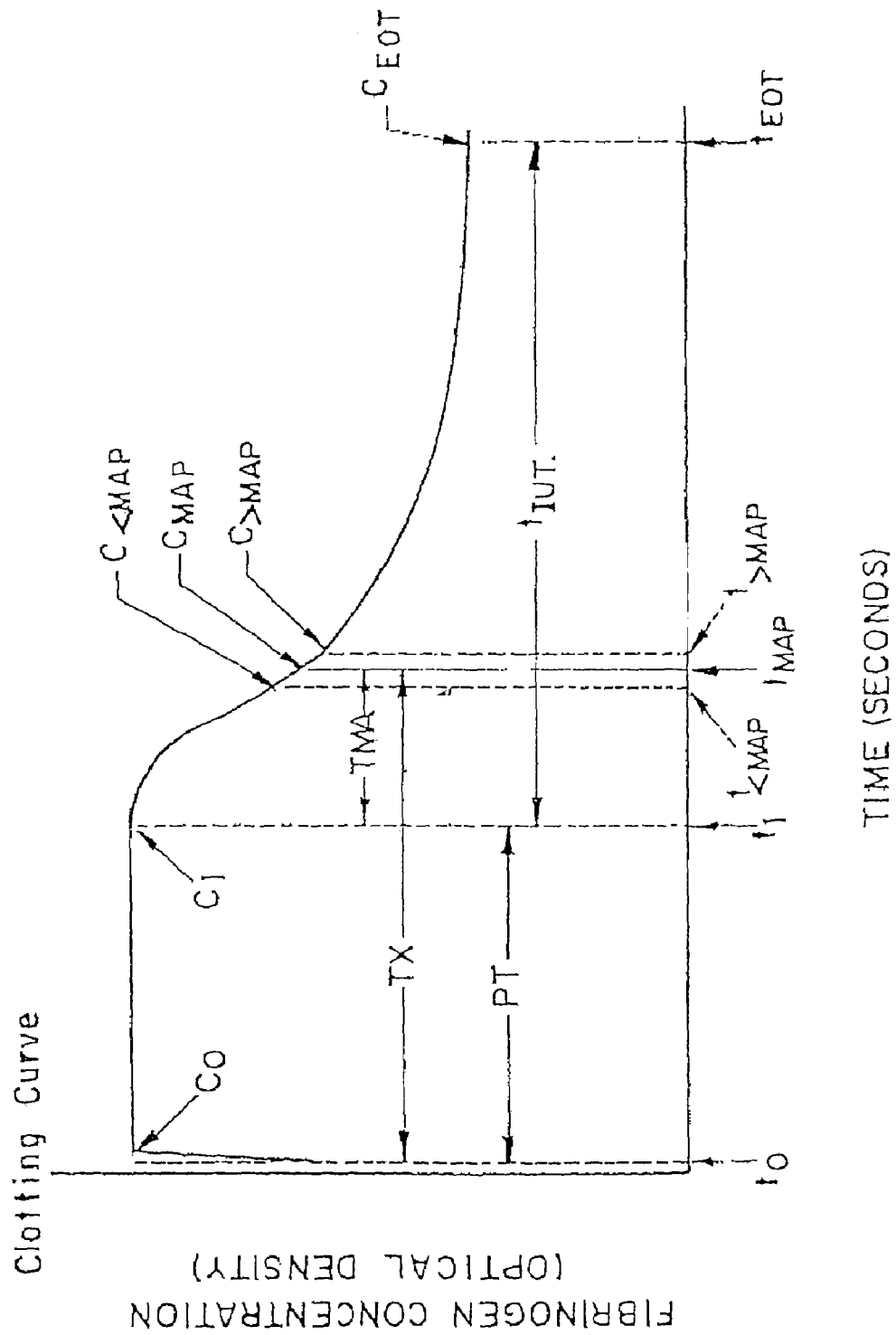
FIG. 2 is a plot of the various phases of the fibrinogen concentration occurring in a typical plasma clotting process.

With the detection elements, such as the cell 10 and emitter 4, positioned to read the plasma sample and the reagents added thereto, the reaction analysis of the extended prothrombin time curve can be followed. FIG. 2 shows a graph of a plot of the various phases of the fibrinogen concentration occurring in a typical plasma clotting process. The change in optical density of the plasma level occurs after reagents have been added. The optical density of the plasma sample is monitored, as optically clear fibrinogen converts to turbid fibrin.

The coagulation study of the type described above is used to ascertain the results shown in the graph plotted on FIG. 2. The description of the analysis makes reference to terms, and symbols thereof, having a general description as used herein, all to be further described and all of which are given in Table 1.

TABLE 1

| SYMBOL | TERM | GENERAL DESCRIPTION |
|---|---|---|
| PT | Prothrombin Time | A period of time calculated from the addition of the reagent (e.g., thromboplastin-calcium) to a point where the conversion of fibrinogen to fibrin begins (i.e. the formation of the first clot). |
| TMA | Time to Maximum Acceleration | The time from PT to a point where the rate of conversion of fibrinogen to fibrin has reached maximum and begins to slow. |
| MAP | Maximum Acceleration Point | A point where the fibrinogen conversion achieves maximum acceleration and begins to decelerate. |
| EOT | End of Test | Point where there is no appreciable change in the polymerization of fibrin. |
| TEOT | Theoretical End Of Test | The time to convert all fibrinogen based on the time to convert the fibrinogen during the simulated Zero Order Kinetic rate. |
| TX (or $T_2$) | Time to Map | Time to reach the Maximum Acceleration Point (MAP) from point of injection. |
| MNTX | Mean Normal Time to Map | The mean of the times of at least 20 normal people to reach then Maximum Acceleration Point (MAP). |
| FTR | Fibrinogen Transformation Ratio | The amount of fibrinogen converted during a particular time period. This is a percentage of the total Fibrinogen. |
| ATF | Anticoagulation Therapy Factor | The calculated value used to monitor the uses of an anticoagulant without a need for an International Sensitivity Index (ISI) of a thromboplastin. |
| nATF | new Anticoagulation Therapy Factor | A replacement for the INR to provide a standardized system for monitoring oral anticoagulant therapy. (Also expressed as ATFt and ATFz) |
| PR | Prothrombin Ratio | A value computed by dividing a sample PT by the geometric mean of at least 20 normal people (MNPT). |
| INR | International Normalized Ratio | A parameter which takes into account the various factors involved in anticoagulation therapy monitoring to provide a standardized system for monitoring oral anticoagulant therapy. |
| ATFt | Anticoagulation Therapy Factor Theoretical | Utilizing a calculated Theoretical End Of Test value and the Natural Log "e" to removed the need for an MNPT. |
| XR | Time to MAP Ratio | The value computed by dividing a sample "TX" by the geometric mean of at least 20 normal people "MNTX". |

Prior patents for obtaining an anticoagulant therapy factor (ATF) relied on the International Normalized Ratio (INR) system which was derived in order to improve the consistency of results from one laboratory to another. The INR system utilized the calculation of INR from the equation:

$$INR = (PT_{patient}/PT_{geometric\ mean})^{ISI}$$

wherein the $PT_{patient}$ is the prothrombin time (PT) as an absolute value in seconds for a patient, $PT_{geometric\ mean}$ is the mean, a presumed number of normal patients. The International Sensitivity Index (ISI) is an equalizing number which a reagent manufacturer of thromboplastin specifies. The ISI is a value which is obtained through calibration against a World Health Organization primary reference thromboplastin standard. Local ISI (LSI) values have also been used to provide a further refinement of the manufacturer-assigned ISI of the referenced thromboplastin in order to provide local calibration of the ISI value.

For illustration, the present invention can be employed for accurate determination of a new Anticoagulant Therapy Factor (nATF) from a human blood sample, for use during the monitoring of oral anticoagulant therapy, without the need for an ISI or LSI value, and without the need for an INR value. As is known in the art, blood clotting Factors I, II, V, VII, VIII, IX and X are associated with platelets (Bounameaux, 1957); and, among these, Factors II, VII, IX and X are less firmly attached, since they are readily removed from the platelets by washing (Betterle, Fabris et al, 1977). The role of these platelet-involved clotting factors in blood coagulation is not, however, defined. The present invention provides a method and apparatus for a new Anticoagulant Therapy Factor (nATF) which may be used for anticoagulant therapy monitoring without the need for INR.

The International Normalized Ratio (INR) is previously discussed in already incorporated reference technical articles entitled "PTs, PRs, ISIs and INRs: A Primer on Prothrombin Time Reporting Part I and II respectively," published in November, 1993 and December, 1993 issues of *Clinical Hemostasis Review*. The illustrative example of an analysis which is carried out employing the present invention relies upon the maximum acceleration point (MAP) at which fibrinogen conversion achieves a maximum and from there decelerates, the time to reach the MAP (TX), and the mean normal time to MAP (MNTX), and a fibrinogen transformation rate (FTR), that is, the thrombin activity in which fibrinogen (FBG) is converted to fibrin to cause clotting in blood plasma.

More particularly, during the clotting steps used to determine the clotting process of a plasma specimen of a patient under observation, a thromboplastin (Tp) activates factor VII which, activates factor X, which, in turn, under catalytic action of factor V, activates factor II (sometimes referred to as prothrombin) to cause factor IIa (sometimes referred to as thrombin) that converts fibrinogen (FBG) to fibrin with resultant turbidity activity which is measured, in a manner as to be described hereinafter, when the reaction is undergoing simulated zero-order kinetics.

From the above, it should be noted that the thromboplastin (Tp) does not take part in the reaction where factor IIa (thrombin) converts fibrinogen (FBG) to fibrin which is deterministic of the clotting of the plasma of the patient under consideration. The thromboplastin (Tp) only acts to activate factor VII to start the whole cascade rolling. Note also that differing thromboplastins (Tps) have differing rates of effect on factor VII, so the rates of enzyme factor reactions up to II-IIa (the PT) will vary.

Therefore, the prothrombin times (PTs) vary with the different thromboplastins (Tps) which may have been a factor that mislead authorities to the need of taking into account the International Normalized Ratio (INR) and the International Sensitivity Index (ISI) to compensate for the use of different types of thromboplastins (Tps) during the monitoring of oral anticoagulant therapy. It is further noted, that thromboplastins (Tps) have nothing directly to do with factor IIa converting fibrinogen (FBG) to fibrin, so it does not matter which thromboplastin is used when the fibrinogen transformation is a primary factor.

The thromboplastin (Tp) is needed therefore only to start the reactions that give factor IIa. Once the factor IIa is obtained, fibrinogen (FBG) to fibrin conversion goes on its own independent of the thromboplastin (Tp) used.

In one embodiment, the present method and apparatus has use, for example, in coagulation studies where fibrinogen (FBG) standard solutions and a control solution are employed, wherein the fibrinogen standard solutions act as dormant references to which solutions analyzed with the present invention are compared, whereas the control solution acts as a reagent that is used to control a reaction. The fibrinogen standards include both high and low solutions, whereas the control solution is particularly used to control clotting times and fibrinogens of blood samples. It is only necessary to use fibrinogen standards when PT-derived fibrinogens (FBG's) are determined. In connection with other embodiments of the invention, fibrinogen (FBG) standards are not necessary for the INR determination (such as for example INRz described herein).

Another embodiment provides a method and apparatus for determining an anticoagulation therapy factor which does not require the use of fibrinogen standard solutions. In this embodiment, the apparatus and method may be carried out without the need to ascertain the mean normal prothrombin time (MNPT) of 20 presumed normal patients.

Where a fibrinogen standard solution is utilized, a fibrinogen (FBG) solution of about 10 g/l may be prepared from a cryoprecipitate. The cryoprecipitate may be prepared by freezing plasma, letting the plasma thaw in a refrigerator and then, as known in the art, expressing off the plasma so as to leave behind the residue cryoprecipitate. The gathered cryoprecipitate should contain a substantial amount of both desired fibrinogen (FBG) and factor VIII (antihemophilic globulin), along with other elements that are not of particular concern to the present invention. The 10 g/l fibrinogen (FBG) solution, after further treatment, serves as the source for the high fibrinogen (FBG) standard. A 0.5 g/l fibrinogen (FBG) solution may then be prepared by a 1:20 (10 g/l/20=0.5 g/l) dilution of some of the gathered cryoprecipitate to which may be added an Owren's Veronal Buffer (pH 7.35) (known in the art) or normal saline solution and which, after further treatment, may serve as a source of the low fibrinogen (FBG) standard.

The fibrinogen standard can be created by adding fibrinogen to normal plasma in an empty container. Preferably, the fibrinogen standard is formed from a 1:1 fibrinogen to normal plasma solution. For example, 0.5 ml of fibrinogen and 0.5 ml of plasma can be added together in an empty container. Thromboplastin calcium is then added to the fibrinogen standard. Preferably, twice the amount by volume of thromboplastin is added into the container per volume amount of fibrinogen standard which is present in the container. The reaction is watched with the apparatus 10.

Then, 1 ml of each of the high (10 g/l) and low (0.5 g/l) sources of the fibrinogen standards may be added to 1 ml of normal human plasma (so the cryoprecipate plasma solution can clot). Through analysis, high and low fibrinogen (FBG) standards are obtained. Preferably, a chemical method to determine fibrinogen (FBG) is used, such as, the Ware method to clot, collect and wash the fibrin clot and the Ratnoff method to dissolve the clot and measure the fibrinogen (FBG) by its tyrosine content. The Ware method is used to obtain the clot and generally involves collecting blood using citrate, oxalate or disodium ethylenediaminetetraacetate as anticoagulant, typically adding 1.0 ml to about 30 ml 0.85% or 0.90% sodium chloride (NaCl) in a flask containing 1 ml M/5 phosphate buffer and 0.5 ml 1% calcium chloride $CaCl_2$, and then adding 0.2 ml (100 units) of a thrombin solution. Preferably, the solution is mixed and allowed to stand at room temperature for fifteen minutes, the fibrin forming in less than one minute forming a solid gel if the fibrinogen concentration is normal. A glass rod may be introduced into the solution and the clot wound around the rod. See Richard J. Henry, M. D., et al., Clinical Chemistry: Principals and Techniques ($2^{nd}$ Edition) 1974, Harper and Row, pp. 458-459, the disclosure of which is incorporated herein by reference. Once the clot is obtained, preferably the Ratnoff method may be utilized to dissolve the clot and measure the fibrinogen (FBG) by its tyrosine content. See "A New Method for the Determination of Fibrinogen in Small Samples of Plasma", Oscar D. Ratnoff, M. D. et al., J. Lab. Clin. Med., 1951: V. 37 pp. 316-320, the complete disclosure of which is incorporated herein by reference. The Ratnoff method relies on the optical density of the developed color being proportional to the concentration of fibrinogen or tyrosine and sets forth a calibration curve for determining the relationship between optical density and concentration of fibrinogen. The addition of a fibrinogen standard preferably is added to the plasma sample based on the volume of the plasma.

As is known, the addition of the reagent Thromboplastin C serves as a coagulant to cause clotting to occur within a sample of citrated blood under test which may be contained in a container 8. As clotting occurs, the A/D converter 26 of FIG. 1 will count and produce a digital value of voltage at a predetermined period, such as once every 0.05 or 0.01 seconds. As more fully described in the previously incorporated by reference U.S. Pat. No. 5,197,017 ('017), these voltage values are stored and then printed by the recorder as an array of numbers, the printing being from left to right and line by line, top to bottom. There are typically one hundred numbers in the five groups representing voltage values every second and hence, one line represents one-fifth of a second in time (20×0.01 seconds). Individual numbers in the same column are twenty sequential numbers apart. Hence, the time difference between two adjacent numbers in a column is one-fifth of a second. The significance of these recorded values may be more readily appreciated after a general review of the operating principles illustrated in FIG. 2 having a Y axis identified as Fibrinogen Concentration (Optical Density) and an X axis identified in time (seconds).

FIG. 2 illustrates the data point locations of a clotting curve related to a coagulation study which illustrates the activation and conversion of fibrinogen to fibrin. In general, FIG. 2 illustrates a "clot slope" method that may be used in a blood coagulation study carried out for determining a new anticoagulant therapy factor (nATFa). The ATFa represents an anticoagulation therapy factor represented by the expression $ATFa = XR^{(2-nFTR)}$ wherein a maximum acceleration point is obtained, and nFTR=IUX/IUT, where IUX is the change in optical density from a time prior to the MAP time ($t_{<MAP}$ which is $t_{MAP}$ minus some time from MAP) to the optical density at a time after the MAP time ($t_{>MAP}$ which is $t_{MAP}$ plus some time from MAP); and wherein IUT=the change in optical density at the time $t_1$ to the optical density measured at time $t_{EOT}$, where time $t_{EOT}$ is the end of the test (EOT). The first delta (IUX) represents the fibrinogen (FBG) for MAP (-a number of seconds) to MAP (+a number of seconds) (that is the fibrinogen (FBG) converted from $t_{<MAP}$ to $t_{>}MAP$ on FIG. 2) The (IUT) represents fibrinogen converted from $c_1$ to $c_{EOT}$ (that is the fibrinogen converted from $t_1$ to $t_{EOT}$, see FIG. 2). The XR for the ATFa expression is XR=TX/MNTX, which is the ratio of time to map (TX) by the mean normal time to map of 20 presumed "normal" patients.

The study which measures the concentration of the fibrinogen (FBG) in the plasma that contributes to the clotting of the plasma and uses an instrument, such as, for example, the potentiophotometer apparatus illustrated in FIG. 1, to provide an output voltage signal that is directly indicative of the fibrinogen (FBG) concentration in the plasma sample under test, is more fully discussed in the previously incorporated by reference U.S. Pat. No. 5,502, 651. The quantities given along the Y-axis of FIG. 2 are values (+ and -) that may be displayed by the digital recorder 28. The "clot slope" method comprises detection of the rate or the slope of the curve associated with the formation of fibrin from fibrinogen. The "clot slope" method takes into account the time to maximum acceleration (TX) which is the point at which fibrinogen conversion achieves a maximum and from there decelerates.

As seen in FIG. 2, at time $t_0$, corresponding to a concentration $c_0$, the thromboplastin/calcium ion reagent is introduced into the blood plasma which causes a disturbance to the composition of the plasma sample which, in turn, causes the optical density of the plasma sample to increase momentarily. After the injection of the reagent (the time of which is known, as to be described, by the computer 30), the digital quantity of the recorder 28 of FIG. 1 rapidly increases and then levels off in a relatively smooth manner and then continues along until the quantity $c_1$ is reached at a time $t_1$. The time which elapses between the injection of thromboplastin at to and the instant time $t_1$ of the quantity $c_1$ is the prothrombin time (PT) and is indicated in FIG. 2 by the symbol PT. As shown in FIG. 2, the baseline that develops after the thromboplastin (TP) is introduced or injected into the sample generally is thought to represent the "lag phase" of all of the enzymes preceding prothrombin converting to fibrin. The enzymes types and amounts may vary from person to person, and thus, this would demonstrate the potential for prothrombin times to vary between individuals.

An anticoagulant therapy factor (nATF) is determined. The optical density of a quantity $c_1$ directly corresponds to a specified minimum amount of fibrinogen (FBG) that must be present for a measuring system, such as the circuit arrangement of FIG. 1, to detect in the plasma sample that a clot is being formed, i.e., through the transformation of fibrinogen to fibrin. The quantities shown in FIG. 2 are of optical densities, which may be measured in instrument units, that are directly correlatable to fibrinogen concentration values. The quantity $c_1$, may vary from one clot detection system to another, but for the potentiophotometer system of FIG. 1, this minimum is defined by units of mass having a value of about 0.05 grams/liter (g/l).

Figure 3:
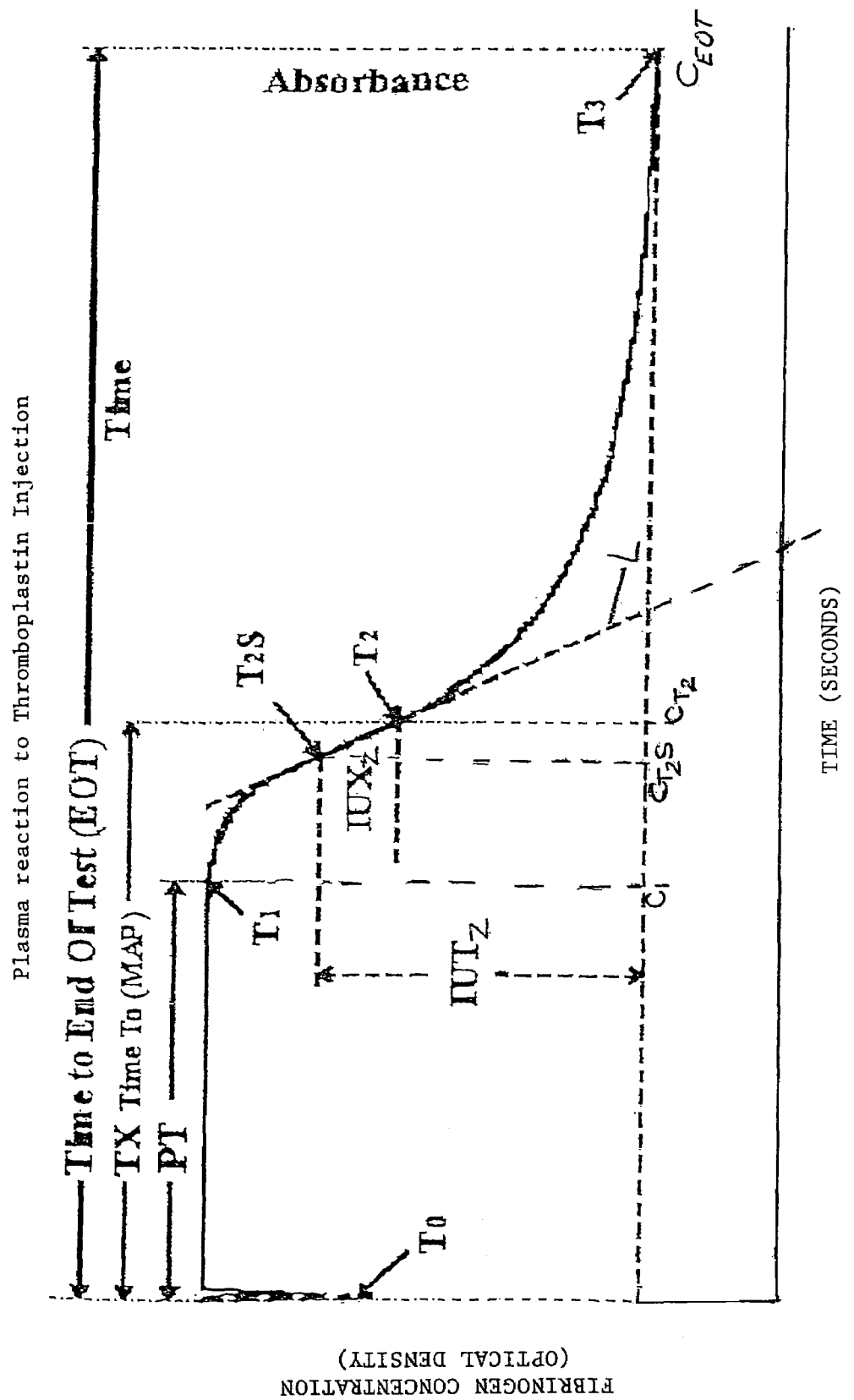
FIG. 3 is another plot of the various phases of the fibrinogen concentration occurring in a typical plasma clotting process.

Considering the clotting curve of FIG. 2, detection of a first predetermined quantity $c_1$ is illustrated occurring at a corresponding time $t_1$, which is the start of the clotting process. In accordance with one or more embodiments, this process may be monitored with the apparatus of FIG. 1 for determining a new anticoagulant therapy factor (nATF). The time $t_1$ is the beginning point of the fibrinogen formation, that is, it is the point that corresponds to the beginning of the acceleration of the fibrinogen conversion that lasts for a predetermined time, The acceleration of the fibrinogen conversion proceeds from time ($t_1$) and continues until a time $t_{MAP}$, having a corresponding quantity $c_{MAP}$. The time $t_{MAP}$, as well as the quantity $c_{MAP}$, is of primary importance because it is the point of maximum acceleration of the fibrinogen (FBG) to fibrin conversion and is also the point where deceleration of fibrinogen (FBG) to fibrin conversion begins. Further, the elapsed time from $t_0$ to $t_{MAP}$ is a time to maximum acceleration from reagent injection (TX), shown in FIG. 2. Preferably, the conversion of fibrinogen to fibrin is quantified every 0.1 seconds. The time to maximum acceleration from reagent injection (TX) is defined as the point on the clotting curve time line where this conversion has reached its maximum value for the last time, simulating a zero-order kinetic rate. To facilitate ascertainment of the location point of the last maximum value, the delta value of two points at a fixed interval may be measured until this value begins to decrease. This value is tracked for a period of time, such as for example five seconds, after the first decreasing value has been determined. This facilitates ascertainment of the last point of what may be referred to as a simulated zero-order kinetic rate. Referring to FIG. 3, a zero order kinetic rate is illustrated by the line (L).

As shown in FIG. 2, a quantity $c_{MAP}$ and a corresponding time $t_{MAP}$ define a maximum acceleration point (MAP). Fibrin formation, after a short lag phase before the MAP, occurs for a period of time, in a linear manner. Fibrinogen (FBG) is in excess during this lag phase, and fibrin formation appears linear up to the MAP.

The deceleration of fibrinogen (FBG) to fibrin conversion continues until a quantity $c_{EOT}$ is reached at a time $t_{EOT}$. The time $t_{EOT}$ is the point where the deceleration of the fibrinogen (FBG) to fibrin conversion corresponds to a value which is less than the required amount of fibrinogen (FBG) that was present in order to start the fibrinogen (FBG) to fibrin conversion process. Thus, because the desired fibrinogen (FBG) to fibrin conversion is no longer in existence, the time $t_{EOT}$ represents the ending point of the fibrinogen (FBG) to fibrin conversion in accordance with the coagulation study exemplified herein, which may be referred to as the end of the test (EOT). The fibrinogen (FBG) to fibrin conversion has a starting point of $t_1$ and an ending point of $t_{EOT}$. The differential of these times, $t_1$ and $t_{EOT}$, define a second delta (IUT).

The "clot slope" method that gathers typical data as shown in FIG. 2 has four critical parameters. The first is that the initial delta optical density of substance being analyzed should be greater than about 0.05 g/l in order for the circuit arrangement of FIG. 1 to operate effectively. Second, the acceleration fibrinogen (FBG) to fibrin conversion should be increasing for a minimum period of about 1.5 seconds so as to overcome any false reactions created by bubbles. Third, the total delta optical density (defined by the difference in quantities $c_1$ and $c_{EOT}$) should be at least three (3) times the instrument value in order to perform a valid test, i.e., (3)*(0.05 g/l)=0.15 g/l. Fourth, the fibrinogen (FBG) to fibrin conversion is defined, in part, by the point ($t_{EOT}$) where the deceleration of conversion becomes less than the instrument value of about 0.05 g/l that is used to detect the clot point ($t_1$). As with most clot detection systems, a specific amount of fibrinogen needs to be present in order to detect a clot forming. Adhering to the four given critical parameters is an example of how the present apparatus and method may be used to carry out a coagulation study to determine a specific quantity of fibrinogen. In order for that specific amount of fibrinogen to be determined, it is first necessary to detect a clot point ($t_1$). After that clot point ($t_1$) is detected, it logically follows that when the fibrinogen conversion becomes less than the specific amount (about 0.05 g/l for the circuit arrangement of FIG. 1), the end point ($t_{EOT}$) of the fibrinogen conversion has been reached.

One embodiment of the method and apparatus is illustrated in accordance with the clotting curve shown in FIG. 3. The clotting curve of FIG. 3 illustrates the values ascertained in arriving at a new anticoagulation therapy factor (nATFz). The embodiment illustrates the determination of a new anticoagulation therapy factor (nATFz), expressed by the following formula:

$$nATFz = XR^{(2-nFTR)} \quad (1)$$

This embodiment utilizes a zero order line (L) to obtain a first delta, in particular IUXz, which is a first differential taken along the simulated zero order kinetic line (L), and preferably along the segment between the start of the simulated zero order kinetic ($T_2S$) to the last highest absorbance value ($T_2$) (i.e., preferably, the last highest absorbance value of a simulated zero order kinetic). As previously discussed, the acceleration of the fibrinogen conversion proceeds from a first time, here time ($T_1$) and continues, eventually reaching a time where the last highest delta absorbance value or maximum acceleration point ($T_2$) having a corresponding quantity $c_{T2}$ is reached. The values for "T" correspond with times, and the values for "c" correspond with quantity, which may be measured in instrument units based on optical density readings (also referred to as optical density or o.d.). The time $T_2$, as well as the quantity $c_{T2}$, is the point of maximum acceleration of the fibrinogen (FBG) to fibrin conversion and is also the point where deceleration of fibrinogen (FBG) to fibrin conversion begins. In this embodiment, IUXz is the change in optical density preferably from the beginning of the at the time $T_2S$ at which the simulated zero order kinetic begins to the optical density at time $T_2$ which is the maximum acceleration point or the last highest delta absorbance value of a simulated zero order kinetic. FIG. 3 shows the differential IUXz taken between a preferred segment of the zero order line. The second delta in particular (IUTz) is the change in optical density at the time $T_2S$ to the optical density measured at time $T_3$, where time $T_3$ is the end of the test (EOT).

The (IUXz) represents the fibrinogen (FBG) converted between time $T_2S$ and $T_2$. The (IUTz) represents fibrinogen converted from the time $T_2S$ to the end of the test or $T_3$.

The maximum acceleration ratio (XR) for this embodiment is calculated to arrive at the new alternate anticoagulation therapy factor (nATFz). The maximum acceleration ratio (XR) is defined as the time to maximum acceleration from reagent injection (TX) divided by the mean normal TX value of a number of presumed normal specimens (MNTX). For example, the mean normal TX value may be derived based on the value of 20 or more presumed normal specimens. The maximum acceleration ratio (XR) may be expressed through the following formula:

$$XR = TX/MNTX \quad (2)$$

The clotting curve of FIG. 3 illustrates the values ascertained in arriving at the new alternate anticoagulation therapy factor (nATFz). The new alternate anticoagulation therapy factor (nATFz) is preferably expressed by the following formula:

$$nATFz = XR^{(2-nFTR)} \quad (3)$$

with FTR being IUXz/IUTz.

The preferred IBM-compatible computer 30 of FIG. 1 stores and manipulates these digital values corresponding to related data of FIG. 3 and is preferably programmed as follows:

(a) a sample of blood where the plasma is available, such as, for example, a sample of citrated blood, is obtained and placed in an appropriate container, the computer 30, as well as the recorder 28, sequentially records voltage values for a few seconds before injection of thromboplastin. As previously discussed, thromboplastin (tissue factor) is one of the factors in the human body that causes blood to clot. Prothrombin is another. Fibrinogen is yet another. Before injection of the thromboplastin, the output from the A/D converter 26 is relatively constant. When thromboplastin is injected into the plasma sample in the container, a significant and abrupt change occurs in the recorded voltage values of both the computer 30 and the recorder 28. This abrupt change is recognized by both the recorder 28 and, more importantly, by the computer 30 which uses such recognition to establish $T_o$. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed with reference to FIG. 3;

(b) the computer 30 may be programmed to look for a digital quantity representative of a critical quantity $c_1$, and when such occurs, record its instant time $T_1$. (The time span between $T_o$ and $T_1$ is the prothrombin time (PT), and has an normal duration of about 12 seconds, but may be greater than 30 seconds);

(c) following the detection of the quantity $c_1$, the computer 30 may be programmed to detect for the acceleration of fibrinogen (FBG) to fibrin conversion. The computer 30 is programmed to detect the maximum acceleration quantity $c_{MAP}$ or $C_{T2}$ as illustrated in FIG. 3, and its corresponding time of occurrence $t_{MAP}$, which is $T_2$ in FIG. 3.

(d) the computer detects a quantity $c_{EOT}$ occurring at time $t_{EOT}$. Typically, it is important that the rate of fibrin formation increase for at least 1.5 seconds following the occurrence of ($T_1$);

(e) The computer 30 is programmed to ascertain the value for the time to start ($T_2S$) which corresponds with the time at which the simulated zero order kinetic rate begins.

(f) following the detection of the acceleration of fibrinogen conversion to detect the start time $T_2S$, the computer 30 is programmed to detect for a deceleration of the fibrinogen conversion, wherein the fibrinogen concentration decreases from a predetermined quantity $c_{MAP}$ to a predetermined quantity $c_{EOT}$ having a value which is about equal but less than the first quantity $c_1$. The computer is programmed to ascertain a first delta (IUTz), by determining the difference between the quantity $c_{T2S}$ and the quantity $c_{EOT}$; and a second delta (IUXz) by determining the difference between the quantity $c_{T2S}$ and the quantity $c_2$ (or $c_{MAP}$).

(g) the computer 30 manipulates the collected data of (a); (b); (c); (d); (e) and (f) above, to determine the new fibrinogen transfer rate (nFTR). The nFTR may be arrived at based on the principle that if a required amount (e.g., 0.05 g/l) of fibrinogen concentration $c_1$ is first necessary to detect a clot point ($T_1$); then when the fibrinogen concentration ($c_{EOT}$) becomes less than the required amount $c_1$, which occurs at time ($T_{EOT}$), the fibrinogen end point has been reached. More particularly, the required fibrinogen concentration $c_1$ is the starting point of fibrinogen conversion of the clotting process and the less than required fibrinogen concentration $c_{EOT}$ is the end point of the fibrinogen conversion of the clotting process.

(h) The computer now has the information needed to determine the new fibrinogen transfer rate (nFTRz) which is expressed by the following formula:

$$nFTRz = IUXz/IUTz \qquad (4)$$

(i) data collected is manipulated by the computer 30 to calculate the maximum acceleration ratio (XR), which is expressed as TX divided by the mean normal TX value of at least 20 presumed normal specimens (MNTX):

$$XR = TX/MNTX \qquad (2)$$

The MNTX value may be ascertained and stored in the computer for reference.

(j) the computer 30 now has the information needed to determine the nATFz, (also referred to as INRz) which typically is expressed as:

$$nATFz \text{ or } INRZ = XR^{(2-nFTR)} \qquad (3)$$

where, in the exponent, the value 2 is the logarithm of the total fibrinogen, which, as expressed in terms of the optical density, is 100% transmittance, the log of 100 being 2.

The new anticoagulation therapy factor (nATFz) does not require an ISI value, as was previously used to determine anticoagulation therapy factors. The new anticoagulation therapy factor (nATFz) uses for its ascertainment the values extracted from the clotting curve (see FIG. 3), in particular (nFTRz) (determined based on IUXz and IUTz), and (TX). In carrying out coagulation studies, the new anticoagulant therapy factor (nATFz) may replace INR in anticoagulant therapy management.

The apparatus and method for obtaining a new anticoagulant therapy factor, (nATFz), may be accomplished without encountering the complications involved with obtaining the prior art quantities International Normalized Ratio (INR) and International Sensitivity Index (ISI).

The new anticoagulant therapy factor (nATFz or ATF) preferably is a replacement for the International Normalized Ratio (INR), hence it may be referred to as INRz. Existing medical literature, instrumentation, and methodologies are closely linked to the International Normalized Ratio (INR). The nATFz was compared for correlation with the INR by comparative testing, to INR quantities, even with the understanding that the INR determination may have an error of about ten (10) % which needs to be taken into account to explain certain inconsistencies.

Table 2, below, includes anticoagulant therapy factors obtained from patients at two different hospitals. The ATFz values were obtained, with GATFz representing one geographic location where patients were located and MATFz being another location. The ATFz was obtained as the new anticoagulant therapy factor, and as illustrated in Tables 4 and 5, below, compares favorably to results obtained for INR determinations.

Figure 4:
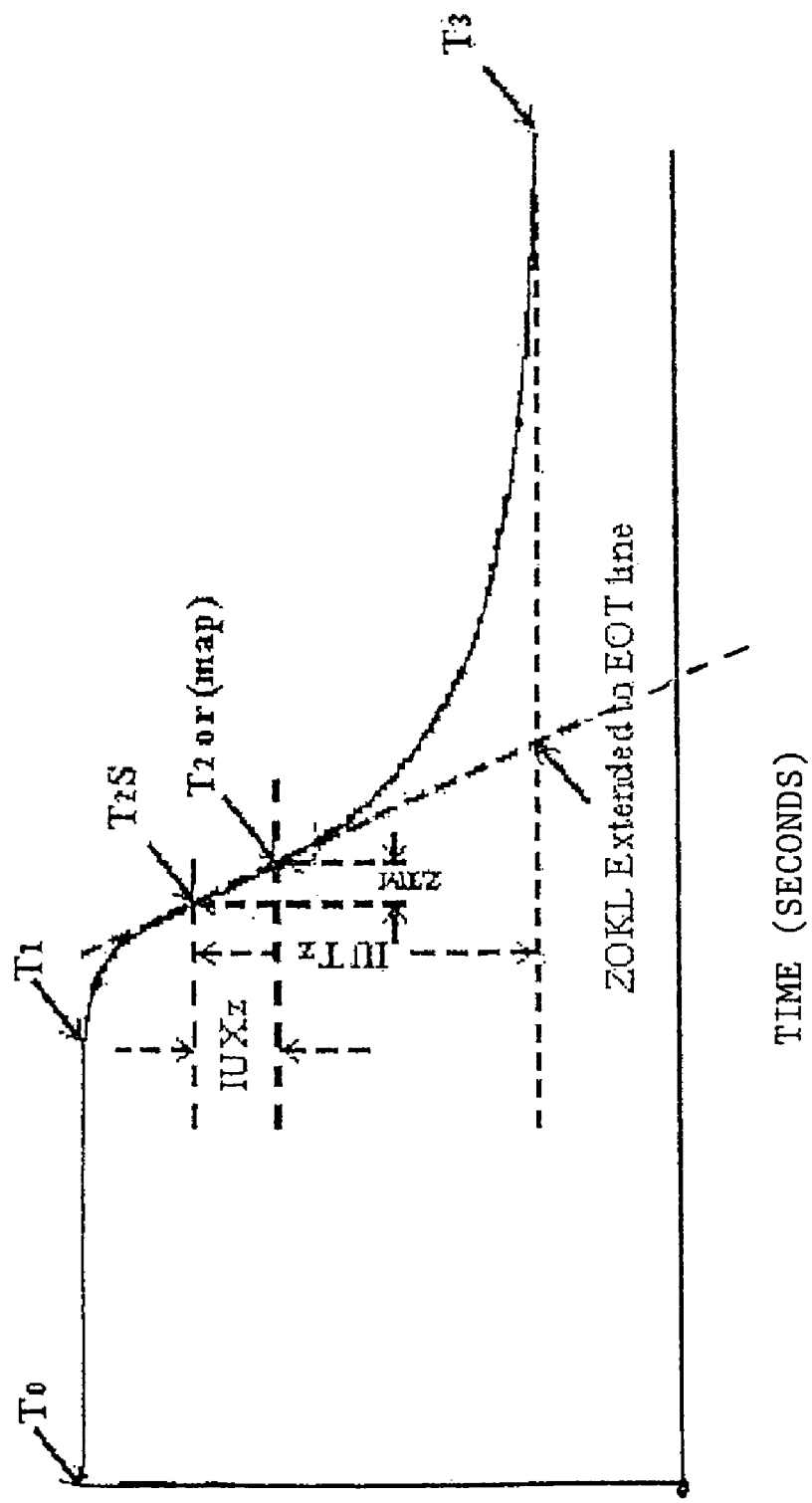
FIG. 4 is another plot of the various phases of the fibrinogen concentration occurring in a typical plasma clotting process.

Another alternate embodiment for determining a new anticoagulant therapy factor (ATFt) is provided. The alternate embodiment for determining ATFt eliminates the need for determining a mean normal prothrombin time (MNPT) (or MNXT) and ISI, saving considerable time and costs, and removing potential sources of error, as the MNPT (the expected value of MNPT's depending on the varying 20 presumed normals population) and ISI (generally provided by the manufacturer of the reagent—such as, for example, the thromboplastin, etc.) are not required for the determination of the ATFt. An alternate embodiment for determining ATFt is illustrated in accordance with the clotting curve shown in FIG. 4. The clotting curve of FIG. 4 illustrates values ascertained in arriving at the alternate new anticoagulation therapy factor (nATFt). The alternate new anticoagulation therapy factor (nATFt) is preferably expressed by the following formula:

$$nATFt = \text{Value 1} * \text{Value 2} \qquad (4)$$

The alternate embodiment utilizes the zero order line (L) to obtain a first delta, in particular IUXz, which is a first differential taken along the simulated zero order kinetic line (L), and preferably along the segment between the start of the simulated zero order kinetic ($T_2S$) to the last highest absorbance value ($T_2$) (i.e., preferably, the last highest absorbance value of a simulated zero order kinetic). As previously discussed, the acceleration of the fibrinogen conversion proceeds from a first time, here time ($T_1$) and continues, eventually reaching a time where the last highest delta absorbance value or maximum acceleration point ($T_2$) having a corresponding quantity $c_{T2}$ is reached. The time $T_2$, as well as the quantity $c_{T2}$, is the point of maximum acceleration of the fibrinogen (FBG) to fibrin conversion and also is the point where deceleration of fibrinogen (FBG) to fibrin conversion begins. As illustrated on the clotting chart in FIG. 4, IUXz represents a change in optical density (o.d.) preferably from the beginning of the at the time $T_2S$ at which the simulated zero order kinetic begins to the optical density at time $T_2$ which is the maximum acceleration point or the last highest delta absorbance value of a simulated zero order kinetic. The value IUXz is generally expressed in instrument units (corresponding to absorbance or percent transmittance) and may generally be referred to as optical density or o.d. FIG. 4 shows the differential IUXz taken between a preferred segment of the zero order line. The second delta in particular (IUTz) represents a change in optical density at a time $T_2S$ to the optical density measured at a time $T_3$, where time $T_3$ is the end of the test (EOT).

The (IUXz) represents the fibrinogen (FBG) converted between time $T_2S$ and $T_2$. The (IUTz) represents fibrinogen converted from the time $T_2S$ to the end of the test or $T_3$.

The first value V1 corresponds to the value determined for the theoretical end of test (TEOT), which, as illustrated in the clotting curve representation in FIG. 4, is where the zero order kinetic line (L) crosses the line $y=T_3$. The value TEOT is the elapsed time to convert the total instrument units (TIU) at the zero order kinetic rate, which is representative of the fibrinogen in the sample undergoing the conversion to fibrin. In other words, the expression for the first value (V1), or TEOT, is:

$$V1 = TEOT = ZTM/IUXz * IUTz \qquad (5)$$

where ZTM is the time between Tmap (i.e., $T_2$ shown on FIG. 4) and T2S. ZTM may be generally represented by the following expression:

$$ZTM = T_2 - T_2S \quad (6)$$

A second value, V2, also referred to as a multiplier, is determined based on the value $T_2S$. In the expression for the ATFt, the second value, V2, may be obtained by taking the value of the time ($T_2S$) corresponding to a second time (t2) or the maximum acceleration point (Tmap), and scaling this value. It is illustrated in this embodiment that the multiplier is derived from the natural log base "e", which is 2.71828, scaled to provide an appropriately decimaled value. The scaling number used in the example set forth for this embodiment is 100. The second value (V2) may be expressed by the following relationship:

$$V2 = T_2S/100e \quad (7)$$

where $T_2S$ is the maximum acceleration point for the sample, and 100e is the value 100 multiplied by the natural log base "e" (2.71828) or 271.828. The new anticoagulation therapy factor according to the alternate embodiment may be expressed as follows:

$$nATFt = [(T_2-T_2S)/IUXz * IUTz] * [T_2S/M] \quad (8)$$

where M represents a multiplier. In the present example, the multiplier M, corresponds to the value 271.828 (which is 100 times the natural log base "e").

Figure 5:
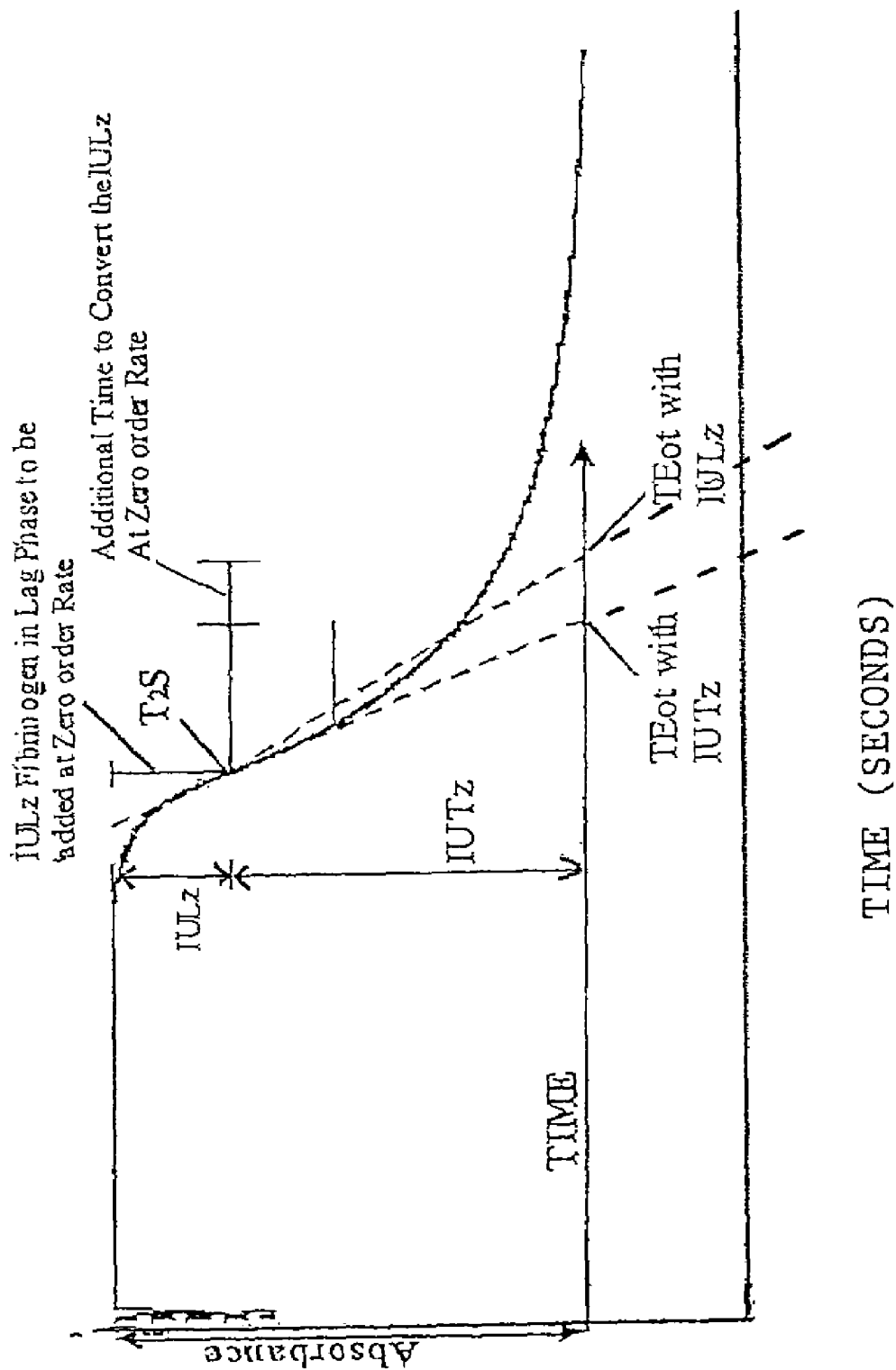
FIG. 5 is another plot of the various phases of the fibrinogen concentration occurring in a typical plasma clotting process illustrating the fibrinogen lag phase.

An alternate embodiment of an anticoagulant therapy factor, ATFt2, which does not require the ascertainment of a mean normal prothrombin time (MNPT) or use of an ISI value, is derived using the expression (5), wherein the IUTz is replaced by the expression (IUTZ+IULZ). In this alternate expression the method is carried out to ascertain the values for Value1 and Value2, in the manner described herein, with Value 1 being obtained through expression (5.1):

$$V1 = TEOT = ZTM/IUXz * (IUTz + IULz) \quad (5.1)$$

where IULz is time to convert the lag phase fibrinogen (FBG) measured along the ordinate between T1 and T2S. In expression 5.1, the theoretical end of test (TEOT) is set to include the time to convert the fibrinogen (FBG) in the lag phase of the clotting curve. FIG. 5 illustrates the fibrinogen lag phase and the TEOT obtained from the line L2, and shows the IULz. ATFt2 is expressed by the following:

$$nATFt2 = [(T_2-T_2S)/IUXz * (IUTz + IULz)] * [T_2S/M] \quad (8.1)$$

The apparatus may comprise a computer which is programmed to record, store and process data. The zero order rate may be determined by ascertaining data from analyzing the sample, and optical density properties. One example of how this may be accomplished is using two arrays, a data array and a sub array. A data array may be ascertained by collecting data over a time interval. In one embodiment, for example, the data array may comprise a sequential list of optical densities, taken of a sample by an optical analytical instrument, such as, for example, a spectrophotometer, for a frequency of time. In the example, the frequency of sample data is taken every $100^{th}$ of a second. In this embodiment, a computer is programmed to record the optical density of the sample, every $100^{th}$ of a second. Two values, NOW and THEN, for the data array are provided for ascertaining the Prothrombin Time (PT) (which is the time point $T_1$), maximum acceleration point (MAP), and end of test point (EOT). Two time definitions may be specified, one being the interval between NOW and THEN on the clotting curve, which may be 2.72 seconds ($272/100^{th}$ of a second), the second being the size of the filter used for signal averaging. NOW is the sum of the last 20 optical densities and THEN is the sum of the 10 prior data points 2.72 seconds prior to NOW. A graphical illustration is provided in FIG. 5. As illustrated in FIG. 5, four values are defined: SUM(NOW), SUM(THEN), AVERAGE(NOW) and AVERAGE(THEN). The average is the sum divided by the filter value.

The sub array may be defined as a sequential list of delta absorbance units. This may begin at $T_1$, the prothrombin time (PT), and continue until the last highest delta absorbance (delta A) has been detected, then continues an additional five (5) seconds to insure the last delta A has been found. A determination of $T_2S$ may be accomplished by locating within the sub array, the first occurrence of when the sub array delta value is greater than or equal to 80% of the highest delta absorbance units. The first derivative is ascertained by computing the difference between (NOW) and (THEN). The PT is ascertained by determining the point prior to the positive difference between AVERAGE(THEN) and AVERAGE(NOW) for a period of 2.72 seconds or 272 ticks. The MAP is the point where the last highest difference between SUM(THEN) and SUM(NOW) has occurred. The computer may be programmed to store this delta A value in the sub array. The EOT may be ascertained by determining the point prior to where the difference between SUM (THEN) and SUM(NOW) is less than one.

Table 2 illustrates examples of samples, identified by ID numbers, along with corresponding data which compares the ATF values obtained for an ATF determined through the prior method, using ISI and INR values (represented as ATFa), an ATF determined through the use of a zero order kinetic reaction using the MNTX (nATFz), and an ATF determined without using the MNXT or ISI (nATFt). The data in table 2 represents universal laboratory data from combined locations for the patients listed. The data is based on analysis of absorbance data, storage of the data by the computer, such as, for example, with a storage device, like a hard drive, and retrieving the data and processing the data. The data, in the example represented in Table 2 was processed using the definitions and NOW and THEN intervals.

TABLE 2

| ID | AINR | GINR | GatfA | GatfZ | GatfT | MINR | MatfA | MatfZ | MatfT |
|---|---|---|---|---|---|---|---|---|---|
| U0047 | 2.10 | 1.70 | 1.76 | 1.74 | 1.62 | 2.00 | 2.08 | 1.78 | 1.68 |
| U0048 | 1.80 | 1.80 | 1.84 | 1.83 | 1.72 | 1.90 | 1.96 | 1.85 | 1.82 |
| U0050 | 1.80 | 1.70 | 1.77 | 1.80 | 1.68 | 1.80 | 2.00 | 1.80 | 1.70 |
| U0056 | 1.60 | 1.50 | 1.54 | 1.54 | 1.40 | 1.80 | 1.83 | 1.61 | 1.48 |
| U0058 | 3.20 | 2.80 | 2.93 | 2.92 | 2.93 | 3.30 | 3.38 | 3.10 | 3.29 |
| U0060 | 2.20 | 2.10 | 2.15 | 2.17 | 2.11 | 2.20 | 2.21 | 2.26 | 2.27 |
| U0062 | 2.80 | 2.60 | 2.69 | 2.72 | 2.69 | 3.00 | 3.19 | 2.86 | 2.91 |
| U0415 | 0.90 | 0.90 | 0.88 | 0.94 | 0.74 | 0.90 | 0.95 | 0.97 | 0.83 |

TABLE 2-continued

| ID | AINR | GINR | GatfA | GatfZ | GatfT | MINR | MatfA | MatfZ | MatfT |
|---|---|---|---|---|---|---|---|---|---|
| U0432 | 1.80 | 1.50 | 1.53 | 1.42 | 1.24 | 1.40 | 1.39 | 1.46 | 1.33 |
| U0436 | 2.40 | 2.40 | 2.57 | 2.24 | 1.99 | 2.40 | 2.41 | 2.28 | 2.17 |
| U0438 | 3.90 | 3.70 | 4.25 | 3.26 | 3.21 | 3.80 | 4.22 | 3.40 | 3.55 |
| U0439 | 2.30 | 2.20 | 2.27 | 1.94 | 1.75 | 2.30 | 2.32 | 2.07 | 2.02 |
| U0440 | 5.80 | 4.80 | 5.41 | 4.33 | 4.50 | 4.60 | 4.84 | 4.55 | 5.18 |
| U0441 | 4.50 | 4.90 | 5.58 | 5.01 | 4.86 | 4.40 | 4.71 | 4.64 | 5.35 |
| U0442 | 1.80 | 1.70 | 1.79 | 1.65 | 1.48 | 1.80 | 1.84 | 1.64 | 1.52 |
| U0800 | 2.00 | 2.00 | 2.02 | 1.78 | 1.64 | 2.10 | 2.11 | 2.12 | 2.09 |
| U0843 | 1.40 | 1.40 | 1.43 | 1.42 | 1.22 | 1.40 | 1.47 | 1.44 | 1.31 |
| U0848 | 1.30 | 1.40 | 1.41 | 1.31 | 1.13 | 1.30 | 1.37 | 1.34 | 1.23 |
| U0849 | 2.40 | 2.30 | 2.44 | 1.94 | 1.77 | 2.30 | 2.38 | 1.98 | 1.93 |
| U0855 | 1.30 | 1.30 | 1.29 | 1.35 | 1.17 | 1.20 | 1.24 | 1.36 | 1.22 |
| U0860 | 1.00 | 1.00 | 0.99 | 1.00 | 0.77 | 1.00 | 0.97 | 1.00 | 0.85 |
| U0861 | 2.80 | 2.90 | 2.98 | 2.70 | 2.58 | 3.00 | 2.99 | 2.88 | 3.00 |
| U0863 | 1.70 | 1.70 | 1.70 | 1.76 | 1.65 | 1.70 | 1.77 | 1.83 | 1.79 |
| U0867 | 3.20 | 2.90 | 3.19 | 2.64 | 2.38 | 3.00 | 3.10 | 2.85 | 2.83 |
| U0875 | 2.20 | 2.00 | 2.16 | 1.80 | 1.60 | 2.00 | 2.02 | 1.81 | 1.71 |
| U1198 | 2.20 | 2.10 | 2.17 | 2.07 | 1.91 | 2.00 | 1.98 | 2.22 | 2.22 |
| U1199 | 2.80 | 3.30 | 3.57 | 2.79 | 2.76 | 3.20 | 3.21 | 2.99 | 3.28 |
| U1201 | 1.90 | 1.90 | 1.95 | 1.76 | 1.62 | 1.80 | 1.84 | 1.82 | 1.80 |
| U1202 | 1.30 | 1.30 | 1.35 | 1.31 | 1.16 | 1.40 | 1.39 | 1.35 | 1.20 |
| U1205 | 1.60 | 1.80 | 1.90 | 1.71 | 1.53 | 1.90 | 1.90 | 1.80 | 1.67 |
| U1207 | 1.90 | 1.90 | 1.96 | 1.68 | 1.49 | 1.90 | 1.87 | 1.78 | 1.61 |
| U1218 | 3.00 | 2.60 | 2.86 | 2.57 | 2.56 | 2.80 | 3.07 | 2.90 | 3.08 |
| U1225 | 2.20 | 2.30 | 2.34 | 2.01 | 1.83 | 2.60 | 2.40 | 2.21 | 2.16 |
| U1230 | 1.30 | 1.40 | 1.45 | 1.47 | 1.32 | 1.40 | 1.45 | 1.50 | 1.45 |
| U1575 | 1.40 | 1.30 | 1.30 | 1.53 | 1.41 | 1.40 | 1.44 | 1.49 | 1.35 |
| U1576 | 2.20 | 2.10 | 2.11 | 2.10 | 2.02 | 2.30 | 2.32 | 2.19 | 2.17 |
| U1579 | 1.50 | 1.70 | 1.72 | 1.64 | 1.49 | 1.80 | 1.81 | 1.61 | 1.44 |
| U1581 | 1.70 | 1.70 | 1.74 | 1.85 | 1.81 | 1.70 | 1.77 | 1.74 | 1.73 |
| U1599 | 2.00 | 1.70 | 1.78 | 2.01 | 1.96 | 2.00 | 2.14 | 2.04 | 1.93 |
| U1600 | 3.50 | 3.30 | 3.39 | 3.58 | 3.63 | 3.90 | 4.21 | 3.37 | 3.64 |
| U1649 | 0.90 | 0.80 | 0.80 | 0.94 | 0.76 | 0.90 | 0.89 | 0.89 | 0.74 |
| U3050 | 2.70 | 2.80 | 3.08 | 2.34 | 2.17 | 2.30 | 2.34 | 2.05 | 2.02 |
| U3077 | 1.30 | 1.40 | 1.44 | 1.34 | 1.17 | 1.30 | 1.28 | 1.31 | 1.16 |
| U3083 | 1.60 | 1.60 | 1.58 | 1.47 | 1.31 | 1.60 | 1.68 | 1.48 | 1.37 |
| U3395 | 2.70 | 3.20 | 3.51 | 2.80 | 2.70 | 2.80 | 2.90 | 2.38 | 2.32 |
| U3398 | 1.50 | 1.70 | 1.77 | 1.60 | 1.47 | 1.60 | 1.65 | 1.61 | 1.47 |
| U3408 | 1.10 | 1.20 | 1.18 | 1.13 | 0.92 | 1.10 | 1.03 | 1.09 | 0.94 |
| U3453 | 1.10 | 1.20 | 1.24 | 1.19 | 0.97 | 1.20 | 1.18 | 1.11 | 1.00 |
| U3456 | 1.10 | 1.00 | 0.96 | 0.99 | 0.81 | 1.00 | 0.98 | 1.04 | 0.90 |
| U3457 | 2.20 | 2.30 | 2.38 | 2.03 | 1.94 | 2.10 | 2.28 | 1.94 | 1.86 |
| U3459 | 2.90 | 2.60 | 2.81 | 2.40 | 2.22 | 2.40 | 2.53 | 2.11 | 2.04 |
| U3724 | 2.70 | 2.40 | 2.47 | 2.16 | 1.95 | 2.60 | 2.72 | 2.31 | 2.25 |
| U4471 | 1.50 | 1.60 | 1.67 | 1.63 | 1.43 | 1.70 | 1.71 | 1.71 | 1.62 |
| U4737 | 2.90 | 2.60 | 2.79 | 2.42 | 2.26 | 2.70 | 2.87 | 2.51 | 2.2 |
| U4752 | 1.40 | 1.50 | 1.55 | 1.47 | 1.26 | 1.50 | 1.48 | 1.46 | 1.33 |
| U4757 | 2.00 | 2.10 | 2.09 | 1.95 | 1.77 | 2.00 | 2.02 | 2.00 | 1.92 |
| U4767 | 2.60 | 2.40 | 2.52 | 2.16 | 1.95 | 2.60 | 2.56 | 2.33 | 2.27 |
| U4772 | 2.50 | 2.70 | 2.78 | 2.59 | 2.58 | 2.80 | 2.84 | 2.55 | 2.56 |
| U4801 | 1.30 | 1.40 | 1.41 | 1.33 | 1.13 | 1.50 | 1.49 | 1.41 | 1.22 |
| U5133 | 0.90 | 0.90 | 0.91 | 0.92 | 0.74 | 1.00 | 0.97 | 0.97 | 0.78 |
| U5158 | 5.50 | 5.10 | 5.90 | 5.34 | 5.64 | 6.00 | 6.57 | 6.50 | 7.00 |
| U5169 | 2.60 | 2.90 | 3.16 | 3.14 | 3.09 | 3.20 | 3.35 | 3.35 | 3.67 |
| U5173 | 1.10 | 1.20 | 1.17 | 1.19 | 1.02 | 1.20 | 1.21 | 1.16 | 1.03 |
| U5175 | 1.70 | 1.80 | 1.86 | 1.85 | 1.67 | 1.90 | 1.92 | 1.82 | 1.70 |
| U5178 | 2.30 | 2.20 | 2.28 | 2.02 | 1.79 | 2.60 | 2.85 | 2.03 | 2.01 |
| U5183 | 2.90 | 2.60 | 2.83 | 2.43 | 2.23 | 3.60 | 3.86 | 2.88 | 3.01 |
| U5190 | 2.80 | 2.70 | 2.82 | 2.85 | 2.70 | 3.20 | 3.36 | 3.00 | 3.15 |
| U5193 | 3.10 | 3.00 | 3.13 | 2.93 | 2.81 | 3.60 | 3.73 | 3.33 | 3.30 |
| U5565 | 2.70 | 3.20 | 3.34 | 3.16 | 3.04 | 3.50 | 3.48 | 3.31 | 3.50 |
| U5589 | 1.60 | 1.80 | 1.86 | 1.69 | 1.52 | 1.90 | 1.96 | 1.64 | 1.44 |
| U5591 | 2.00 | 2.20 | 2.33 | 2.16 | 1.98 | 2.30 | 2.28 | 2.19 | 2.24 |
| U5592 | 1.10 | 1.20 | 1.23 | 1.26 | 1.09 | 1.40 | 1.35 | 1.49 | 1.37 |
| U5593 | 1.70 | 1.80 | 1.89 | 1.76 | 1.55 | 1.80 | 1.85 | 1.76 | 1.70 |
| U5594 | 2.30 | 2.60 | 2.79 | 2.84 | 2.81 | 2.80 | 2.84 | 2.85 | 2.96 |
| U5597 | 3.30 | 3.30 | 3.64 | 3.25 | 2.96 | 4.10 | 4.03 | 3.85 | 4.08 |
| U5992 | 1.40 | 1.40 | 1.42 | 1.45 | 1.29 | 1.30 | 1.37 | 1.37 | 1.30 |
| U5993 | 1.00 | 0.90 | 0.94 | 1.03 | 0.84 | 1.00 | 0.98 | 1.03 | 0.84 |
| U6017 | 1.00 | 0.90 | 0.95 | 0.99 | 0.77 | 0.90 | 0.89 | 0.97 | 0.79 |
| U6047 | 2.30 | 2.30 | 2.36 | 2.17 | 1.97 | 2.20 | 2.28 | 2.23 | 2.22 |
| U6056 | 1.00 | 1.00 | 1.01 | 1.03 | 0.87 | 1.00 | 1.01 | 1.02 | 0.85 |
| U6060 | 1.90 | 2.10 | 2.17 | 2.10 | 1.94 | 2.30 | 2.00 | 2.16 | 2.12 |
| U6065 | 3.10 | 2.80 | 2.93 | 2.77 | 2.60 | 3.00 | 3.13 | 2.74 | 2.76 |
| U6928 | 1.20 | 1.20 | 1.17 | 1.34 | 1.17 | 1.20 | 1.24 | 1.22 | 1.05 |
| U6929 | 1.20 | 1.20 | 1.20 | 1.23 | 1.06 | 1.20 | 1.19 | 1.15 | 0.98 |
| U6936 | 2.40 | 2.50 | 2.45 | 3.02 | 3.15 | 2.60 | 2.61 | 2.51 | 2.60 |

TABLE 2-continued

| ID | AINR | GINR | GatfA | GatfZ | GatfT | MINR | MatfA | MatfZ | MatfT |
|---|---|---|---|---|---|---|---|---|---|
| U6938 | 2.10 | 2.10 | 2.12 | 2.30 | 2.22 | 2.30 | 2.26 | 2.25 | 2.21 |
| U6951 | 1.50 | 1.50 | 1.51 | 1.59 | 1.42 | 1.60 | 1.66 | 1.49 | 1.36 |
| U6972 | 2.40 | 2.40 | 2.47 | 2.57 | 2.49 | 2.80 | 2.84 | 2.54 | 2.51 |
| U6977 | 1.30 | 1.30 | 1.34 | 1.35 | 1.19 | 1.30 | 1.37 | 1.23 | 1.08 |
| U6987 | 5.10 | 4.50 | 4.43 | 5.29 | 5.42 | 5.70 | 5.44 | 6.16 | 6.82 |
| U7316 | 1.20 | 1.10 | 1.15 | 1.28 | 1.14 | 1.30 | 1.28 | 1.26 | 1.11 |
| U7317 | 2.00 | 1.60 | 1.68 | 1.66 | 1.56 | 1.90 | 1.90 | 1.68 | 1.56 |
| U7318 | 2.80 | 2.70 | 2.86 | 2.71 | 2.57 | 3.30 | 3.40 | 2.70 | 2.72 |
| U7320 | 2.00 | 1.90 | 1.92 | 2.17 | 2.13 | 2.00 | 2.06 | 2.12 | 2.13 |
| U7321 | 1.50 | 1.40 | 1.38 | 1.59 | 1.50 | 1.60 | 1.60 | 1.61 | 1.51 |
| U7322 | 1.80 | 1.70 | 1.72 | 1.63 | 1.46 | 1.70 | 1.76 | 1.55 | 1.42 |
| U7324 | 1.30 | 1.20 | 1.25 | 1.33 | 1.17 | 1.40 | 1.40 | 1.30 | 1.13 |
| U7440 | 2.60 | 3.00 | 2.98 | 2.90 | 2.89 | 3.00 | 3.01 | 3.05 | 3.37 |
| U7443 | 2.00 | 2.00 | 2.03 | 1.87 | 1.73 | 2.10 | 2.17 | 1.90 | 1.79 |
| U7458 | 1.40 | 1.40 | 1.43 | 1.38 | 1.20 | 1.40 | 1.40 | 1.40 | 1.26 |
| U7465 | 9.70 | 7.40 | 8.12 | 6.47 | 7.80 | 7.10 | 7.54 | 7.06 | 7.63 |
| U7469 | 1.10 | 1.10 | 1.11 | 1.11 | 0.86 | 1.20 | 1.14 | 1.10 | 0.90 |
| U7470 | 3.20 | 3.40 | 3.65 | 3.27 | 3.12 | 3.60 | 3.67 | 3.62 | 3.70 |
| U7707 | 2.20 | 2.20 | 2.27 | 2.34 | 2.28 | 2.30 | 2.29 | 2.23 | 2.22 |
| U7708 | 1.60 | 1.60 | 1.60 | 1.73 | 1.61 | 1.70 | 1.73 | 1.71 | 1.62 |
| U7710 | 2.30 | 2.50 | 2.64 | 2.71 | 2.73 | 2.70 | 2.85 | 2.75 | 2.96 |
| U7713 | 1.40 | 1.60 | 1.59 | 1.57 | 1.50 | 1.60 | 1.64 | 1.58 | 1.48 |
| U7724 | 2.40 | 2.40 | 2.47 | 2.62 | 2.65 | 2.70 | 2.73 | 2.75 | 2.84 |
| U7727 | 1.70 | 1.70 | 1.73 | 1.78 | 1.68 | 1.90 | 1.90 | 1.91 | 1.86 |
| U7738 | 2.40 | 2.30 | 2.45 | 2.27 | 2.21 | 2.40 | 2.54 | 2.29 | 2.32 |
| U7794 | 1.90 | 1.80 | 1.91 | 1.72 | 1.58 | 1.70 | 1.78 | 1.71 | 1.55 |
| U8080 | 3.10 | 3.60 | 3.63 | 3.41 | 3.54 | 3.30 | 3.33 | 3.18 | 3.34 |
| U8087 | 1.90 | 1.90 | 1.95 | 1.80 | 1.62 | 1.90 | 1.91 | 1.79 | 1.74 |
| U8092 | 1.70 | 1.70 | 1.76 | 1.67 | 1.49 | 1.90 | 1.93 | 1.67 | 1.57 |
| U8210 | 2.60 | 2.90 | 3.04 | 2.72 | 2.8 | 2.70 | 2.77 | 2.54 | 2.56 |
| U8221 | 3.20 | 3.70 | 3.99 | 3.42 | 3.35 | 3.50 | 3.47 | 3.24 | 3.46 |
| U8555 | 2.60 | 2.40 | 2.54 | 2.56 | 2.52 | 2.90 | 3.09 | 2.57 | 2.56 |
| U8558 | 2.30 | 2.20 | 2.26 | 2.16 | 2.15 | 2.30 | 2.33 | 2.31 | 2.35 |
| U8559 | 1.60 | 1.40 | 1.45 | 1.42 | 1.24 | 1.60 | 1.65 | 1.45 | 1.28 |
| U8563 | 2.20 | 2.30 | 2.30 | 2.32 | 2.30 | 2.40 | 2.43 | 2.34 | 2.42 |
| U8570 | 1.20 | 1.20 | 1.20 | 1.34 | 1.23 | 1.20 | 1.21 | 1.35 | 1.25 |
| U8575 | 0.90 | 0.80 | 0.84 | 0.96 | 0.80 | 0.90 | 0.89 | 0.95 | 0.78 |
| U9031 | 2.10 | 2.40 | 2.33 | 2.42 | 2.42 | 2.60 | 2.38 | 2.34 | 2.35 |
| U9032 | 1.70 | 1.70 | 1.75 | 1.78 | 1.58 | 1.90 | 1.93 | 1.68 | 1.53 |
| U9034 | 3.00 | 2.90 | 2.82 | 3.79 | 3.97 | 3.40 | 3.37 | 3.49 | 3.80 |
| U9039 | 2.70 | 3.00 | 3.17 | 2.99 | 3.03 | 3.20 | 3.20 | 3.12 | 3.27 |
| U9040 | 1.40 | 1.40 | 1.44 | 1.36 | 1.20 | 1.40 | 1.39 | 1.33 | 1.15 |
| U9049 | 3.50 | 3.30 | 3.46 | 3.33 | 3.45 | 3.60 | 3.77 | 3.33 | 3.72 |
| U9055 | 2.40 | 2.10 | 2.14 | 2.15 | 2.04 | 2.40 | 2.39 | 2.15 | 2.13 |

A statistical comparison of the above data from Table 2 is presented below in Tables 4 and 5. The value AINR in Table 2 represents the INR value obtained pursuant to the World Health Organization (WHO), using expressions (A) and (B) above. GINR and MINR correspond to INR values used to determine the comparison data set forth in Tables 4 and 5.

The determination of the new anticoagulant therapy factor (ATFt) may be carried out with a computer. According to one example, the gathering, storing, and manipulation of the data generally illustrated in FIG. 4, may be accomplished by computer 30 of FIG. 1 that receives digital voltage values converted, by the A/D converter 26, from analog voltage quantities of the photocell 10 detection means.

In accordance with one embodiment, the IBM-compatible computer 30 of FIG. 1 stores and manipulates these digital values corresponding to related data of FIG. 4 and may be programmed as follows:

(a) a sample of blood where the plasma is available, such as, for example, a sample of citrated blood, is obtained and placed in an appropriate container, the computer 30, as well as the recorder 28, sequentially records voltage values for a few seconds before injection of thromboplastin. As previously discussed, thromboplastin (tissue factor) is one of the factors in the human body that causes blood to clot. Prothrombin is another. Fibrinogen is yet another. Before injection of the thromboplastin, the output from the A/D converter 26 is relatively constant. When thromboplastin is injected into the plasma sample in the container, a significant and abrupt change occurs in the recorded voltage values of both the computer 30 and the recorder 28. This abrupt change is recognized by both the recorder 28 and, more importantly, by the computer 30 which uses such recognition to establish $T_0$. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed with reference to FIG. 3;

(b) the computer 30 may be programmed to look for a digital quantity representative of a critical quantity $c_1$, and when such occurs, record its instant time $T_1$. (The time span between $T_0$ and $T_1$ is the prothrombin time (PT), and has an normal duration of about 12 seconds, but may be greater than 30 seconds);

(c) following the detection of the quantity $c_1$, the computer 30 may be programmed to detect for the acceleration of fibrinogen (FBG) to fibrin conversion. The computer 30 is programmed to detect the maximum acceleration quantity $c_{MAP}$ or $c_{T2}$ as illustrated in FIG. 3, and its corresponding time of occurrence $t_{MAP}$, which is $T_2$ in FIG. 3.

(d) the computer detects a quantity $c_{EOT}$ occurring at time $t_{EOT}$. Typically; it is important that the rate of fibrin formation increase for at least 1.5 seconds following the occurrence of ($T_1$); the computer determines a theoretical end of test (TEOT) based on the determination of the zero order kinetic rate. The computer may be programmed to determine the zero order rate, which is expressed as a Line (L) in FIG. 4. The TEOT may be determined by the corresponding time value (TEOT) along the line L which corresponds with the quantity $c_{EOT}$ (i.e., that quantity corresponding to the time, $T_3$).

(e) following the detection of the maximum acceleration quantity $c_{T2}$ (also representing $c_{MAP}$) and the time $T_2$ (also representing $t_{MAP}$) both of which define the maximum acceleration point (MAP), and the TEOT, the computer is programmed to determine a new fibrinogen transformation rate (nFTR) covering a predetermined range starting prior to the maximum acceleration point (MAP) and ending after the maximum acceleration point (MAP). The elapsed time from $T_0$ to $T_2$ (which is $t_{MAP}$) is the time to maximum acceleration (TMA), shown in FIG. 4, and is represented by TX (i.e., time to MAP);

The new fibrinogen transformation rate (nFTR) has an upwardly rising (increasing quantities) slope prior to the maximum acceleration point (MAP) and, conversely, has a downwardly falling (decreasing quantities) slope after the maximum acceleration point (MAP).

The computer 30 is programmed to ascertain the value for the time to start ($T_2S$) which corresponds with the time at which the simulated zero order kinetic rate begins.

(f) following the detection of the acceleration of fibrinogen conversion to detect the start time $T_2S$, the computer 30 is programmed to detect for a deceleration of the fibrinogen conversion, wherein the fibrinogen concentration decreases from a predetermined quantity $c_{MAP}$ to a predetermined quantity $c_{EOT}$ having a value which is about equal but less than the first quantity $c_1$. The computer is programmed to ascertain a first delta (IUTz), by determining the difference between the quantity $c_{T2S}$ and the quantity $c_{EOT}$; and a second delta (IUXz) by determining the difference between the quantity $c_{T2S}$ and the quantity $c_{2\ (or\ CMAP)}$; the computer also determines the value ZTM by determining the difference between the time $T_2$ (which is Tmap) and the time $T_2S$;

(g) the computer 30 manipulates the collected data of (a); (b); (c); (d), (e) and (f) above, to determine the new fibrinogen transfer rate (nFTR). The nFTR may be arrived at based on the principle that if a required amount (e.g., 0.05 g/l) of fibrinogen concentration $c_1$ is first necessary to detect a clot point ($t_1$); then when the fibrinogen concentration ($c_{EOT}$) becomes less than the required amount $c_1$, which occurs at time ($t_{EOT}$), the fibrinogen end point has been reached. More particularly, the required fibrinogen concentration $c_1$ is the starting point of fibrinogen conversion of the clotting process and the less than required fibrinogen concentration $c_{EOT}$ is the end point of the fibrinogen conversion of the clotting process.

(h) the duration of the fibrinogen conversion of the clotting process of the present invention is defined by the zero order time period between TEOT and $T_2S$ and is generally indicated in FIG. 3 as IUTz. The difference between the corresponding concentrations $c_{T2S}$ and cT2 is used to define a delta IUXz. The computer now has the information needed to determine the TEOT, which is expressed by the following formula:

$$TEOT = ZTM/IUXz * IUTz \quad (5)$$

The value TEOT may be assigned VALUE 1;

(i) data collected is manipulated by the computer 30 to calculate a second value, VALUE 2, using $T_2S$ and a multiplier M (which in this example, in expression 7 below, is a fraction). The computer may be programmed to use as a multiplier a value based on the natural log base "e" (which is 2.71828), scaled by a scaling value. Here, the scaling value is 100, and the multiplier may be expressed as follows:

$$M = 100e \quad (9)$$

VALUE 2 is determined using the information which the computer has ascertained and stored, by the following expression:

$$VALUE\ 2 = T2S/100e \quad (7)$$

The data may be ascertained and stored in the computer for reference.

(j) the computer 30 now has the information needed to determine the nATFt, which typically is expressed as:

$$nATFt = VALUE\ 1 * VALUE\ 2 \quad (4)$$

The computer 30 may be used to manipulate and derive the quantities of expression (4) to determine a new anticoagulant therapy factor nATFt utilizing known programming routines and techniques. The data collected by a computer 30 may be used to manipulate and derive the new anticoagulant therapy factor (nATFt) of expression (4). Similarly, one skilled in the art, using known mathematical techniques may derive the theoretical end of test TEOT of expression (5) and the second value VALUE 2 of expression (7) which, in turn, are used to determine the new anticoagulant therapy (nATFt) of expression (4). In the nATFt determination, the determination is based on the patient's own sample, and does not rely on the determination of normal prothrombin times for the reagent used (e.g., thromboplastin, innovin or the like). With the nATFt, no longer does the accuracy of the quantities determined depend, in whole or part, on the number of specimens used, that is, the number of stable (or presumed stable) patients.

The new anticoagulation therapy factor (nATFt) does not require an ISI value, as was previously used to determine anticoagulation therapy factors. The new anticoagulation therapy factor (nATFt) uses for its ascertainment the values extracted from the clotting curve (see FIG. 4), in particular $T_2S$, Tmap, TEOT, $c_{T2S}$, cmap and ceot. In determining the new anticoagulant therapy factor (nATFt), the ISI is not required, nor is the MNPT, or the need to obtain and calculate the prothrombin times (PT's) for 20 presumed normal patients. In carrying out coagulation studies, the new anticoagulant therapy factor (nATFt) may replace INR in anticoagulant therapy management. In addition, using the sample from the patient, the computer 30 has knowledge of the values obtained for the fibrinogen reaction, to ascertain the (nATFt).

It should now be appreciated that the present invention provides an apparatus and method for obtaining a new anticoagulant therapy factor (nATF) without encountering the complications involved with obtaining the prior art quantities International Normalized Ratio (INR) and International Sensitivity Index (ISI).

The new anticoagulant therapy factor (nATFt) preferably is a replacement for the International Normalized Ratio (INR). Existing medical literature, instrumentation, and methodologies are closely linked to the International Normalized Ratio (INR). The nATFt was compared for correlation with the INR by comparative testing, to INR quantities, even with the understanding that the INR determination may have an error of about +/−15%, at a 95% confidence interval, which needs to be taken into account to explain certain inconsistencies.

The hereinbefore description of the new anticoagulant therapy factor (nATFt) does correlate at least as well as, and preferably better than, studies carried out using the International Normalized Ratio (INR). For some comparisons, see the tables below, and in particular Table 4 and Table 5.

Table 3 (Part A) and Table 3 (Part B) provide corresponding data for a coagulation study. In Table 3 (Part A and B), the following references are used:

| Column | Label | Definition |
|---|---|---|
| A | ID | Sample ID |
| B | OD@$T_2$S | OD at the start of Zero Order Kinetic |
| C | OD@Map | OD at the Maximum Acceleration Point (MAP) |
| D | OD@Eot | OD at the END OF TEST (Eot) |
| E | $\Delta T_2$SMap | Delta of Column B and C creating the IUXz |
| F | $\Delta T_2$SEot | Delta of Column B and D creating the IUTz |
| G | FTR od | Ratio of Column E divided by F The FTR od is subtracted from 2 creating the Exponent that replaces the ISI |
| H | Time@$T_2$S | Time at the start of Zero Order Kinetics |
| I | Time@Map | Time at the Maximum Acceleration Point (MAP) |
| J | Time@TEot | Time at the Theoretical End of Test (TEOT) |
| K | $\Delta T_2$SMap | Delta of Column H and I creating the IUXz (and ZTM) |
| L | $\Delta T_2$STEot | Delta of Column H and J creating the IUTz |
| M | FTR Time | Ration of Column K divided by L |

TABLE 3

(Part A)

| ID | OD@T2S | OD@Map | OD@Eot | ΔT2SMap | ΔT2SEot |
|---|---|---|---|---|---|
| A001 | 3719 | 3707 | 3664 | 12 | 55 |
| A002 | 3713 | 3704 | 3686 | 9 | 27 |
| A003 | 3729 | 3720 | 3705 | 9 | 24 |
| A004 | 3708 | 3696 | 3663 | 12 | 45 |
| A005 | 3727 | 3715 | 3700 | 12 | 27 |
| A007 | 3725 | 3718 | 3698 | 7 | 27 |
| A008 | 3714 | 3693 | 3646 | 21 | 68 |
| A009 | 3727 | 3716 | 3697 | 11 | 30 |
| A010 | 3727 | 3714 | 3701 | 13 | 26 |

TABLE 3-continued (Part A)

| ID | OD@T2S | OD@Map | OD@Eot | ΔT2SMap | ΔT2SEot |
|---|---|---|---|---|---|
| A011 | 3690 | 3676 | 3647 | 14 | 43 |
| A012 | 3728 | 3716 | 3695 | 12 | 33 |
| A013 | 3715 | 3690 | 3641 | 25 | 74 |
| A014 | 3717 | 3708 | 3694 | 9 | 23 |
| A015 | 3726 | 3718 | 3706 | 8 | 20 |
| A016 | 3722 | 3715 | 3678 | 7 | 44 |
| A017 | 3720 | 3707 | 3681 | 13 | 39 |
| A018 | 3723 | 3709 | 3697 | 14 | 26 |
| A019 | 3716 | 3695 | 3653 | 21 | 63 |
| A020 | 3727 | 3716 | 3698 | 11 | 29 |
| A021 | 3727 | 3720 | 3694 | 7 | 33 |
| A022 | 3717 | 3700 | 3667 | 17 | 50 |
| A023 | 3719 | 3706 | 3663 | 13 | 56 |
| A024 | 3717 | 3702 | 3661 | 15 | 56 |
| A025 | 3731 | 3727 | 3716 | 4 | 15 |
| A026 | 3717 | 3705 | 3673 | 12 | 44 |
| A027 | 3714 | 3698 | 3667 | 16 | 47 |
| A028 | 3713 | 3696 | 3651 | 17 | 62 |
| A029 | 3712 | 3691 | 3647 | 21 | 65 |
| A030 | 3716 | 3695 | 3635 | 21 | 81 |
| A031 | 3715 | 3704 | 3687 | 11 | 28 |
| A032 | 3716 | 3710 | 3675 | 6 | 41 |
| A033 | 3718 | 3704 | 3671 | 14 | 47 |
| A034 | 3721 | 3705 | 3674 | 16 | 47 |
| A035 | 3723 | 3715 | 3699 | 8 | 24 |
| A036 | 3722 | 3710 | 3681 | 12 | 41 |
| A037 | 3715 | 3700 | 3669 | 15 | 46 |
| A038 | 3722 | 3707 | 3686 | 15 | 36 |
| A039 | 3721 | 3712 | 3698 | 9 | 23 |
| A040 | 3720 | 3706 | 3664 | 14 | 56 |
| A041 | 3711 | 3695 | 3638 | 16 | 73 |
| A042 | 3722 | 3709 | 3687 | 13 | 35 |
| A044 | 3723 | 3709 | 3683 | 14 | 40 |
| A045 | 3712 | 3697 | 3647 | 15 | 65 |
| A047 | 3716 | 3697 | 3668 | 19 | 48 |
| A048 | 3720 | 3708 | 3682 | 12 | 38 |
| A049 | 3725 | 3711 | 3690 | 14 | 35 |
| A050 | 3724 | 3712 | 3685 | 12 | 39 |
| A051 | 3705 | 3688 | 3634 | 17 | 71 |
| A052 | 3725 | 3714 | 3687 | 11 | 38 |
| A053 | 3724 | 3717 | 3696 | 7 | 28 |
| A054 | 3715 | 3701 | 3679 | 14 | 36 |
| A055 | 3718 | 3684 | 3627 | 34 | 91 |
| A056 | 3710 | 3689 | 3624 | 21 | 86 |
| A057 | 3709 | 3701 | 3683 | 8 | 26 |
| A058 | 3725 | 3710 | 3669 | 15 | 56 |
| A059 | 3722 | 3712 | 3696 | 10 | 26 |
| A060 | 3719 | 3712 | 3698 | 7 | 21 |
| A061 | 3720 | 3708 | 3680 | 12 | 40 |
| A062 | 3719 | 3701 | 3651 | 18 | 68 |
| A063 | 3728 | 3715 | 3697 | 13 | 31 |
| A064 | 3718 | 3707 | 3685 | 11 | 33 |
| A065 | 3721 | 3704 | 3680 | 17 | 41 |
| A066 | 3727 | 3717 | 3707 | 10 | 20 |
| A067 | 3708 | 3689 | 3641 | 19 | 67 |
| A068 | 3726 | 3712 | 3686 | 14 | 40 |
| A069 | 3719 | 3715 | 3695 | 4 | 24 |
| A070 | 3716 | 3705 | 3671 | 11 | 45 |
| A071 | 3714 | 3696 | 3660 | 18 | 54 |
| A072 | 3713 | 3693 | 3646 | 20 | 67 |
| A073 | 3707 | 3686 | 3639 | 21 | 68 |
| A074 | 3699 | 3684 | 3665 | 15 | 34 |
| A075 | 3734 | 3730 | 3726 | 4 | 8 |
| A076 | 3719 | 3704 | 3665 | 15 | 54 |
| A077 | 3718 | 3694 | 3634 | 24 | 84 |
| A078 | 3723 | 3707 | 3684 | 16 | 39 |
| A080 | 3729 | 3712 | 3637 | 17 | 92 |
| A081 | 3710 | 3694 | 3626 | 16 | 84 |
| A082 | 3716 | 3703 | 3654 | 13 | 62 |
| A083 | 3720 | 3710 | 3686 | 10 | 34 |
| A084 | 3731 | 3721 | 3667 | 10 | 64 |
| A085 | 3727 | 3704 | 3675 | 23 | 52 |
| A086 | 3717 | 3699 | 3650 | 18 | 67 |
| A087 | 3715 | 3694 | 3654 | 21 | 61 |
| A088 | 3704 | 3681 | 3630 | 23 | 74 |

TABLE 3-continued (Part A)

| ID | OD@T2S | OD@Map | OD@Eot | ΔT2SMap | ΔT2SEot |
|---|---|---|---|---|---|
| A089 | 3723 | 3714 | 3687 | 9 | 36 |
| A090 | 3714 | 3685 | 3588 | 29 | 126 |
| A091 | 3724 | 3710 | 3659 | 14 | 65 |
| A092 | 3696 | 3657 | 3582 | 39 | 114 |
| A093 | 3730 | 3716 | 3693 | 14 | 37 |
| A094 | 3720 | 3708 | 3676 | 12 | 44 |
| A095 | 3710 | 3689 | 3638 | 21 | 72 |
| A096 | 3725 | 3717 | 3700 | 8 | 25 |
| A097 | 3721 | 3713 | 3692 | 8 | 29 |
| A098 | 3716 | 3696 | 3659 | 20 | 57 |
| A099 | 3720 | 3712 | 3685 | 8 | 35 |
| A100 | 3709 | 3685 | 3625 | 24 | 84 |
| A101 | 3727 | 3715 | 3690 | 12 | 37 |
| A102 | 3722 | 3708 | 3661 | 14 | 61 |
| A103 | 3714 | 3693 | 3640 | 21 | 74 |
| A104 | 3719 | 3705 | 3682 | 14 | 37 |
| A105 | 3725 | 3706 | 3660 | 19 | 65 |
| A107 | 3720 | 3707 | 3660 | 13 | 60 |
| A108 | 3731 | 3723 | 3709 | 8 | 22 |
| A109 | 3727 | 3711 | 3689 | 16 | 38 |
| A110 | 3719 | 3693 | 3635 | 26 | 84 |
| A111 | 3723 | 3701 | 3667 | 22 | 56 |
| A112 | 3714 | 3695 | 3614 | 19 | 100 |
| A113 | 3717 | 3702 | 3664 | 15 | 53 |
| A114 | 3711 | 3687 | 3655 | 24 | 56 |
| A115 | 3716 | 3697 | 3652 | 19 | 64 |
| A116 | 3726 | 3717 | 3698 | 9 | 28 |
| A117 | 3710 | 3688 | 3630 | 22 | 80 |
| A118 | 3729 | 3721 | 3699 | 8 | 30 |
| A119 | 3729 | 3716 | 3679 | 13 | 50 |
| A120 | 3722 | 3713 | 3688 | 9 | 34 |
| A121 | 3730 | 3722 | 3704 | 8 | 26 |
| A122 | 3713 | 3688 | 3650 | 25 | 63 |
| A123 | 3729 | 3721 | 3704 | 8 | 25 |
| A124 | 3721 | 3712 | 3696 | 9 | 25 |
| A125 | 3683 | 3668 | 3600 | 15 | 83 |
| A126 | 3736 | 3723 | 3714 | 13 | 22 |
| A127 | 3715 | 3703 | 3640 | 12 | 75 |
| A128 | 3723 | 3714 | 3682 | 9 | 41 |
| A129 | 3728 | 3715 | 3677 | 13 | 51 |
| A130 | 3715 | 3700 | 3656 | 15 | 59 |
| A131 | 3723 | 3711 | 3690 | 12 | 33 |
| A132 | 3720 | 3700 | 3665 | 20 | 55 |
| A133 | 3728 | 3706 | 3673 | 22 | 55 |
| A134 | 3725 | 3696 | 3667 | 29 | 58 |
| A135 | 3717 | 3703 | 3676 | 14 | 41 |
| A136 | 3725 | 3712 | 3659 | 13 | 66 |
| A137 | 3712 | 3691 | 3662 | 21 | 50 |
| A138 | 3714 | 3691 | 3641 | 23 | 73 |
| A139 | 3717 | 3700 | 3642 | 17 | 75 |
| A140 | 3710 | 3690 | 3642 | 20 | 68 |
| A141 | 3715 | 3698 | 3661 | 17 | 54 |
| A142 | 3729 | 3719 | 3706 | 10 | 23 |
| A143 | 3726 | 3709 | 3693 | 17 | 33 |
| A144 | 3709 | 3693 | 3641 | 16 | 68 |
| A145 | 3704 | 3688 | 3639 | 16 | 65 |
| A146 | 3718 | 3706 | 3664 | 12 | 54 |
| A147 | 3713 | 3698 | 3661 | 15 | 52 |
| A148 | 3714 | 3701 | 3646 | 13 | 68 |
| A149 | 3711 | 3692 | 3653 | 19 | 58 |
| A150 | 3701 | 3678 | 3608 | 23 | 93 |
| A151 | 3701 | 3668 | 3587 | 33 | 114 |
| A152 | 3717 | 3706 | 3683 | 11 | 34 |
| A153 | 3691 | 3669 | 3596 | 22 | 95 |
| A154 | 3706 | 3690 | 3645 | 16 | 61 |
| A155 | 3724 | 3703 | 3667 | 21 | 57 |
| A156 | 3717 | 3711 | 3688 | 6 | 29 |
| A157 | 3717 | 3702 | 3678 | 15 | 39 |
| A158 | 3723 | 3715 | 3689 | 8 | 34 |
| A159 | 3714 | 3696 | 3652 | 18 | 62 |
| A160 | 3717 | 3690 | 3655 | 27 | 62 |
| A161 | 3720 | 3713 | 3676 | 7 | 44 |
| A162 | 3722 | 3706 | 3653 | 16 | 69 |
| A163 | 3725 | 3715 | 3683 | 10 | 42 |
| A164 | 3721 | 3712 | 3685 | 9 | 36 |
| A165 | 3707 | 3693 | 3636 | 14 | 71 |
| A166 | 3704 | 3683 | 3631 | 21 | 73 |
| A167 | 3718 | 3712 | 3690 | 6 | 28 |
| A168 | 3722 | 3700 | 3669 | 22 | 53 |
| A169 | 3705 | 3694 | 3624 | 11 | 81 |
| A170 | 3717 | 3704 | 3680 | 13 | 37 |
| A171 | 3721 | 3699 | 3666 | 22 | 55 |
| A172 | 3726 | 3719 | 3691 | 7 | 35 |
| A173 | 3718 | 3708 | 3680 | 10 | 38 |
| A174 | 3707 | 3692 | 3648 | 15 | 59 |
| A175 | 3689 | 3671 | 3642 | 18 | 47 |
| A176 | 3724 | 3711 | 3671 | 13 | 53 |
| A177 | 3721 | 3710 | 3689 | 11 | 32 |
| A178 | 3716 | 3700 | 3655 | 16 | 61 |
| A179 | 3717 | 3707 | 3672 | 10 | 45 |
| A180 | 3718 | 3706 | 3686 | 12 | 32 |
| A181 | 3722 | 3703 | 3676 | 19 | 46 |
| A182 | 3716 | 3706 | 3667 | 10 | 49 |
| A183 | 3711 | 3703 | 3689 | 8 | 22 |
| A184 | 3717 | 3705 | 3661 | 12 | 56 |
| A185 | 3711 | 3694 | 3639 | 17 | 72 |
| A186 | 3721 | 3675 | 3620 | 46 | 101 |
| A187 | 3715 | 3704 | 3668 | 11 | 47 |
| A188 | 3717 | 3703 | 3672 | 14 | 45 |
| A189 | 3709 | 3689 | 3658 | 20 | 51 |
| A190 | 3718 | 3709 | 3688 | 9 | 30 |
| A191 | 3725 | 3717 | 3696 | 8 | 29 |
| A192 | 3722 | 3714 | 3691 | 8 | 31 |
| A193 | 3727 | 3718 | 3685 | 9 | 42 |
| A194 | 3720 | 3710 | 3688 | 10 | 32 |
| A195 | 3691 | 3667 | 3589 | 24 | 102 |
| A196 | 3718 | 3707 | 3673 | 11 | 45 |
| A197 | 3706 | 3692 | 3637 | 14 | 69 |
| A198 | 3717 | 3707 | 3692 | 10 | 25 |
| A199 | 3720 | 3705 | 3684 | 15 | 36 |
| A200 | 3718 | 3709 | 3686 | 9 | 32 |
| A201 | 3725 | 3713 | 3681 | 12 | 44 |
| A202 | 3723 | 3713 | 3694 | 10 | 29 |
| A203 | 3715 | 3704 | 3670 | 11 | 45 |
| A204 | 3723 | 3713 | 3697 | 10 | 26 |
| A205 | 3717 | 3706 | 3674 | 11 | 43 |
| A207 | 3710 | 3702 | 3668 | 8 | 42 |
| A208 | 3722 | 3708 | 3680 | 14 | 42 |
| A209 | 3725 | 3709 | 3682 | 16 | 43 |
| A210 | 3724 | 3714 | 3688 | 10 | 36 |
| A211 | 3712 | 3694 | 3637 | 18 | 75 |
| A212 | 3727 | 3711 | 3689 | 16 | 38 |
| A213 | 3724 | 3705 | 3652 | 19 | 72 |
| A214 | 3727 | 3715 | 3687 | 12 | 40 |
| A215 | 3715 | 3703 | 3668 | 12 | 47 |
| A216 | 3722 | 3707 | 3667 | 15 | 55 |
| A217 | 3716 | 3695 | 3630 | 21 | 86 |
| A218 | 3699 | 3665 | 3583 | 34 | 116 |
| A219 | 3727 | 3716 | 3699 | 11 | 28 |
| A220 | 3717 | 3704 | 3674 | 13 | 43 |
| A222 | 3713 | 3704 | 3684 | 9 | 29 |
| A223 | 3724 | 3715 | 3695 | 9 | 29 |
| A224 | 3718 | 3703 | 3676 | 15 | 42 |
| A225 | 3721 | 3707 | 3683 | 14 | 38 |

TABLE 3

(Part B)

| ID | FTR od | Time@T2S | Time@Map | Time@TEot | ΔT2SMap | ΔT2STEot | FTR time | FTR od |
|---|---|---|---|---|---|---|---|---|
| A001 | 0.218 | 2211 | 2366 | 2921 | 155 | 710 | 0.218 | 0.218 |
| A002 | 0.333 | 2279 | 2464 | 2834 | 185 | 555 | 0.333 | 0.333 |
| A003 | 0.375 | 2329 | 2523 | 2846 | 194 | 517 | 0.375 | 0.375 |
| A004 | 0.267 | 1975 | 2107 | 2470 | 132 | 495 | 0.267 | 0.267 |
| A005 | 0.444 | 2166 | 2387 | 2663 | 221 | 497 | 0.444 | 0.444 |
| A007 | 0.259 | 1838 | 1931 | 2197 | 93 | 359 | 0.259 | 0.259 |
| A008 | 0.309 | 2160 | 2369 | 2837 | 209 | 677 | 0.309 | 0.309 |
| A009 | 0.367 | 2391 | 2598 | 2956 | 207 | 565 | 0.367 | 0.367 |
| A010 | 0.500 | 1716 | 1925 | 2134 | 209 | 418 | 0.500 | 0.500 |
| A011 | 0.326 | 1788 | 1935 | 2240 | 147 | 452 | 0.326 | 0.326 |
| A012 | 0.364 | 2233 | 2428 | 2769 | 195 | 536 | 0.364 | 0.364 |
| A013 | 0.338 | 2409 | 2667 | 3173 | 258 | 764 | 0.338 | 0.338 |
| A014 | 0.391 | 1701 | 1836 | 2046 | 135 | 345 | 0.391 | 0.391 |
| A015 | 0.400 | 1715 | 1877 | 2120 | 162 | 405 | 0.400 | 0.400 |
| A016 | 0.159 | 2233 | 2336 | 2880 | 103 | 647 | 0.159 | 0.159 |
| A017 | 0.333 | 1728 | 1882 | 2190 | 154 | 462 | 0.333 | 0.333 |
| A018 | 0.538 | 1862 | 2175 | 2443 | 313 | 581 | 0.538 | 0.538 |
| A019 | 0.333 | 1756 | 1927 | 2269 | 171 | 513 | 0.333 | 0.333 |
| A020 | 0.379 | 2535 | 2761 | 3131 | 226 | 596 | 0.379 | 0.379 |
| A021 | 0.212 | 2151 | 2283 | 2773 | 132 | 622 | 0.212 | 0.212 |
| A022 | 0.340 | 1900 | 2089 | 2456 | 189 | 556 | 0.340 | 0.340 |
| A023 | 0.232 | 2251 | 2384 | 2824 | 133 | 573 | 0.232 | 0.232 |
| A024 | 0.268 | 2522 | 2676 | 3097 | 154 | 575 | 0.268 | 0.268 |
| A025 | 0.267 | 1708 | 1775 | 1959 | 67 | 251 | 0.267 | 0.267 |
| A026 | 0.273 | 1611 | 1730 | 2047 | 119 | 436 | 0.273 | 0.273 |
| A027 | 0.340 | 1537 | 1689 | 1984 | 152 | 447 | 0.340 | 0.340 |
| A028 | 0.274 | 1780 | 1927 | 2316 | 147 | 536 | 0.274 | 0.274 |
| A029 | 0.323 | 1839 | 2023 | 2409 | 184 | 570 | 0.323 | 0.323 |
| A030 | 0.259 | 2051 | 2245 | 2799 | 194 | 748 | 0.259 | 0.259 |
| A031 | 0.393 | 2107 | 2321 | 2652 | 214 | 545 | 0.393 | 0.393 |
| A032 | 0.146 | 2584 | 2678 | 3226 | 94 | 642 | 0.146 | 0.146 |
| A033 | 0.298 | 2251 | 2426 | 2839 | 175 | 588 | 0.298 | 0.298 |
| A034 | 0.340 | 1909 | 2107 | 2491 | 198 | 582 | 0.340 | 0.340 |
| A035 | 0.333 | 3037 | 3305 | 3841 | 268 | 804 | 0.333 | 0.333 |
| A036 | 0.293 | 2211 | 2417 | 2915 | 206 | 704 | 0.293 | 0.293 |
| A037 | 0.326 | 2173 | 2335 | 2670 | 162 | 497 | 0.326 | 0.326 |
| A038 | 0.417 | 1543 | 1713 | 1951 | 170 | 408 | 0.417 | 0.417 |
| A039 | 0.391 | 1572 | 1721 | 1953 | 149 | 381 | 0.391 | 0.391 |
| A040 | 0.250 | 1959 | 2119 | 2599 | 160 | 640 | 0.250 | 0.250 |
| A041 | 0.219 | 1993 | 2144 | 2682 | 151 | 689 | 0.219 | 0.219 |
| A042 | 0.371 | 2660 | 2929 | 3384 | 269 | 724 | 0.371 | 0.371 |
| A044 | 0.350 | 2657 | 2858 | 3231 | 201 | 574 | 0.350 | 0.350 |
| A045 | 0.231 | 2175 | 2325 | 2825 | 150 | 650 | 0.231 | 0.231 |
| A047 | 0.396 | 2197 | 2458 | 2856 | 261 | 659 | 0.396 | 0.396 |
| A048 | 0.316 | 2535 | 2783 | 3320 | 248 | 785 | 0.316 | 0.316 |
| A049 | 0.400 | 2004 | 2256 | 2634 | 252 | 630 | 0.400 | 0.400 |
| A050 | 0.308 | 2193 | 2403 | 2876 | 210 | 683 | 0.308 | 0.308 |
| A051 | 0.239 | 1745 | 1867 | 2255 | 122 | 510 | 0.239 | 0.239 |
| A052 | 0.289 | 2073 | 2247 | 2674 | 174 | 601 | 0.289 | 0.289 |
| A053 | 0.250 | 2239 | 2353 | 2695 | 114 | 456 | 0.250 | 0.250 |
| A054 | 0.389 | 1816 | 2005 | 2302 | 189 | 486 | 0.389 | 0.389 |
| A055 | 0.374 | 3127 | 3668 | 4575 | 541 | 1448 | 0.374 | 0.374 |
| A056 | 0.244 | 2538 | 2728 | 3316 | 190 | 778 | 0.244 | 0.244 |
| A057 | 0.308 | 2125 | 2263 | 2574 | 138 | 449 | 0.308 | 0.308 |
| A058 | 0.268 | 4120 | 4529 | 5647 | 409 | 1527 | 0.268 | 0.268 |
| A059 | 0.385 | 2164 | 2358 | 2668 | 194 | 504 | 0.385 | 0.385 |
| A060 | 0.333 | 2325 | 2494 | 2832 | 169 | 507 | 0.333 | 0.333 |
| A061 | 0.300 | 2006 | 2205 | 2669 | 199 | 663 | 0.300 | 0.300 |
| A062 | 0.265 | 3718 | 4058 | 5002 | 340 | 1284 | 0.265 | 0.265 |
| A063 | 0.419 | 2231 | 2584 | 3073 | 353 | 842 | 0.419 | 0.419 |
| A064 | 0.333 | 1926 | 2076 | 2376 | 150 | 450 | 0.333 | 0.333 |
| A065 | 0.415 | 2225 | 2494 | 2874 | 269 | 649 | 0.415 | 0.415 |
| A066 | 0.500 | 1761 | 1968 | 2175 | 207 | 414 | 0.500 | 0.500 |
| A067 | 0.284 | 1701 | 1852 | 2233 | 151 | 532 | 0.284 | 0.284 |
| A068 | 0.350 | 1979 | 2215 | 2653 | 236 | 674 | 0.350 | 0.350 |
| A069 | 0.167 | 1935 | 1998 | 2313 | 63 | 378 | 0.167 | 0.167 |
| A070 | 0.244 | 1939 | 2063 | 2446 | 124 | 507 | 0.244 | 0.244 |
| A071 | 0.333 | 1762 | 1950 | 2326 | 188 | 564 | 0.333 | 0.333 |
| A072 | 0.299 | 1723 | 1912 | 2356 | 189 | 633 | 0.299 | 0.299 |
| A073 | 0.309 | 1614 | 1774 | 2132 | 160 | 518 | 0.309 | 0.309 |
| A074 | 0.441 | 1698 | 1884 | 2120 | 186 | 422 | 0.441 | 0.441 |
| A075 | 0.500 | 1489 | 1620 | 1751 | 131 | 262 | 0.500 | 0.500 |
| A076 | 0.278 | 1529 | 1684 | 2087 | 155 | 558 | 0.278 | 0.278 |
| A077 | 0.286 | 2845 | 3154 | 3927 | 309 | 1082 | 0.286 | 0.286 |
| A078 | 0.410 | 1867 | 2081 | 2389 | 214 | 522 | 0.410 | 0.410 |

TABLE 3-continued (Part B)

| ID | FTR od | Time@T2S | Time@Map | Time@TEot | ΔT2SMap | ΔT2STEot | FTR time | FTR od |
|---|---|---|---|---|---|---|---|---|
| A080 | 0.185 | 3548 | 3924 | 5583 | 376 | 2035 | 0.185 | 0.185 |
| A081 | 0.190 | 2698 | 2853 | 3512 | 155 | 814 | 0.190 | 0.190 |
| A082 | 0.210 | 1625 | 1744 | 2193 | 119 | 568 | 0.210 | 0.210 |
| A083 | 0.294 | 1583 | 1692 | 1954 | 109 | 371 | 0.294 | 0.294 |
| A084 | 0.156 | 3394 | 3647 | 5013 | 253 | 1619 | 0.156 | 0.156 |
| A085 | 0.442 | 2416 | 2867 | 3436 | 451 | 1020 | 0.442 | 0.442 |
| A086 | 0.269 | 2111 | 2293 | 2788 | 182 | 677 | 0.269 | 0.269 |
| A087 | 0.344 | 1740 | 1924 | 2274 | 184 | 534 | 0.344 | 0.344 |
| A088 | 0.311 | 1715 | 1881 | 2249 | 166 | 534 | 0.311 | 0.311 |
| A089 | 0.250 | 1876 | 1981 | 2296 | 105 | 420 | 0.250 | 0.250 |
| A090 | 0.230 | 3411 | 3775 | 4993 | 364 | 1582 | 0.230 | 0.230 |
| A091 | 0.215 | 3897 | 4201 | 5308 | 304 | 1411 | 0.215 | 0.215 |
| A092 | 0.342 | 1906 | 2151 | 2622 | 245 | 716 | 0.342 | 0.342 |
| A093 | 0.378 | 2821 | 3197 | 3815 | 376 | 994 | 0.378 | 0.378 |
| A094 | 0.273 | 2447 | 2600 | 3008 | 153 | 561 | 0.273 | 0.273 |
| A095 | 0.292 | 1573 | 1726 | 2098 | 153 | 525 | 0.292 | 0.292 |
| A096 | 0.320 | 1784 | 1913 | 2187 | 129 | 403 | 0.320 | 0.320 |
| A097 | 0.276 | 1374 | 1479 | 1755 | 105 | 381 | 0.276 | 0.276 |
| A098 | 0.351 | 1480 | 1655 | 1979 | 175 | 499 | 0.351 | 0.351 |
| A099 | 0.229 | 1679 | 1770 | 2077 | 91 | 398 | 0.229 | 0.229 |
| A100 | 0.286 | 1538 | 1705 | 2123 | 167 | 585 | 0.286 | 0.286 |
| A101 | 0.324 | 2137 | 2344 | 2775 | 207 | 638 | 0.324 | 0.324 |
| A102 | 0.230 | 2473 | 2657 | 3275 | 184 | 802 | 0.230 | 0.230 |
| A103 | 0.284 | 1868 | 2069 | 2576 | 201 | 708 | 0.284 | 0.284 |
| A104 | 0.378 | 2344 | 2732 | 3369 | 388 | 1025 | 0.378 | 0.378 |
| A105 | 0.292 | 2427 | 2750 | 3532 | 323 | 1105 | 0.292 | 0.292 |
| A107 | 0.217 | 2140 | 2305 | 2902 | 165 | 762 | 0.217 | 0.217 |
| A108 | 0.364 | 1876 | 2034 | 2311 | 158 | 435 | 0.364 | 0.364 |
| A109 | 0.421 | 1900 | 2206 | 2627 | 306 | 727 | 0.421 | 0.421 |
| A110 | 0.310 | 2621 | 3048 | 4001 | 427 | 1380 | 0.310 | 0.310 |
| A111 | 0.393 | 2064 | 2409 | 2942 | 345 | 878 | 0.393 | 0.393 |
| A112 | 0.190 | 2000 | 2165 | 2868 | 165 | 868 | 0.190 | 0.190 |
| A113 | 0.283 | 1699 | 1872 | 2310 | 173 | 611 | 0.283 | 0.283 |
| A114 | 0.429 | 1838 | 2101 | 2452 | 263 | 614 | 0.429 | 0.429 |
| A115 | 0.297 | 2091 | 2281 | 2731 | 190 | 640 | 0.297 | 0.297 |
| A116 | 0.321 | 1571 | 1707 | 1994 | 136 | 423 | 0.321 | 0.321 |
| A117 | 0.275 | 1691 | 1874 | 2356 | 183 | 665 | 0.275 | 0.275 |
| A118 | 0.267 | 1835 | 1969 | 2338 | 134 | 503 | 0.267 | 0.267 |
| A119 | 0.260 | 2118 | 2320 | 2895 | 202 | 777 | 0.260 | 0.260 |
| A120 | 0.265 | 1833 | 1960 | 2313 | 127 | 480 | 0.265 | 0.265 |
| A121 | 0.308 | 1825 | 1992 | 2368 | 167 | 543 | 0.308 | 0.308 |
| A122 | 0.397 | 1674 | 1931 | 2322 | 257 | 648 | 0.397 | 0.397 |
| A123 | 0.320 | 1669 | 1824 | 2153 | 155 | 484 | 0.320 | 0.320 |
| A124 | 0.360 | 1627 | 1766 | 2013 | 139 | 386 | 0.360 | 0.360 |
| A125 | 0.181 | 1485 | 1591 | 2072 | 106 | 587 | 0.181 | 0.181 |
| A126 | 0.591 | 2476 | 2969 | 3310 | 493 | 834 | 0.591 | 0.591 |
| A127 | 0.160 | 1935 | 2040 | 2591 | 105 | 656 | 0.160 | 0.160 |
| A128 | 0.220 | 2485 | 2627 | 3132 | 142 | 647 | 0.220 | 0.220 |
| A129 | 0.255 | 3083 | 3385 | 4268 | 302 | 1185 | 0.255 | 0.255 |
| A130 | 0.254 | 3137 | 3330 | 3896 | 193 | 759 | 0.254 | 0.254 |
| A131 | 0.364 | 1729 | 1930 | 2282 | 201 | 553 | 0.364 | 0.364 |
| A132 | 0.364 | 2288 | 2601 | 3149 | 313 | 861 | 0.364 | 0.364 |
| A133 | 0.400 | 2132 | 2531 | 3130 | 399 | 998 | 0.400 | 0.400 |
| A134 | 0.500 | 3654 | 4285 | 4916 | 631 | 1262 | 0.500 | 0.500 |
| A135 | 0.341 | 1511 | 1652 | 1924 | 141 | 413 | 0.341 | 0.341 |
| A136 | 0.197 | 2697 | 2874 | 3596 | 177 | 899 | 0.197 | 0.197 |
| A137 | 0.420 | 1797 | 1980 | 2233 | 183 | 436 | 0.420 | 0.420 |
| A138 | 0.315 | 1931 | 2137 | 2585 | 206 | 654 | 0.315 | 0.315 |
| A139 | 0.227 | 1905 | 2069 | 2629 | 164 | 724 | 0.227 | 0.227 |
| A140 | 0.294 | 1483 | 1623 | 1959 | 140 | 476 | 0.294 | 0.294 |
| A141 | 0.315 | 1872 | 2044 | 2418 | 172 | 546 | 0.315 | 0.315 |
| A142 | 0.435 | 2390 | 2573 | 2811 | 183 | 421 | 0.435 | 0.435 |
| A143 | 0.515 | 2047 | 2421 | 2773 | 374 | 726 | 0.515 | 0.515 |
| A144 | 0.235 | 2017 | 2143 | 2553 | 126 | 536 | 0.235 | 0.235 |
| A145 | 0.246 | 1492 | 1602 | 1939 | 110 | 447 | 0.246 | 0.246 |
| A146 | 0.222 | 1899 | 2068 | 2660 | 169 | 761 | 0.222 | 0.222 |
| A147 | 0.288 | 1608 | 1738 | 2059 | 130 | 451 | 0.288 | 0.288 |
| A148 | 0.191 | 1967 | 2090 | 2610 | 123 | 643 | 0.191 | 0.191 |
| A149 | 0.328 | 1581 | 1718 | 1999 | 137 | 418 | 0.328 | 0.328 |
| A150 | 0.247 | 1558 | 1690 | 2092 | 132 | 534 | 0.247 | 0.247 |
| A151 | 0.289 | 2177 | 2402 | 2954 | 225 | 777 | 0.289 | 0.289 |
| A152 | 0.324 | 1876 | 2006 | 2278 | 130 | 402 | 0.324 | 0.324 |
| A153 | 0.232 | 1713 | 1859 | 2343 | 146 | 630 | 0.232 | 0.232 |
| A154 | 0.262 | 1887 | 2053 | 2520 | 166 | 633 | 0.262 | 0.262 |
| A155 | 0.368 | 2906 | 3327 | 4049 | 421 | 1143 | 0.368 | 0.368 |

TABLE 3-continued (Part B)

| ID | FTR od | Time@T2S | Time@Map | Time@TEot | ΔT2SMap | ΔT2STEot | FTR time | FTR od |
|---|---|---|---|---|---|---|---|---|
| A156 | 0.207 | 2191 | 2291 | 2674 | 100 | 483 | 0.207 | 0.207 |
| A157 | 0.385 | 1886 | 2065 | 2351 | 179 | 465 | 0.385 | 0.385 |
| A158 | 0.235 | 2424 | 2551 | 2964 | 127 | 540 | 0.235 | 0.235 |
| A159 | 0.290 | 2678 | 2973 | 3694 | 295 | 1016 | 0.290 | 0.290 |
| A160 | 0.435 | 2160 | 2489 | 2915 | 329 | 755 | 0.435 | 0.435 |
| A161 | 0.159 | 1674 | 1762 | 2227 | 88 | 553 | 0.159 | 0.159 |
| A162 | 0.232 | 3480 | 3835 | 5011 | 355 | 1531 | 0.232 | 0.232 |
| A163 | 0.238 | 2505 | 2697 | 3311 | 192 | 806 | 0.238 | 0.238 |
| A164 | 0.250 | 2535 | 2718 | 3267 | 183 | 732 | 0.250 | 0.250 |
| A165 | 0.197 | 2072 | 2189 | 2665 | 117 | 593 | 0.197 | 0.197 |
| A166 | 0.288 | 1883 | 2051 | 2467 | 168 | 584 | 0.288 | 0.288 |
| A167 | 0.214 | 2228 | 2321 | 2662 | 93 | 434 | 0.214 | 0.214 |
| A168 | 0.415 | 2366 | 2847 | 3525 | 481 | 1159 | 0.415 | 0.415 |
| A169 | 0.136 | 2543 | 2661 | 3412 | 118 | 869 | 0.136 | 0.136 |
| A170 | 0.351 | 1456 | 1589 | 1835 | 133 | 379 | 0.351 | 0.351 |
| A171 | 0.400 | 2463 | 2761 | 3208 | 298 | 745 | 0.400 | 0.400 |
| A172 | 0.200 | 1944 | 2070 | 2574 | 126 | 630 | 0.200 | 0.200 |
| A173 | 0.263 | 1505 | 1600 | 1866 | 95 | 361 | 0.263 | 0.263 |
| A174 | 0.254 | 1687 | 1816 | 2194 | 129 | 507 | 0.254 | 0.254 |
| A175 | 0.383 | 1681 | 1821 | 2047 | 140 | 366 | 0.383 | 0.383 |
| A176 | 0.245 | 2344 | 2544 | 3159 | 200 | 815 | 0.245 | 0.245 |
| A177 | 0.344 | 1596 | 1733 | 1995 | 137 | 399 | 0.344 | 0.344 |
| A178 | 0.262 | 2019 | 2183 | 2644 | 164 | 625 | 0.262 | 0.262 |
| A179 | 0.222 | 2056 | 2181 | 2619 | 125 | 563 | 0.222 | 0.222 |
| A180 | 0.375 | 1891 | 2096 | 2438 | 205 | 547 | 0.375 | 0.375 |
| A181 | 0.413 | 2575 | 2959 | 3505 | 384 | 930 | 0.413 | 0.413 |
| A182 | 0.204 | 1828 | 1930 | 2328 | 102 | 500 | 0.204 | 0.204 |
| A183 | 0.364 | 1523 | 1644 | 1856 | 121 | 333 | 0.364 | 0.364 |
| A184 | 0.214 | 2049 | 2187 | 2693 | 138 | 644 | 0.214 | 0.214 |
| A185 | 0.236 | 2417 | 2606 | 3217 | 189 | 800 | 0.236 | 0.236 |
| A186 | 0.455 | 2223 | 2909 | 3729 | 686 | 1506 | 0.455 | 0.455 |
| A187 | 0.234 | 1654 | 1755 | 2086 | 101 | 432 | 0.234 | 0.234 |
| A188 | 0.311 | 2229 | 2460 | 2972 | 231 | 743 | 0.311 | 0.311 |
| A189 | 0.392 | 2320 | 2588 | 3003 | 268 | 683 | 0.392 | 0.392 |
| A190 | 0.300 | 2473 | 2670 | 3130 | 197 | 657 | 0.300 | 0.300 |
| A191 | 0.276 | 1782 | 1907 | 2235 | 125 | 453 | 0.276 | 0.276 |
| A192 | 0.258 | 2127 | 2255 | 2623 | 128 | 496 | 0.258 | 0.258 |
| A193 | 0.214 | 1788 | 1920 | 2404 | 132 | 616 | 0.214 | 0.214 |
| A194 | 0.313 | 1930 | 2107 | 2496 | 177 | 566 | 0.313 | 0.313 |
| A195 | 0.235 | 1581 | 1710 | 2129 | 129 | 548 | 0.235 | 0.235 |
| A196 | 0.244 | 1821 | 1958 | 2381 | 137 | 560 | 0.244 | 0.244 |
| A197 | 0.203 | 1743 | 1835 | 2196 | 92 | 453 | 0.203 | 0.203 |
| A198 | 0.400 | 1696 | 1912 | 2236 | 216 | 540 | 0.400 | 0.400 |
| A199 | 0.417 | 1498 | 1665 | 1899 | 167 | 401 | 0.417 | 0.417 |
| A200 | 0.281 | 1441 | 1554 | 1843 | 113 | 402 | 0.281 | 0.281 |
| A201 | 0.273 | 2036 | 2205 | 2656 | 169 | 620 | 0.273 | 0.273 |
| A202 | 0.345 | 1898 | 2080 | 2426 | 182 | 528 | 0.345 | 0.345 |
| A203 | 0.244 | 1768 | 1880 | 2226 | 112 | 458 | 0.244 | 0.244 |
| A204 | 0.385 | 1642 | 1820 | 2105 | 178 | 463 | 0.385 | 0.385 |
| A205 | 0.256 | 1851 | 1983 | 2367 | 132 | 516 | 0.256 | 0.256 |
| A207 | 0.190 | 2173 | 2299 | 2835 | 126 | 662 | 0.190 | 0.190 |
| A208 | 0.333 | 2277 | 2531 | 3039 | 254 | 762 | 0.333 | 0.333 |
| A209 | 0.372 | 1721 | 1937 | 2302 | 216 | 581 | 0.372 | 0.372 |
| A210 | 0.278 | 1907 | 2066 | 2479 | 159 | 572 | 0.278 | 0.278 |
| A211 | 0.240 | 2153 | 2306 | 2791 | 153 | 638 | 0.240 | 0.240 |
| A212 | 0.421 | 2143 | 2458 | 2891 | 315 | 748 | 0.421 | 0.421 |
| A213 | 0.264 | 2057 | 2332 | 3099 | 275 | 1042 | 0.264 | 0.264 |
| A214 | 0.300 | 2116 | 2363 | 2939 | 247 | 823 | 0.300 | 0.300 |
| A215 | 0.255 | 1982 | 2118 | 2515 | 136 | 533 | 0.255 | 0.255 |
| A216 | 0.273 | 2799 | 3061 | 3760 | 262 | 961 | 0.273 | 0.273 |
| A217 | 0.244 | 2021 | 2237 | 2906 | 216 | 885 | 0.244 | 0.244 |
| A218 | 0.293 | 2319 | 2571 | 3179 | 252 | 860 | 0.293 | 0.293 |
| A219 | 0.393 | 2098 | 2309 | 2635 | 211 | 537 | 0.393 | 0.393 |
| A220 | 0.302 | 1803 | 1943 | 2266 | 140 | 463 | 0.302 | 0.302 |
| A222 | 0.310 | 1705 | 1876 | 2256 | 171 | 551 | 0.310 | 0.310 |
| A223 | 0.310 | 1593 | 1732 | 2041 | 139 | 448 | 0.310 | 0.310 |
| A224 | 0.357 | 1649 | 1811 | 2103 | 162 | 454 | 0.357 | 0.357 |
| A225 | 0.368 | 1655 | 1824 | 2114 | 169 | 459 | 0.368 | 0.368 |

Comparative Results of nATFt's and nATFz's

Results between patients in two different geographic locations (i.e., two different hospitals) were compared for correlation with each other. This comparison is expressed in Table 4 below, and includes a comparison of INR values calculated by the WHO method for each respective location, with GInr representing one location for these traditionally WHO determined values, and MInr representing values based on data obtained at the other location. The values identified as ATFz and ATFt, such as, GATFt and MATFt, and GATFz and MATFz, represent anticoagulant therapy factors derived from the expressions (1) through (9) above.

The ATFa represents an anticoagulation therapy factor derived from our method and apparatus for the expression $ATFa = XR^{(2-nFTR)}$ wherein a maximum acceleration point is obtained, and $nFTR = IUX/IUT$, where IUX is the change in optical density from a time prior to the MAP time ($t_{<MAP}$ which is $t_{MAP}$ minus some time from MAP) to the optical density at a time after the MAP time ($t_{>MAP}$ which is $t_{MAP}$ plus some time from MAP); and wherein IUT=the change in optical density at the time $t_1$ to the optical density measured at time $t_{EOT}$, where time $t_{EOT}$ is the end of the test (EOT). The (IUX) represents the fibrinogen (FBG) for MAP (−a number of seconds) to MAP (+a number of seconds) (that is the fibrinogen (FBG) converted from $t_{<MAP}$ to $t_{>MAP}$ on FIG. 2) The (IUT) represents fibrinogen converted from $c_1$ to $c_{EOT}$ (that is the fibrinogen converted from $t_1$ to $t_{EOT}$, see FIG. 2). The XR for the ATFa expression is $XR = TX/MNTX$, which is the ratio of time to map (TX) by the mean normal time to map of 20 presumed "normal" patients.

Comparative results were also calculated for the ATFt which includes the lag phase fibrinogen, in accordance with the IULz, using the expression (5.1) for the TEOT value. Table 6 below provides the values for the ATFz, ATFt, and the ATFt2 (which is obtained from expression 5.1 using the IULz).

TABLE 6

| ID | INR | INRz | ATFt | ATFt2 |
|---|---|---|---|---|
| A001 | 3.1 | 2.9 | 2.4 | 2.6 |
| A002 | 3.3 | 2.9 | 2.4 | 2.6 |
| A003 | 3.3 | 2.9 | 2.4 | 2.6 |
| A004 | 2.1 | 2.3 | 1.8 | 2.0 |
| A005 | 2.9 | 2.6 | 2.1 | 2.3 |
| A007 | 2.1 | 2.0 | 1.5 | 1.6 |
| A008 | 2.8 | 2.8 | 2.3 | 2.5 |
| A009 | 3.4 | 3.1 | 2.6 | 2.8 |
| A010 | 1.9 | 1.8 | 1.3 | 1.5 |
| A011 | 2.1 | 1.9 | 1.5 | 1.6 |
| A012 | 3.2 | 2.8 | 2.3 | 2.5 |
| A013 | 3.5 | 3.3 | 2.8 | 3.0 |
| A014 | 1.8 | 1.7 | 1.3 | 1.4 |
| A015 | 1.9 | 1.8 | 1.3 | 1.5 |
| A016 | 3.2 | 2.9 | 2.4 | 2.6 |

TABLE 4

COMPARATIVE RESULTS FOR ATFt and ATFz

| Comparison | n | r | m | b | Std. Error | Ng | Lassen |
|---|---|---|---|---|---|---|---|
| GInr vs. GATFa | 129 | 0.996 | 0.891 | 0.148 | 0.082 | 6/129 = 4.7% mismatches | delta <= 0.4 5@96.1% delta <= 0.7 2@98.4% |
| GInr vs. GATFz | 129 | 0.975 | 1.014 | −0.016 | 0.215 | 15/129 = 11.6% mismatches | delta <= 0.4 9@93% delta <= 0.7 3@97.7% |
| GInr vs. GATFt | 129 | 0.971 | 0.895 | 0.332 | 0.232 | 26/129 = 20.2% mismatches | delta <= 0.4 18@86.0% delta <=0.7 2@98.4% |
| MInr vs. MATFa | 129 | 0.996 | 0.943 | 0.082 | 0.094 | 18/129 = 14.0% mismatches | delta <= 0.4 15@88.4% delta <= 0.7 5@96.1% |
| MInr vs. MATFz | 129 | 0.985 | 0.993 | −0.058 | 0.177 | 2/129 = 1.6% mismatches | delta <= 0.4 0@100% delta <= 0.7 0@100% |
| MInr vs. MATFt | 129 | 0.981 | 0.851 | 0.420 | 0.200 | 8/129 = 6.2% mismatches | delta <= 0.4 6@95.3 delta <= 0.7 2@98.4% |

A comparison of combined location data is shown in Table 5, below. The sample size was 217.

TABLE 5

STATISTICAL SUMMARY OF MHTL DATA

| Comparison | n | r | m | b | Std. Error | Ng | Lassen |
|---|---|---|---|---|---|---|---|
| Inr vs ATFa | 217 | 0.984 | 1.006 | 0.011 | 0.215 | 30/217 = 13.8% mismatches | delta <= 0.4 16@92.6% delta <= 0.7 1@99.5% |
| Inr vs. ATFz | 217 | 0.984 | 1.002 | 0.120 | 0.214 | 26/217 = 12.0% mismatched | delta <= 0.4 18@91.7% delta <= 0.7 3@98.6% |
| Inr vs. ATFt | 217 | 0.984 | 0.900 | 0.482 | 1.218 | 45/217 = 20.7% mismatches | delta <= 0.4 43@80.2% delta <= 0.7 6@97.2% |

TABLE 6-continued

| ID | INR | INRz | ATFt | ATFt2 |
|---|---|---|---|---|
| A017 | 1.8 | 1.9 | 1.4 | 1.6 |
| A018 | 2.2 | 2.1 | 1.7 | 1.8 |
| A019 | 1.8 | 1.9 | 1.5 | 1.6 |
| A020 | 3.5 | 3.4 | 2.9 | 3.2 |
| A021 | 2.8 | 2.7 | 2.2 | 2.4 |
| A022 | 2.2 | 2.2 | 1.7 | 1.9 |
| A023 | 3.2 | 2.9 | 2.3 | 2.5 |
| A024 | 3.7 | 3.5 | 2.9 | 3.1 |
| A025 | 1.8 | 1.7 | 1.2 | 1.4 |
| A026 | 1.6 | 1.6 | 1.2 | 1.4 |
| A027 | 1.5 | 1.5 | 1.1 | 1.3 |
| A028 | 1.9 | 2.0 | 1.5 | 1.7 |
| A029 | 2.1 | 2.1 | 1.6 | 1.8 |
| A030 | 2.6 | 2.6 | 2.1 | 2.3 |
| A031 | 2.7 | 2.5 | 2.1 | 2.3 |
| A032 | 4.1 | 3.8 | 3.1 | 3.3 |
| A033 | 2.9 | 2.9 | 2.4 | 2.6 |
| A034 | 2.2 | 2.2 | 1.7 | 1.9 |
| A035 | 4.9 | 4.7 | 4.3 | 4.7 |
| A036 | 3.2 | 2.9 | 2.4 | 2.6 |
| A037 | 2.5 | 2.7 | 2.1 | 2.4 |
| A038 | 1.6 | 1.6 | 1.1 | 1.2 |
| A039 | 1.4 | 1.6 | 1.1 | 1.3 |
| A040 | 2.4 | 2.4 | 1.9 | 2.1 |
| A041 | 2.3 | 2.4 | 2.0 | 2.2 |
| A042 | 4.1 | 3.8 | 3.3 | 3.6 |
| A044 | 4.2 | 3.7 | 3.2 | 3.4 |
| A045 | 2.7 | 2.8 | 2.3 | 2.5 |
| A047 | 2.8 | 2.8 | 2.3 | 2.5 |
| A048 | 3.9 | 3.6 | 3.1 | 3.3 |
| A049 | 2.6 | 2.4 | 1.9 | 2.1 |
| A050 | 2.8 | 2.8 | 2.3 | 2.5 |
| A051 | 1.9 | 1.9 | 1.4 | 1.6 |
| A052 | 2.8 | 2.6 | 2.0 | 2.2 |
| A053 | 3.0 | 2.8 | 2.2 | 2.4 |
| A054 | 2.1 | 2.0 | 1.5 | 1.7 |
| A055 | 5.6 | 5.4 | 5.3 | 5.6 |
| A056 | 3.6 | 3.7 | 3.1 | 3.4 |
| A057 | 2.8 | 2.6 | 2.0 | 2.2 |
| A058 | 8.5 | 8.7 | 8.6 | 9.1 |
| A059 | 2.9 | 2.6 | 2.1 | 2.3 |
| A060 | 3.5 | 3.0 | 2.4 | 2.6 |
| A061 | 2.4 | 2.5 | 2.0 | 2.1 |
| A062 | 7.0 | 7.2 | 6.8 | 7.3 |
| A063 | 3.0 | 3.0 | 2.5 | 2.7 |
| A064 | 2.2 | 2.2 | 1.7 | 1.9 |
| A065 | 2.6 | 2.8 | 2.4 | 2.6 |
| A066 | 2.0 | 1.9 | 1.4 | 1.6 |
| A067 | 1.8 | 1.8 | 1.4 | 1.6 |
| A068 | 2.6 | 2.4 | 1.9 | 2.1 |
| A069 | 2.4 | 2.2 | 1.6 | 1.8 |
| A070 | 2.4 | 2.3 | 1.7 | 1.9 |
| A071 | 1.9 | 2.0 | 1.5 | 1.7 |
| A072 | 1.8 | 1.9 | 1.5 | 1.6 |
| A073 | 1.5 | 1.7 | 1.3 | 1.4 |
| A074 | 1.7 | 1.8 | 1.3 | 1.5 |
| A075 | 1.6 | 1.4 | 1.0 | 1.1 |
| A076 | 1.4 | 1.6 | 1.2 | 1.3 |
| A077 | 4.5 | 4.6 | 4.1 | 4.4 |
| A078 | 2.2 | 2.1 | 1.6 | 1.8 |
| A080 | 7.3 | 7.4 | 7.3 | 7.6 |
| A081 | 3.8 | 4.2 | 3.5 | 3.8 |
| A082 | 1.6 | 1.7 | 1.3 | 1.5 |
| A083 | 1.6 | 1.6 | 1.1 | 1.3 |
| A084 | 6.7 | 6.7 | 6.3 | 6.6 |
| A085 | 3.3 | 3.4 | 3.1 | 3.3 |
| A086 | 2.8 | 2.7 | 2.2 | 2.4 |
| A087 | 1.8 | 1.9 | 1.5 | 1.6 |
| A088 | 1.7 | 1.9 | 1.4 | 1.6 |
| A089 | 2.3 | 2.1 | 1.6 | 1.7 |
| A090 | 6.3 | 6.6 | 6.3 | 6.7 |
| A091 | 7.6 | 8.1 | 7.6 | 8.1 |
| A092 | 1.9 | 2.3 | 1.8 | 2.0 |
| A093 | 4.9 | 4.3 | 4.0 | 4.2 |
| A094 | 3.2 | 3.3 | 2.7 | 2.9 |
| A095 | 1.5 | 1.6 | 1.2 | 1.4 |
| A096 | 2.3 | 1.9 | 1.4 | 1.6 |
| A097 | 1.3 | 1.3 | 0.9 | 1.0 |
| A098 | 1.4 | 1.5 | 1.1 | 1.2 |
| A099 | 1.8 | 1.7 | 1.3 | 1.4 |
| A100 | 1.4 | 1.6 | 1.2 | 1.3 |
| A101 | 2.7 | 2.7 | 2.2 | 2.4 |
| A102 | 3.8 | 3.6 | 3.0 | 3.2 |
| A103 | 2.0 | 2.2 | 1.8 | 1.9 |
| A104 | 3.2 | 3.3 | 2.9 | 3.2 |
| A105 | 3.7 | 3.6 | 3.2 | 3.4 |
| A107 | 2.9 | 2.8 | 2.3 | 2.5 |
| A108 | 2.1 | 2.1 | 1.6 | 1.8 |
| A109 | 2.2 | 2.3 | 1.8 | 2.0 |
| A110 | 3.9 | 4.2 | 3.9 | 4.1 |
| A111 | 2.5 | 2.7 | 2.2 | 2.4 |
| A112 | 2.5 | 2.5 | 2.1 | 2.3 |
| A113 | 1.9 | 1.9 | 1.4 | 1.6 |
| A114 | 2.1 | 2.1 | 1.7 | 1.8 |
| A115 | 2.4 | 2.6 | 2.1 | 2.3 |
| A116 | 1.7 | 1.6 | 1.2 | 1.3 |
| A117 | 1.6 | 1.9 | 1.5 | 1.6 |
| A118 | 2.1 | 2.1 | 1.6 | 1.7 |
| A119 | 3.0 | 2.7 | 2.3 | 2.4 |
| A120 | 2.1 | 2.0 | 1.6 | 1.7 |
| A121 | 2.2 | 2.1 | 1.6 | 1.7 |
| A122 | 1.7 | 1.9 | 1.4 | 1.6 |
| A123 | 1.8 | 1.8 | 1.3 | 1.5 |
| A124 | 1.8 | 1.7 | 1.2 | 1.3 |
| A125 | 1.4 | 1.4 | 1.1 | 1.3 |
| A126 | 3.7 | 3.2 | 3.0 | 3.3 |
| A127 | 2.4 | 2.3 | 1.8 | 2.0 |
| A128 | 3.8 | 3.5 | 2.9 | 3.1 |
| A129 | 5.3 | 5.3 | 4.8 | 5.3 |
| A130 | 4.7 | 5.2 | 4.5 | 4.9 |
| A131 | 1.7 | 1.9 | 1.5 | 1.6 |
| A132 | 2.8 | 3.1 | 2.7 | 2.9 |
| A133 | 2.6 | 2.9 | 2.5 | 2.7 |
| A134 | 6.6 | 6.0 | 6.6 | 7.1 |
| A135 | 1.5 | 1.5 | 1.1 | 1.2 |
| A136 | 4.3 | 4.2 | 3.6 | 3.8 |
| A137 | 1.9 | 1.9 | 1.5 | 1.6 |
| A138 | 2.0 | 2.3 | 1.8 | 2.0 |
| A139 | 2.1 | 2.3 | 1.8 | 2.0 |
| A140 | 1.3 | 1.5 | 1.1 | 1.2 |
| A141 | 2.2 | 2.1 | 1.7 | 1.8 |
| A142 | 3.4 | 2.9 | 2.5 | 2.7 |
| A143 | 2.5 | 2.5 | 2.1 | 2.3 |
| A144 | 2.5 | 2.4 | 1.9 | 2.1 |
| A145 | 1.4 | 1.4 | 1.1 | 1.2 |
| A146 | 2.3 | 2.3 | 1.9 | 2.0 |
| A147 | 1.7 | 1.6 | 1.2 | 1.4 |
| A148 | 2.3 | 2.4 | 1.9 | 2.1 |
| A149 | 1.6 | 1.6 | 1.2 | 1.3 |
| A150 | 1.6 | 1.6 | 1.2 | 1.3 |
| A151 | 2.8 | 2.9 | 2.4 | 2.6 |
| A152 | 2.2 | 2.1 | 1.6 | 1.7 |
| A153 | 1.8 | 1.9 | 1.5 | 1.6 |
| A154 | 2.2 | 2.2 | 1.7 | 1.9 |
| A155 | 4.8 | 4.6 | 4.3 | 4.7 |
| A156 | 2.9 | 2.8 | 2.2 | 2.4 |
| A157 | 2.1 | 2.1 | 1.6 | 1.8 |
| A158 | 3.6 | 3.3 | 2.6 | 2.8 |
| A159 | 3.9 | 4.1 | 3.6 | 3.9 |
| A160 | 2.7 | 2.8 | 2.3 | 2.5 |
| A161 | 1.7 | 1.8 | 1.4 | 1.5 |
| A162 | 6.6 | 6.8 | 6.4 | 6.9 |
| A163 | 3.9 | 3.6 | 3.1 | 3.3 |
| A164 | 4.0 | 3.6 | 3.0 | 3.3 |
| A165 | 2.7 | 2.6 | 2.0 | 2.2 |
| A166 | 2.2 | 2.2 | 1.7 | 1.9 |
| A167 | 2.9 | 2.8 | 2.2 | 2.4 |
| A168 | 3.6 | 3.5 | 3.1 | 3.3 |
| A169 | 4.1 | 3.8 | 3.2 | 3.4 |
| A170 | 1.4 | 1.4 | 1.0 | 1.1 |
| A171 | 3.4 | 3.3 | 2.9 | 3.1 |
| A172 | 2.5 | 2.3 | 1.8 | 2.0 |
| A173 | 1.6 | 1.4 | 1.0 | 1.1 |
| A174 | 1.8 | 1.8 | 1.4 | 1.5 |

TABLE 6-continued

| ID | INR | INRz | ATFt | ATFt2 |
|---|---|---|---|---|
| A175 | 1.8 | 1.7 | 1.3 | 1.4 |
| A176 | 3.4 | 3.3 | 2.7 | 2.9 |
| A177 | 1.7 | 1.6 | 1.2 | 1.3 |
| A178 | 2.3 | 2.5 | 2.0 | 2.1 |
| A179 | 2.6 | 2.5 | 2.0 | 2.2 |
| A180 | 2.3 | 2.2 | 1.7 | 1.9 |
| A181 | 3.5 | 3.7 | 3.3 | 3.6 |
| A182 | 2.1 | 2.0 | 1.6 | 1.7 |
| A183 | 1.5 | 1.5 | 1.0 | 1.2 |
| A184 | 2.6 | 2.5 | 2.0 | 2.2 |
| A185 | 3.3 | 3.4 | 2.9 | 3.1 |
| A186 | 3.1 | 3.5 | 3.1 | 3.3 |
| A187 | 1.8 | 1.7 | 1.3 | 1.4 |
| A188 | 3.1 | 2.9 | 2.4 | 2.6 |
| A189 | 3.0 | 3.0 | 2.6 | 2.8 |
| A190 | 3.6 | 3.4 | 2.8 | 3.1 |
| A191 | 2.0 | 1.9 | 1.5 | 1.6 |
| A192 | 2.7 | 2.6 | 2.1 | 2.3 |
| A193 | 2.1 | 2.0 | 1.6 | 1.7 |
| A194 | 2.2 | 2.3 | 1.8 | 2.0 |
| A195 | 1.4 | 1.6 | 1.2 | 1.4 |
| A196 | 2.0 | 2.1 | 1.6 | 1.8 |
| A197 | 1.8 | 1.9 | 1.4 | 1.5 |
| A198 | 2.0 | 1.9 | 1.4 | 1.5 |
| A199 | 1.5 | 1.5 | 1.0 | 1.2 |
| A200 | 1.4 | 1.4 | 1.0 | 1.1 |
| A201 | 2.6 | 2.5 | 2.0 | 2.2 |
| A202 | 2.5 | 2.2 | 1.7 | 1.9 |
| A203 | 2.0 | 1.9 | 1.4 | 1.6 |
| A204 | 1.8 | 1.7 | 1.3 | 1.4 |
| A205 | 1.9 | 2.1 | 1.6 | 1.8 |
| A207 | 2.7 | 2.8 | 2.3 | 2.5 |
| A208 | 3.0 | 3.0 | 2.5 | 2.8 |
| A209 | 1.9 | 1.9 | 1.5 | 1.6 |
| A210 | 2.4 | 2.2 | 1.7 | 1.9 |
| A211 | 2.9 | 2.7 | 2.2 | 2.4 |
| A212 | 2.8 | 2.7 | 2.3 | 2.5 |
| A213 | 2.7 | 2.8 | 2.3 | 2.5 |
| A214 | 2.8 | 2.8 | 2.3 | 2.5 |
| A215 | 2.5 | 2.3 | 1.8 | 2.0 |
| A216 | 4.1 | 4.4 | 3.9 | 4.2 |
| A217 | 2.3 | 2.6 | 2.2 | 2.3 |
| A218 | 2.9 | 3.2 | 2.7 | 3.0 |
| A219 | 2.7 | 2.5 | 2.0 | 2.2 |
| A220 | 2.0 | 2.0 | 1.5 | 1.7 |
| A222 | 2.0 | 1.9 | 1.4 | 1.6 |
| A223 | 1.7 | 1.6 | 1.2 | 1.4 |
| A224 | 1.6 | 1.7 | 1.3 | 1.4 |
| A225 | 1.8 | 1.7 | 1.3 | 1.4 |

Table 7 represents a comparison of the data from Table 6.

TABLE 7

| | | "r" | "m" | "b" | StdErr | StdDev |
|---|---|---|---|---|---|---|
| INR | | | | | | |
| vs | INRz | 0.988 | 0.988 | 0.059 | 0.190 | 1.201 |
| | ATFt | 0.984 | 0.966 | 0.568 | 0.215 | 1.238 |
| | ATFt2 | 0.983 | 0.913 | 0.504 | 0.219 | 1.257 |
| ATFt | | | | | | |
| vs | ATFt2 | 1.000 | 0.946 | −0.068 | 0.022 | 1.264 |

Table 8 provides comparative data for the anticoagulant therapy factors, similar to Table 2, but using the ATFt2 method from expressions (4) and (5.1) for corresponding GINRt2 and MINRt2 values.

TABLE 8

| ID | AINR | GINR | GINRa | GINRz | GINRt2 | MINR | MINRa | MINRz | MINRt2 |
|---|---|---|---|---|---|---|---|---|---|
| U0800 | 2.0 | 2.0 | 2.0 | 2.0 | 1.7 | 2.1 | 2.1 | 2.2 | 2.1 |
| U7440 | 2.6 | 3.0 | 3.0 | 2.9 | 3.0 | 3.0 | 3.0 | 2.8 | 3.4 |
| U7443 | 2.0 | 2.0 | 2.0 | 2.0 | 1.8 | 2.1 | 2.2 | 2.1 | 1.8 |
| U7458 | 1.4 | 1.4 | 1.4 | 1.4 | 1.2 | 1.4 | 1.4 | 1.3 | 1.3 |
| U7465 | 9.7 | 7.4 | 8.1 | 6.6 | 7.9 | 7.1 | 7.5 | 8.1 | 7.8 |
| U7469 | 1.1 | 1.1 | 1.1 | 1.1 | 0.9 | 1.2 | 1.1 | 1.1 | 1.0 |
| U7470 | 3.2 | 3.4 | 3.6 | 3.4 | 3.2 | 3.6 | 3.7 | 3.8 | 3.8 |
| U8080 | 3.1 | 3.6 | 3.6 | 3.3 | 3.6 | 3.3 | 3.3 | 3.5 | 3.4 |
| U8087 | 1.9 | 1.9 | 1.9 | 1.8 | 1.6 | 1.9 | 1.9 | 1.9 | 1.7 |
| U8092 | 1.7 | 1.7 | 1.8 | 1.7 | 1.6 | 1.9 | 1.9 | 1.9 | 1.6 |
| U3050 | 2.7 | 2.8 | 3.1 | 2.6 | 2.2 | 2.3 | 2.3 | 2.3 | 2.0 |
| U3077 | 1.3 | 1.4 | 1.4 | 1.4 | 1.1 | 1.3 | 1.3 | 1.3 | 1.2 |
| U3083 | 1.6 | 1.6 | 1.6 | 1.6 | 1.3 | 1.6 | 1.7 | 1.6 | 1.4 |
| U8210 | 2.6 | 2.9 | 3.0 | 2.8 | 2.7 | 2.7 | 2.8 | 2.8 | 2.6 |
| U8221 | 3.2 | 3.7 | 4.0 | 3.7 | 3.4 | 3.5 | 3.5 | 3.3 | 3.6 |
| U3408 | 1.1 | 1.2 | 1.2 | 1.2 | 0.9 | 1.1 | 1.0 | 1.0 | 0.9 |
| U3453 | 1.1 | 1.2 | 1.2 | 1.2 | 1.0 | 1.2 | 1.2 | 1.2 | 1.0 |
| U3457 | 2.2 | 2.3 | 2.4 | 2.2 | 1.9 | 2.1 | 2.3 | 2.2 | 1.8 |
| U3395 | 2.7 | 3.2 | 3.5 | 3.2 | 2.7 | 2.8 | 2.9 | 2.5 | 2.3 |
| U3398 | 1.5 | 1.7 | 1.8 | 1.8 | 1.5 | 1.6 | 1.6 | 1.6 | 1.5 |
| U3456 | 1.1 | 1.0 | 1.0 | 1.0 | 0.8 | 1.0 | 1.0 | 1.0 | 0.9 |
| U3459 | 2.9 | 2.6 | 2.8 | 2.6 | 2.2 | 2.4 | 2.5 | 2.5 | 2.0 |
| U0415 | 0.9 | 0.9 | 0.9 | 0.9 | 0.8 | 0.9 | 1.0 | 1.0 | 0.8 |
| U0432 | 1.8 | 1.5 | 1.5 | 1.5 | 1.3 | 1.4 | 1.4 | 1.4 | 1.3 |
| U0436 | 2.4 | 2.4 | 2.6 | 2.3 | 2.1 | 2.4 | 2.4 | 2.4 | 2.2 |
| U0438 | 3.9 | 3.7 | 4.2 | 3.7 | 3.2 | 3.8 | 4.2 | 3.9 | 3.6 |
| U0439 | 2.3 | 2.2 | 2.3 | 2.1 | 1.8 | 2.3 | 2.3 | 2.2 | 2.0 |
| U0440 | 5.8 | 4.8 | 5.4 | 5.2 | 4.4 | 4.6 | 4.8 | 4.3 | 5.2 |
| U0441 | 4.5 | 4.9 | 5.6 | 6.0 | 5.0 | 4.4 | 4.7 | 4.7 | 5.4 |
| U0442 | 1.8 | 1.7 | 1.8 | 1.7 | 1.5 | 1.8 | 1.8 | 1.8 | 1.6 |
| U3724 | 2.7 | 2.4 | 2.5 | 2.4 | 2.0 | 2.6 | 2.7 | 2.6 | 2.3 |
| U0849 | 2.4 | 2.3 | 2.4 | 2.1 | 1.8 | 2.3 | 2.4 | 2.2 | 2.0 |
| U0860 | 1.0 | 1.0 | 1.0 | 1.0 | 0.8 | 1.0 | 1.0 | 1.0 | 0.9 |

TABLE 8-continued

| ID | AINR | GINR | GINRa | GINRz | GINRt2 | MINR | MINRa | MINRz | MINRt2 |
|---|---|---|---|---|---|---|---|---|---|
| U0861 | 2.8 | 2.9 | 3.0 | 2.8 | 2.6 | 3.0 | 3.0 | 2.9 | 3.0 |
| U0863 | 1.7 | 1.7 | 1.7 | 1.7 | 1.7 | 1.7 | 1.8 | 1.8 | 1.8 |
| U0875 | 2.2 | 2.0 | 2.2 | 2.1 | 1.6 | 2.0 | 2.0 | 2.0 | 1.7 |
| U0843 | 1.4 | 1.4 | 1.4 | 1.4 | 1.2 | 1.4 | 1.5 | 1.5 | 1.3 |
| U0848 | 1.3 | 1.4 | 1.4 | 1.4 | 1.2 | 1.3 | 1.4 | 1.4 | 1.2 |
| U0855 | 1.3 | 1.3 | 1.3 | 1.3 | 1.2 | 1.2 | 1.2 | 1.2 | 1.3 |
| U0867 | 3.2 | 2.9 | 3.2 | 2.8 | 2.5 | 3.0 | 3.1 | 3.0 | 2.9 |
| U1201 | 1.9 | 1.9 | 2.0 | 1.9 | 1.7 | 1.8 | 1.8 | 1.9 | 1.8 |
| U1202 | 1.3 | 1.3 | 1.3 | 1.3 | 1.2 | 1.4 | 1.4 | 1.4 | 1.2 |
| U1205 | 1.6 | 1.8 | 1.9 | 1.8 | 1.6 | 1.9 | 1.9 | 1.9 | 1.7 |
| U1207 | 1.9 | 1.9 | 2.0 | 1.8 | 1.5 | 1.9 | 1.9 | 1.7 | 1.7 |
| U1230 | 1.3 | 1.4 | 1.5 | 1.4 | 1.3 | 1.4 | 1.5 | 1.5 | 1.5 |
| U1198 | 2.2 | 2.1 | 2.2 | 2.1 | 1.9 | 2.0 | 2.0 | 2.0 | 2.3 |
| U1199 | 2.8 | 3.3 | 3.6 | 3.1 | 2.8 | 3.2 | 3.2 | 2.8 | 3.3 |
| U1218 | 3.0 | 2.6 | 2.9 | 2.9 | 2.7 | 2.8 | 3.1 | 3.1 | 3.2 |
| U1225 | 2.2 | 2.3 | 2.3 | 2.1 | 1.9 | 2.6 | 2.4 | 2.2 | 2.2 |
| U1575 | 1.4 | 1.3 | 1.3 | 1.3 | 1.4 | 1.4 | 1.4 | 1.4 | 1.4 |
| U1579 | 1.5 | 1.7 | 1.7 | 1.7 | 1.5 | 1.8 | 1.8 | 1.7 | 1.5 |
| U1649 | 0.9 | 0.8 | 0.8 | 0.8 | 0.8 | 0.9 | 0.9 | 0.9 | 0.8 |
| U1576 | 2.2 | 2.1 | 2.1 | 2.1 | 2.1 | 2.3 | 2.3 | 2.3 | 2.2 |
| U1581 | 1.7 | 1.7 | 1.7 | 1.8 | 1.9 | 1.7 | 1.8 | 1.8 | 1.7 |
| U1599 | 2.0 | 1.7 | 1.8 | 1.8 | 2.0 | 2.0 | 2.1 | 2.1 | 2.0 |
| U1600 | 3.5 | 3.2 | 3.4 | 3.4 | 3.7 | 3.9 | 4.2 | 3.5 | 3.7 |
| U4471 | 1.5 | 1.6 | 1.7 | 1.6 | 1.5 | 1.7 | 1.7 | 1.7 | 1.7 |
| U4757 | 2.0 | 2.1 | 2.1 | 2.0 | 1.8 | 2.0 | 2.0 | 2.1 | 2.0 |
| U4767 | 2.6 | 2.4 | 2.5 | 2.6 | 2.0 | 2.6 | 2.6 | 2.5 | 2.3 |
| U4772 | 2.5 | 2.7 | 2.8 | 2.5 | 2.6 | 2.8 | 2.8 | 2.9 | 2.5 |
| U4801 | 1.3 | 1.4 | 1.4 | 1.4 | 1.2 | 1.5 | 1.5 | 1.4 | 1.2 |
| U4737 | 2.9 | 2.6 | 2.8 | 2.7 | 2.3 | 2.7 | 2.9 | 2.8 | 2.5 |
| U4752 | 1.4 | 1.5 | 1.6 | 1.5 | 1.3 | 1.5 | 1.5 | 1.5 | 1.4 |
| U5133 | 0.9 | 0.9 | 0.9 | 0.9 | 0.7 | 1.0 | 1.0 | 1.0 | 0.8 |
| U5173 | 1.1 | 1.2 | 1.2 | 1.2 | 1.1 | 1.2 | 1.2 | 1.2 | 1.0 |
| U5175 | 1.7 | 1.8 | 1.9 | 1.8 | 1.7 | 1.9 | 1.9 | 1.9 | 1.7 |
| U5178 | 2.3 | 2.2 | 2.3 | 2.1 | 1.9 | 2.6 | 2.9 | 2.8 | 2.0 |
| U5183 | 2.9 | 2.6 | 2.8 | 2.6 | 2.3 | 3.6 | 3.9 | 3.7 | 3.0 |
| U5158 | 5.5 | 5.1 | 5.9 | 5.7 | 5.8 | 6.0 | 6.6 | 7.1 | 7.0 |
| U5169 | 2.6 | 2.9 | 3.2 | 3.2 | 3.2 | 3.2 | 3.4 | 3.6 | 3.7 |
| U5190 | 2.8 | 2.7 | 2.8 | 2.9 | 2.8 | 3.2 | 3.4 | 3.5 | 3.2 |
| U5193 | 3.1 | 3.0 | 3.1 | 3.0 | 2.9 | 3.6 | 3.7 | 3.7 | 3.4 |
| U5589 | 1.6 | 1.8 | 1.9 | 1.8 | 1.6 | 1.9 | 2.0 | 1.8 | 1.5 |
| U5592 | 1.1 | 1.2 | 1.2 | 1.2 | 1.1 | 1.4 | 1.3 | 1.3 | 1.4 |
| U5593 | 1.7 | 1.8 | 1.9 | 1.8 | 1.6 | 1.8 | 1.9 | 1.8 | 1.7 |
| U5565 | 2.7 | 3.2 | 3.3 | 3.3 | 3.1 | 3.5 | 3.5 | 3.6 | 3.5 |
| U5591 | 2.0 | 2.2 | 2.3 | 2.3 | 2.1 | 2.3 | 2.3 | 2.1 | 2.3 |
| U5594 | 2.3 | 2.6 | 2.8 | 2.8 | 2.8 | 2.8 | 2.8 | 3.0 | 3.0 |
| U5597 | 3.3 | 3.3 | 3.6 | 3.6 | 3.1 | 4.1 | 4.0 | 4.3 | 4.0 |
| U5993 | 1.0 | 0.9 | 0.9 | 0.9 | 0.8 | 1.0 | 1.0 | 1.0 | 0.8 |
| U6017 | 1.0 | 0.9 | 1.0 | 1.0 | 0.8 | 0.9 | 0.9 | 0.9 | 0.8 |
| U6056 | 1.0 | 1.0 | 1.0 | 1.0 | 0.9 | 1.0 | 1.0 | 1.0 | 0.9 |
| U5992 | 1.4 | 1.4 | 1.4 | 1.4 | 1.3 | 1.3 | 1.4 | 1.4 | 1.3 |
| U6047 | 2.3 | 2.3 | 2.4 | 2.3 | 2.0 | 2.2 | 2.3 | 2.3 | 2.2 |
| U6060 | 1.9 | 2.1 | 2.2 | 2.2 | 2.0 | 2.3 | 2.2 | 2.0 | 2.1 |
| U6065 | 3.1 | 2.8 | 2.9 | 2.8 | 2.7 | 3.0 | 3.1 | 2.9 | 2.8 |
| U6928 | 1.2 | 1.2 | 1.2 | 1.2 | 1.2 | 1.2 | 1.2 | 1.2 | 1.1 |
| U6929 | 1.2 | 1.2 | 1.2 | 1.2 | 1.1 | 1.2 | 1.2 | 1.2 | 1.0 |
| U6951 | 1.5 | 1.5 | 1.5 | 1.5 | 1.5 | 1.6 | 1.7 | 1.6 | 1.4 |
| U6977 | 1.3 | 1.3 | 1.3 | 1.3 | 1.2 | 1.3 | 1.4 | 1.4 | 1.1 |
| U6936 | 2.4 | 2.5 | 2.4 | 2.6 | 3.2 | 2.6 | 2.6 | 2.7 | 2.6 |
| U6938 | 2.1 | 2.1 | 2.1 | 2.2 | 2.3 | 2.3 | 2.3 | 2.3 | 2.3 |
| U6972 | 2.4 | 2.4 | 2.5 | 2.4 | 2.5 | 2.8 | 2.8 | 2.8 | 2.5 |
| U6987 | 5.1 | 4.5 | 4.4 | 5.0 | 5.5 | 5.7 | 5.4 | 5.7 | 7.0 |
| U7316 | 1.2 | 1.1 | 1.1 | 1.1 | 1.1 | 1.3 | 1.3 | 1.3 | 1.1 |
| U7321 | 1.5 | 1.4 | 1.4 | 1.4 | 1.5 | 1.6 | 1.6 | 1.6 | 1.5 |
| U7324 | 1.3 | 1.2 | 1.3 | 1.2 | 1.2 | 1.4 | 1.4 | 1.4 | 1.2 |
| U7317 | 2.0 | 1.6 | 1.7 | 1.7 | 1.6 | 1.9 | 1.9 | 1.8 | 1.6 |
| U7318 | 2.8 | 2.7 | 2.9 | 2.9 | 2.6 | 3.3 | 3.4 | 3.3 | 2.7 |
| U7320 | 2.0 | 1.9 | 1.9 | 1.9 | 2.2 | 2.0 | 2.1 | 2.1 | 2.2 |
| U7322 | 1.8 | 1.7 | 1.7 | 1.7 | 1.5 | 1.7 | 1.8 | 1.7 | 1.4 |
| U7708 | 1.6 | 1.6 | 1.6 | 1.6 | 1.6 | 1.7 | 1.7 | 1.7 | 1.7 |
| U7713 | 1.4 | 1.6 | 1.6 | 1.6 | 1.5 | 1.6 | 1.6 | 1.6 | 1.5 |
| U7727 | 1.7 | 1.7 | 1.7 | 1.8 | 1.7 | 1.9 | 1.9 | 1.9 | 1.9 |
| U7794 | 1.9 | 1.8 | 1.9 | 1.8 | 1.6 | 1.7 | 1.8 | 1.7 | 1.6 |
| U7707 | 2.2 | 2.2 | 2.3 | 2.3 | 2.3 | 2.3 | 2.3 | 2.3 | 2.2 |
| U7710 | 2.3 | 2.5 | 2.6 | 2.7 | 2.8 | 2.7 | 2.9 | 3.0 | 3.0 |
| U7724 | 2.4 | 2.4 | 2.5 | 2.6 | 2.7 | 2.7 | 2.7 | 2.8 | 2.9 |
| U7738 | 2.4 | 2.3 | 2.4 | 2.5 | 2.2 | 2.4 | 2.5 | 2.6 | 2.3 |
| U8559 | 1.6 | 1.4 | 1.4 | 1.4 | 1.3 | 1.6 | 1.7 | 1.6 | 1.3 |

TABLE 8-continued

| ID | AINR | GINR | GINRa | GINRz | GINRt2 | MINR | MINRa | MINRz | MINRt2 |
|---|---|---|---|---|---|---|---|---|---|
| U8570 | 1.2 | 1.2 | 1.2 | 1.2 | 1.3 | 1.2 | 1.2 | 1.2 | 1.3 |
| U8575 | 0.9 | 0.8 | 0.8 | 0.8 | 0.8 | 0.9 | 0.9 | 0.9 | 0.8 |
| U8555 | 2.6 | 2.4 | 2.5 | 2.6 | 2.6 | 2.9 | 3.1 | 3.0 | 2.6 |
| U8558 | 2.3 | 2.2 | 2.3 | 2.3 | 2.2 | 2.3 | 2.3 | 2.4 | 2.4 |
| U8563 | 2.2 | 2.3 | 2.3 | 2.4 | 2.3 | 2.4 | 2.4 | 2.5 | 2.5 |
| U9031 | 2.1 | 2.4 | 2.3 | 2.3 | 2.5 | 2.6 | 2.4 | 2.3 | 2.4 |
| U9032 | 1.7 | 1.7 | 1.7 | 1.7 | 1.6 | 1.9 | 1.9 | 1.7 | 1.5 |
| U9040 | 1.4 | 1.4 | 1.4 | 1.4 | 1.2 | 1.4 | 1.4 | 1.3 | 1.1 |
| U9034 | 3.0 | 2.9 | 2.8 | 3.0 | 4.0 | 3.4 | 3.4 | 3.5 | 3.8 |
| U9039 | 2.7 | 3.0 | 3.2 | 3.1 | 3.1 | 3.2 | 3.2 | 3.2 | 3.3 |
| U9049 | 3.5 | 3.3 | 3.5 | 3.5 | 3.5 | 3.6 | 3.8 | 3.6 | 3.7 |
| U9055 | 2.4 | 2.1 | 2.1 | 2.2 | 2.1 | 2.4 | 2.4 | 2.4 | 2.1 |
| U0048 | 1.8 | 1.8 | 1.8 | 1.8 | 1.7 | 1.9 | 2.0 | 2.0 | 1.8 |
| U0050 | 1.8 | 1.7 | 1.8 | 1.8 | 1.7 | 1.9 | 2.0 | 2.0 | 1.7 |
| U0056 | 1.6 | 1.5 | 1.5 | 1.5 | 1.4 | 1.8 | 1.8 | 1.7 | 1.5 |
| U0047 | 2.1 | 1.7 | 1.8 | 1.8 | 1.6 | 2.0 | 2.1 | 2.0 | 1.7 |
| U0058 | 3.2 | 2.8 | 2.9 | 3.0 | 3.0 | 3.3 | 3.4 | 3.2 | 3.3 |
| U0060 | 2.2 | 2.1 | 2.1 | 2.2 | 2.1 | 2.2 | 2.2 | 2.2 | 2.3 |
| U0062 | 2.8 | 2.6 | 2.7 | 2.8 | 2.7 | 3.0 | 3.2 | 3.2 | 2.9 |

TABLE 9

COMPARATIVE RESULTS

| Comparison on | n | r | m | b | Std. Error | Ng | Lassen |
|---|---|---|---|---|---|---|---|
| GInr vs GATFa | 129 | 0.997 | 0.879 | 0.163 | 0.079 | 7/129 = 5.4% | Delta <= 0.4 \| 5@96.1%<br>Delta <= 0.7 \| 2@98.4% |
| GInr vs GATFz | 129 | 0.986 | 0.948 | 0.078 | 0.162 | 3/129 = 2.3% | Delta <= 0.4 \| 4@96.9%<br>Delta <= 0.7 \| 2@98.4% |
| GInr vs GATFt2 | 129 | 0.974 | 0.935 | 0.413 | 0.221 | 20/129 = 15.5% | Delta <= 0.4 \| 16@87.6%<br>Delta <= 0.7 \| 4@96.9% |
| MInr vs MATFa | 129 | 0.996 | 0.921 | 0.122 | 0.092 | 9/129 = 7.0% | Delta <= 0.4 \| 2@98.4%<br>Delta <= 0.7 \| 0@100.0% |
| MInr vs MATFz | 129 | 0.989 | 0.908 | 0.190 | 0.155 | 7/129 = 5.4% | Delta <= 0.4 \| 4@96.9%<br>Delta <= 0.7 \| 2@98.4% |
| MInr vs MATFt2 | 129 | 0.983 | 0.893 | 0.491 | 0.193 | 8/129 = 6.2% | Delta <= 0.4 \| 13@89.9%<br>Delta <= 0.7 \| 4@96.9% |

Table 9 provides comparative data for the ATFa, ATFz and ATFt2 and INR values calculated by the WHO method for each respective location, with GInr representing one location for these traditionally WHO determined values, and MInr representing values based on data obtained at the other location. The values identified as ATFz and ATFt2, such as, GATFt2 and MATFt2, and GATFz and MATFz, represent anticoagulant therapy factors derived from the expressions (1) through (9) above, inclusive of expressions (5.1) and (8.1).

Further comparative results are provided in Table 10 to illustrate the effect of prothrombin time (PT) on INR values. Table 10 provides a comparison based on data from Table 3, and provides INR values for PT's of PT=PT (under the heading "INR"), PT=PT+0.5 (under the heading "+0.5"), PT=PT+1.0 (under the heading "+1.0"), PT=PT+1.5 (under the heading "+1.5"), and PT=+2.0 (under the heading "+2.0"). The new anticoagulation therapy factor (ATFt2) was compared with the WHO method for determining ATF. The WHO method utilizes the mean prothrombin time of 20 presumed normal patients. The thromboplastin reagents list MNPT "expected ranges" listed in the accompanying thromboplastin-reagent (Tp) brochures. These brochures acknowledge that MNPT differences are inevitable because of variations in the 20 "normal donor" populations. Geometric, rather than arithmetic mean calculation limits MNPT variation somewhat, but simulated 0.5 second incremented increases over a total 2.5 second range, show ever-increasing INR differences notably at higher INR levels. To exemplify this, Table 10 shows these changes with Thromboplastin C Plus (which has a manufacturer's reported ISI=1.74 and MNPT=9.89 seconds) in POTENS+.

TABLE 10

| ID | PT | INR | +0.5 | +1.0 | +1.5 | +2.0 |
|---|---|---|---|---|---|---|
| WEC | 9.8 | 1.0 | 0.9 | 0.8 | 0.8 | 0.7 |
| A095 | 12.5 | 1.5 | 1.4 | 1.3 | 1.2 | 1.1 |
| A191 | 14.8 | 2.0 | 1.9 | 1.7 | 1.6 | 1.5 |
| A112 | 16.9 | 2.5 | 2.3 | 2.2 | 2.0 | 1.8 |
| A208 | 18.6 | 3.0 | 2.8 | 2.5 | 2.3 | 2.2 |
| A020 | 20.3 | 3.5 | 3.2 | 3.0 | 2.7 | 2.5 |
| A164 | 21.9 | 4.0 | 3.7 | 3.4 | 3.1 | 2.9 |
| A093 | 24.5 | 4.9 | 4.5 | 4.1 | 3.8 | 3.5 |
| A055 | 26.5 | 5.6 | 5.1 | 4.7 | 4.4 | 4.0 |
| A090 | 28.5 | 6.3 | 5.8 | 5.3 | 4.9 | 4.6 |
| R091 | 32.2 | 7.8 | 7.2 | 6.6 | 6.1 | 5.7 |
| A058 | 33.8 | 8.5 | 7.8 | 7.2 | 6.6 | 6.2 |

Since the in-house determined MNPT would continue with that Tp lot, intralaboratory results would be relatively unaffected. However, between laboratory INR agreements, or interlab results, are compromised. As a denominator, considering the expression used to derive the MNPT, such as expression (B), above, MNPT is, of course, less problematic for INRs than the exponent, ISI. Comparative results, showing interlab results, are provided in Table 11. ATFt is seen to be numerically equal to WHO/INRs determined in both analytical instruments, namely, the MDA-Electra 9000C and the POTENS+. Identical computer bits derived in POTENS+ from the absorbances creating the thrombin-fibrinogen-fibrin clotting curve are used for the POTENS+ WHO/INR and ATFt (NO ISI, NO MNPT) determinations. MNPT is, of course, still necessary for the WHO method. For ATFt, Zero Order Kinetics Line's slope is extended in both directions to intersect with the Tp-plasma baseline and the absorbance at total fibrin formation. The sum of this interval and the time from the Tp injection to the beginning of Zero Order Kinetics ($T_2S$) is Value 1. Value 2 is $T_2S/100e$. "e" is the Natural Logarithm, base 2.71828. ATFt=(Value 1)*(Value 2), in accordance with expression (4) herein (and the expression (8.1) for ATFt2).

Table 11 provides statistical comparisons for results obtained using two POTENS+ coagulometers (one designated as GINR and another designated as MINR), and using a Bio Merieux MDA-180 coagulometer (designated as AINR). The POTENS+, WHO/INRs, $INR_z$s, and ATFts and the MDA-180 (AINR) WHO/INRs are compared. Statistical data and Bland-Altman plot data demonstrate that the new anticoagulant therapy factor ATFt may replace WHO/INR and provide results which are within the parameters of traditional therapeutic or reference ranges.

said computer processor and/or storage device as a function of the optical density for a sample being analyzed. The chip may be employed in, or used with, an apparatus having input means and storage means for storing data. The set of instructions on the chip includes instructions for carrying out the steps of determining one or more anticoagulant therapy factors based on the expressions (1) through (9), inclusive of expressions (5.1) and (8.1).

While the invention has been described with reference to specific embodiments, the description is illustrative and is not to be construed as limiting the scope of the invention. The sample container used to contain the sample may comprise a vial, or cuvette, including, for example, the sample container disclosed in our U.S. Pat. No. 6,706,536. For example, although described in connection with body fluids of a human, the present invention has applicability to veterinary procedures, as well, where fluids are to be measured or analyzed. Various modifications and changes may occur to those skilled in the art without departing from the spirit and scope of the invention described herein and as defined by the appended claims.

What is claimed is:

1. A method of determining a new anticoagulant therapy factor (nATF) comprising the steps of
   a. developing a series of analog electrical voltage signals having voltage amplitudes proportional to an optical density of a liquid sample containing fibrinogen;

TABLE 11

| | | "r" | "m" | "b" | StdErr | StdDev | mY | mX | My/mX |
|---|---|---|---|---|---|---|---|---|---|
| AINR | | | | | | | | | |
| vs | GINR | 0.937 | 0.872 | 0.290 | 0.388 | 1.148 | 2.169 | 2.155 | 1.007 |
| | GATFz | 0.941 | 1.119 | −0.208 | 0.378 | 1.022 | 2.169 | 2.124 | 1.021 |
| | GATFt2 | 0.951 | 1.003 | 0.146 | 0.343 | 1.081 | 2.169 | 2.016 | 1.076 |
| | MINR | 0.950 | 1.018 | −0.126 | 0.349 | 1.070 | 2.169 | 2.253 | 0.963 |
| | MATFz | 0.943 | 1.020 | −0.040 | 0.371 | 1.065 | 2.169 | 2.167 | 1.001 |
| | MATFt2 | 0.937 | 0.872 | 0.290 | 0.388 | 1.148 | 2.169 | 2.155 | 1.007 |
| MINR | | | | | | | | | |
| vs MINRz | GINR | 0.971 | 1.036 | 0.039 | 0.247 | 1.001 | 2.253 | 2.136 | 1.055 |
| vs MINRt2 | GINRz | 0.984 | 1.082 | −0.132 | 0.186 | 0.978 | 2.167 | 2.124 | 1.020 |
| vs | GINRt2 | 0.979 | 1.110 | −0.083 | 0.242 | 1.123 | 2.155 | 2.016 | 1.069 |

The linear regression analysis expression y=mx+b, when solved for the slope, m, is expressed as (y−b)/x. This is biased, so the expression is y/x is when b is equal to zero. The comparison in Table 11, above, provides comparative data for mean y (mY) and mean x (mX) values, including the slope mY/mX. The use of mY/mX is used to provide comparative results.

In another embodiment, an article may be provided to derive an anticoagulant therapy factor (ATF). The article may comprise stored instructions on a storage media which can be read and processed with a processor. For example, the computer may be provided with a stored set of instructions, or chip, which is programmed to determine a new ATF for the spectral data obtained from the coagulation activity of a sample. For example, the computer chip may be preprogrammed with a set of instructions for cooperating with the output of a photodetection device, such as, the device shown and described in FIG. 1, which provides electrical data to b. converting the developed analog voltage signals into a series of digital voltage value signals;

c. adding a coagulant into the liquid sample, thereby producing an abrupt change in the optical density of the liquid sample, said abrupt change producing an abrupt change in the amplitude of the electrical analog signals which, in turn, produces an abrupt change in the value of said digital voltage signals, the value of said digital voltage signals being directly indicative of fibrinogen concentration in the liquid sample;

d. recording an instant time $t_0$ of said abrupt change in said value of said digital voltage signal;

e. monitoring said voltage digital signal values for a first predetermined fibrinogen concentration quantity $c_1$;

f. recording an instant time $t_1$ and the value of the voltage digital signal of said first predetermined fibrinogen concentration quantity $c_1$;

g. monitoring said voltage digital signal values for further fibrinogen concentration quantities;
h. recording an instant time $t_{MAP}$ and the value of the voltage digital signal corresponding at that time $t_{MAP}$ to a fibrinogen concentration quantity $c_{MAP}$, wherein $t_{MAP}$ corresponds with the point where the maximum acceleration of the conversion of fibrinogen to fibrin occurs;
i. recording an elapsed time between $t_0$ and $t_{MAP}$) which defines a time to maximum acceleration from coagulant injection in step c.;
j. monitoring for a differential change in the voltage digital signal values that include said fibrinogen concentration quantity $c_{MAP}$;
wherein said fibrinogen concentration quantity $c_{MAP}$ and said time $t_{MAP}$ define a maximum acceleration point (MAP) and a time to maximum acceleration from coagulant injection (TX), wherein TX is measured as the elapsed time from the time of the coagulant injection $t_0$ to the time to maximum acceleration $t_{MAP}$, and each of the quantity $c_{MAP}$ and said time $t_{MAP}$ having a predetermined range starting prior to, at a time $t_{<MAP}$, and ending after said maximum acceleration point (MAP), at a time $t_{>MAP}$;
k. monitoring voltage digital signal values at times $t_{<MAP}$ and $t_{>MAP}$ for respective predetermined fibrinogen concentration quantities $c_{>MAP}$ and $c_{>MAP}$, with the difference between quantities $c_{<MAP}$ and $c_{>MAP}$ being a first differential IUX;
l. monitoring voltage digital signal values at time $t_{EOT}$, wherein time $t_{EOT}$ defines a fibrinogen end point corresponding with the substantially complete conversion of fibrinogen to fibrin, and recording at an instant time $t_{EOT}$ the value of the voltage digital signal of a predetermined fibrinogen concentration quantity $c_{EOT}$, with the difference between quantities $c_1$ and $c_{EOT}$ being a second differential IUT, the first differential being divided by the second differential to define a percentage of the total voltage digital signal value change covered by an overall range defining a new fibrinogen transformation rate (nFTR), where nFTR=IUX/IUT;
wherein a maximum acceleration ratio (XR) is determined by the time to maximum acceleration from the coagulant injection (TX) divided by a mean normal TX value (MNTX) of a sample from patients with presumed normal coagulation;
wherein the new anticoagulant therapy factor (nATF) is expressed by the following relationship:

$$nATF = XR^{(2-nFTR)}.$$

2. The method of claim 1, wherein the sample from patients with presumed normal coagulation is about 20 patients.

3. The method of claim 1, wherein the MNTX is the mean of the TX of a plurality of samples from at least twenty (20) people with presumed normal coagulation.

4. The method of claim 1, wherein the sample from patients with presumed normal coagulation is about equal to or greater than 20 patients.

5. The method of claim 1, wherein the predetermined range starting prior to and ending after said maximum acceleration point (MAP) is from about a time $t_{<MAP}$ occurring 0.4 seconds prior to time $t_{MAP}$ to a time $T_{>MAP}$ occurring 0.4 seconds after the time $t_{MAP}$.

6. The method according to claim 1, wherein said liquid sample is blood plasma.

7. The method according to claim 1, wherein the coagulant which is injected into the sample is thromboplastin with calcium ion.

8. The method according to claim 1, wherein the analog electrical voltage signal is developed by transmitting a light beam through a plasma sample and sensing the variations in light passing therethrough to develop corresponding variations in the electrical signal produced.

9. An apparatus for determining an anticoagulant therapy factor, said apparatus having a processor, and a computer chip preprogrammed with a set of instructions for cooperating with the output of a photodetection device which provides electrical data to said processor as a function of the optical density for a sample being analyzed, said apparatus having input means and storage means for storing data, said set of instructions including instructions for determining one or more anticoagulant therapy factors based on the steps set forth in claim 1.

10. An apparatus for determining a new anticoagulant therapy factor (nATF) comprising:
a. means including a light source, a test tube, a photocell, a battery, and a variable resistor all for developing an analog electric voltage signal having an amplitude proportional to an optical density of a liquid sample containing fibrinogen;
b. means including an A/D converter and a computer both cooperating for converting and recording the developed analog signal into a series of digital voltage signal values;
c. means for injecting a coagulant into a liquid sample, thereby producing an abrupt change in the optical density of the liquid sample, said abrupt change producing a change in the amplitude of the electrical analog signals, which, in turn, produces an abrupt change in the value of said digital voltage signals, the value of said digital voltage signals being directly indicative of fibrinogen concentration in the liquid sample;
d. means for recording an instant time to of said abrupt change in said value of said digital voltage signal;
e. means, including a computer, for monitoring said voltage digital signal values for a first predetermined fibrinogen concentration quantity C1;
f. means for recording an instant time t1 and the value of the voltage digital signal of said predetermined fibrinogen concentration quantity c~;
g. means, including a computer, for monitoring said voltage digital signal values for further fibrinogen concentration quantities;
h. means for recording an instant time tMAP and the value of the voltage digital signal of said predetermined fibrinogen concentration quantity CMAp~wherein tMAP corresponds with the point where the maximum acceleration of the conversion of fibrinogen to fibrin occurs;
i. means for recording an elapsed time between to and tMAP which defines a time to maximum acceleration of the conversion of fibrinogen to fibrin from coagulant injection in step (c);
j. means, including said computer, for monitoring for a differential change in the voltage digital signal values that include a predetermined fibrinogen concentration quantity CMAP;
k. said fibrinogen concentration quantity CMAP and said time tMAP defining a maximum acceleration point (MAP) and a time to maximum acceleration of the conversion of fibrinogen to fibrin from coagulant injection (TX), wherein TX is measured as the elapsed time from the time of the coagulant injection to to the time to maximum acceleration tMap, and each of the quantity CMap and said time tMap having a predetermined range starting prior to, at a time t<Map, and ending after said maximum acceleration point (MAP), at a time t>Map;

l. means, including said computer, for monitoring voltage voltage digital signal values at times t<map and t>Map, for respective predetermined fibrinogen concentration quantities CMAP, and for calculating the difference between quantities CMap to provide a first differential (IUX);

m. means, including said computer, for monitoring voltage digital signal values at times tEOT, wherein time tEOT defines a fibrinogen end point corresponding with the substantially complete conversion of fibrinogen to fibrin, and recording at an instant time tEOT the value of the voltage digital signal of a predetermined fibrinogen concentration quantity CEOT, and for calculating the difference between quantities c1 and CEOT to provide a second differential (IUT);

n. means, including said computer, for dividing the first differential (IUX) by the second differential (IUT) to define a percentage of the total voltage digital signal value change covered by an overall range defining a new fibrinogen transformation rate (nFTR), where nFTR=IUX/IUT and;

o. means, including said computer, for dividing the time to maximum acceleration of the conversion of fibrinogen to fibrin from the coagulant injection (TX) by a mean normal TX value of a sample of presumed normal patients to provide a maximum acceleration ratio (XR) which is factored to the (2−nFTR) power with the product thereof being the new anticoagulant therapy factor (nATF) expressed by the following relationship: nATF=XR(2−nFTR).

11. The apparatus according to claim 10, wherein said liquid sample is blood plasma.

12. The apparatus according to claim 10, wherein said coagulant which is injected into the sample is thromboplastin with calcium ion.

13. The apparatus according to claim 10, wherein the analog electrical voltage signal is developed by transmitting a light beam through a plasma sample and sensing the variations in light passing therethrough to develop corresponding variations in the electrical signal produced.

14. The apparatus of claim 10, further comprising an article for deriving said new anticoagulant therapy factor (nATF), the article including storage media with stored instructions which can be read and processed with a processor to determine said new ATF value for a sample.

15. A method of determining a new anticoagulant therapy factor (nATFz) comprising the steps of a. developing a series of analog electrical voltage signals having voltage amplitudes proportional to an optical density of a liquid sample containing fibrinogen;

b. converting the developed analog voltage signals into a series of digital voltage value signals;

c. adding a coagulant into the liquid sample, thereby producing an abrupt change in the optical density of the liquid sample, said abrupt change producing an abrupt change in the amplitude of the electrical analog signals which, in turn, produces an abrupt change in the value of said digital voltage signals, the value of said digital voltage signals being directly indicative of fibrinogen concentration in the liquid sample;

d. recording an instant time $T_0$ of said abrupt change in said value of said digital voltage signal;

e. monitoring said voltage digital signal values for coagulant activity;

f. recording an instant time $T_1$ corresponding to the start of clot formation;

g. monitoring said voltage digital signal values for further fibrinogen concentration quantities;

h. recording an instant time $T_2S$ which corresponds to a starting point of a simulated zero order kinetic and recording the value of the voltage digital signal of a fibrinogen concentration $C_{T2S}$;

i. recording an instant time $T_2$ and the value of the voltage digital signal of a predetermined fibrinogen concentration quantity $C_{T2}$, wherein $T_2$ corresponds with the point where the maximum acceleration of the conversion of fibrinogen to fibrin occurs;

j. recording an elapsed time between $T_0$ and $T_2$ which defines a time to maximum acceleration of the conversion of fibrinogen to fibrin (TX) from coagulant injection in step (c);

k. monitoring for a differential change in the voltage digital signal values that include said predetermined fibrinogen concentration quantity $C_{T2}$;

wherein said fibrinogen concentration quantity $C_{T2}$ and said time $T_2$ define a maximum acceleration point (MAP) and a time to maximum acceleration of the conversion of fibrinogen to fibrin from coagulant injection (TX), wherein TX is measured as the elapsed time from the time of the coagulant injection $T_0$ to the time to maximum acceleration $T_2$.

l. monitoring voltage digital signal values at times $T_2S$ and $T_2$ for respective predetermined fibrinogen concentration quantities $C_{T2S}$ and $C_{T2}$, with the difference between quantities $C_{T2S}$ and $C_{T2}$ being a first differential $IUX_z$;

m. monitoring voltage digital signal values at a time corresponding to the substantially complete conversion of fibrinogen to fibrin $T_3$ and recording at an instant time T3 the value of the voltage digital signal of a predetermined fibrinogen concentration quantity $C_{T3}$, with the difference between quantities $C_{T2}$ and $C_{T3}$ being a second differential $IUT_z$, the first differential $IUX_z$ being divided by the second differential $IUT_z$ to define a percentage of the total voltage digital signal value change covered by an overall range defining a new fibrinogen transformation rate (nFTR), where nFTR=$IUX_z/IUT_z$;

wherein a maximum acceleration ratio (XR) is determined by the time to maximum acceleration of the conversion of fibrinogen to fibrin from the coagulant injection (TX) divided by a mean normal TX value (MNTX) of a sample from patients with presumed normal coagulation;

wherein the new anticoagulant therapy factor ($nATF_z$) is expressed by the following relationship:

$$nATF = XR^{(2-nFTR)}$$

16. The method of claim 15, wherein the sample from patients with presumed normal coagulation is about 20 patients.

17. The method of claim 15, wherein the MNTX is the mean of the TX of a plurality of samples from at least twenty (20) people with presumed normal coagulation.

18. The method of claim 15, wherein the sample from patients with presumed normal coagulation is about equal to or greater than 20 patients.

19. The method of claim 15, wherein the values $T_2S$ and $T_2$ represent points along a simulated zero order kinetic line (L), with $T_{2S}$ corresponding to a time approximating the start of a simulated zero order kinetic, and with $T_2$ corresponding to the last highest delta absorbance value of a simulated zero order kinetic.

20. The method according to claim 15, wherein said liquid sample is blood plasma.

21. The method according to claim 15, wherein the coagulant which is injected into the sample is thromboplastin with calcium ion.

22. The method according to claim 15, wherein the analog electrical voltage signal is developed by transmitting a light beam through a plasma sample and sensing the variations in light passing therethrough to develop corresponding variations in the electrical signal produced.

23. An apparatus for determining an anticoagulant therapy factor, said apparatus having a processor, and a computer chip preprogrammed with a set of instructions for cooperating with the output of a photodetection device which provides electrical data to said processor as a function of the optical density for a sample being analyzed, said apparatus having input means and storage means for storing data, said set of instructions including instructions for determining one or more anticoagulant therapy factors based on the steps set forth in claim 15.

24. An apparatus for determining a new anticoagulant therapy factor (nATF) comprising:
   a. means including a light source, a test tube, a photocell, a battery, and a variable resistor all for developing an analog electric voltage signal having an amplitude proportional to an optical density of a liquid sample containing fibrinogen;
   b. means including an A/D converter and a computer both cooperating for converting and recording the developed analog signal into a series of digital voltage signal values;
   c. means for injecting a coagulant into said liquid sample, thereby producing an abrupt change in the optical density of the liquid sample, said abrupt change producing a change in the amplitude of the electrical analog signals, which, in turn, produces an abrupt change in the value of said digital voltage signals, the value of said digital voltage signals being directly indicative of fibrinogen concentration in the liquid sample;
   d. means for recording an instant time $T_0$ of said abrupt change in said value of said digital voltage signal;
   e. means, including a computer, for monitoring said voltage digital signal values for coagulant activity;
   f. means for recording an instant time $T_1$ corresponding to the start of clot formation;
   g. means, including a computer, for monitoring said voltage digital signal values for further fibrinogen concentration quantities;
   h. means for recording an instant time $T_{2S}$ which corresponds to a starting point of a simulated zero order kinetic of fibrinogen to fibrin conversion, and recording the value of the voltage digital signal of a fibrinogen concentration $C_{T2S}$.
   i. means for recording an instant time $T_2$ and the value of the voltage digital signal of a predetermined fibrinogen concentration quantity $C_{T2}$, wherein $T_2$ corresponds with the point where the maximum acceleration of the conversion of fibrinogen to fibrin occurs.
   j. means for recording an elapsed time between $T_0$ and $T_2$ which defines a time to maximum acceleration of the conversion of fibrinogen to fibrin from coagulant injection (TX) in step (c);
   k. means, including said computer, for monitoring for a differential change in the voltage digital signal values that include a predetermined fibrinogen concentration quantity $C_{T2}$;
   wherein said fibrinogen concentration quantity $C_{T2}$ and said time $T_2$ define a maximum acceleration point (MAP) and a time to maximum acceleration of the conversion of fibrinogen to fibrin from coagulant injection (TX), wherein TX is measured as the elapsed time from the time of the coagulant injection $T_0$ to the time to maximum acceleration $T_2$;
   l. means, including said computer, for monitoring voltage digital signal values at times $T_2S$ and $T_2$ for respective predetermined fibrinogen concentration quantities $C_{T2S}$ and $C_{T2}$, and for calculating the difference between quantities $C_{T2S}$ and $T_2$ to provide a first differential ($IUX_z$)
   m. means, including said computer, for monitoring voltage digital signal values at a time T3 corresponding to the substantially complete conversion of fibrinogen to fibrin and recording at an instant time T3 the value of the voltage digital signal of a predetermined fibrinogen concentration quantity $C_{T3}$, and for calculating the difference between quantities $C_{T2S}$ and $C_{T3}$ to provide a second differential ($IUT_z$);
   n. means, including said computer, for dividing the first differential ($IUX_z$) by the second differential ($IUT_z$) to define a percentage of the total voltage digital signal value change covered by an overall range defining a new fibrinogen transformation rate (nFTR), where $nFTR = IUX_z/IUT_z$; and
   o. means, including said computer, for dividing the time to maximum acceleration of the conversion of fibrinogen to fibrin from the coagulant injection (TX) by a mean normal TX value of a sample from patients with presumed normal coagulation to provide a maximum acceleration ratio (XR) which is factored to the (2−nFTR) power with the product thereof being the new anticoagulant therapy factor (nATF) expressed by the following relationship:

$$nATF = XR^{(2-nFTR)}.$$

25. The apparatus according to claim 24, wherein said liquid sample is blood plasma.

26. The apparatus according to claim 24, wherein said coagulant which is injected into the sample is thromboplastin with calcium ion.

27. The apparatus according to claim 24, wherein the analog electrical voltage signal is developed by transmitting a light beam through a plasma sample and sensing the variations in light passing therethrough to develop corresponding variations in the electrical signal produced.

28. The apparatus of claim 24, further comprising an article for deriving said new anticoagulant therapy factor (nATF), the article including storage media with stored instructions which can be read and processed with a processor to determine said nATF value for a sample.

29. A method of determining a new anticoagulant therapy factor (nATF) comprising the steps of:
   a. determining for a sample of a bodily fluid the start time represented by ($T_2S$) of a zero order kinetic rate of conversion of fibrinogen to fibrin for a reaction of a reagent which reacts with fibrinogen present in the body fluid sample to convert the fibrinogen to fibrin, and a unit absorbance value of said sample corresponding to the start time ($T_2S$);

b. determining the time to maximum acceleration (Tmap) for the rate of conversion of fibrinogen to fibrin for the body fluid sample;

c. determining a first differential (IUX) based on unit absorbance values obtained between the start ($T_2S$) of the zero order kinetic rate and the time to maximum acceleration (Tmap);

d. determining a second differential (IUT) based on unit absorbance values obtained between a theoretical end of test (TEOT) for the zero order kinetic rate corresponding to the substantially complete conversion of fibrinogen to fibrin, and the start ($T_2S$);

e. determining a first value V1 based on a ratio of IUT and IUX;

f. determining a value V2 based on a fractional portion of the start time ($T_2S$); and g. determining a new anticoagulant therapy factor (nATF) value by taking the product of V1 and V2.

30. The method of claim 29, wherein the value V1 is the theoretical end of test (TEOT), and is determined by the value of the ratio IUT/IUX being scaled with a multiplier time value (ZTM), with the value TEOT being obtained by the expression TEOT=ZTM/IUX*IUT.

31. The method of claim 29, wherein the fractional portion of the start time ($T_2S$) is a fraction based on the log base, where e=2.71828.

32. The method of claim 31, wherein the fraction based on the log base e is scaled to provide a range in the single digit ones place values.

33. The method of claim 29, wherein the value V2 is determined by a fraction of the start time according to the formula T2S divided by the product of 100 times the log base e, or $T_2S/(100*\log$ base e, where e=2.71828.

34. The method of claim 29, wherein a first unit value UV1 is the unit absorbance value of the sample at the corresponding time $T_2S$, and wherein a second unit value UV2 is the unit absorbance value of the sample at the corresponding time Tmap.

35. The method of claim 29, wherein a first unit value UV1 is the unit absorbance value of the sample at the corresponding time TEOT, and wherein a second unit value UV2 is the unit absorbance value of the sample at the corresponding time ($T_2S$).

36. The method of claim 29, wherein the time that said reagent is added to said body fluid sample is represented by the time T1, and wherein the value V1 is the theoretical end of test (TEOT), and is determined by the value of the ratio IUT/IUX being scaled with a multiplier time value (ZTM), with the value TEOT being obtained by the expression TEOT=ZTM/IUX*(IUT−IUL), wherein IUL represents the unit absorbance value of the sample measured between time T1 and time $T_2S$.

37. The method of claim 36, wherein the fractional portion of the start time ($T_2S$) is a fraction based on the log base, where e=2.71828.

38. The method of claim 35, wherein the fraction based on the log base (e) is scaled to provide a range in the single digit ones place values.

39. The method of claim 36, wherein the value V2 is determined by a fraction of the start time according to the formula T2S divided by the product of 100 times the log base e, or $T_2S/(100*\log$ base e, where e=2.71828.

40. The method of claim 36, wherein a first unit value UV1 is the unit absorbance value of the sample at the corresponding time $T_2S$, and wherein a second unit value UV2 is the unit absorbance value of the sample at the corresponding time Tmap.

41. The method of claim 36, wherein a first unit value UV1 is the unit absorbance value of the sample at the corresponding time TEOT, and wherein a second unit value UV2 is the unit absorbance value of the sample at the corresponding time ($T_2S$).

42. An apparatus for determining an anticoagulant therapy factor, said apparatus having a processor, and a computer chip preprogrammed with a set of instructions for cooperating with the output of a photodetection device which provides electrical data to said processor as a function of the optical density for a sample being analyzed, said apparatus having input means and storage means for storing data, said set of instructions including instructions for determining one or more anticoagulant therapy factors based on the steps set forth in claim 29.

43. An apparatus for determining a new anticoagulant therapy factor (nATF) comprising:

a. means including a light source, a test tube, a photocell, a battery, and a variable resistor all for developing an analog electric voltage signal having an amplitude proportional to an optical density of a liquid sample containing fibrinogen;

b. means including an A/D converter and a computer both cooperating for converting and recording the developed analog signal into a series of digital voltage signal values;

c. means for injecting a coagulant into said liquid sample, thereby producing an abrupt change in the optical density of the liquid sample, said abrupt change producing a change in the amplitude of the electrical analog signals, which, in turn, produces an abrupt change in the value of said digital voltage signals, the value of said digital voltage signals being directly indicative of fibrinogen concentration in the liquid sample;

d. means, including a computer, for monitoring said voltage digital signal values for coagulant activity;

e. means for recording an instant time ($T_2S$), which corresponds to the start of a zero order kinetic rate of conversion of fibrinogen to fibrin for a reaction of a reagent which reacts with fibrinogen present in the liquid sample to convert the fibrinogen to fibrin, and a unit value corresponding to the start time ($T_2S$);

f. means for recording a time to maximum acceleration (Tmap) for the rate of conversion of fibrinogen to fibrin for the liquid sample;

g. means, including said computer, for monitoring voltage digital signal values at times $T_2S$ and the time to maximum acceleration (Tmap) for respective predetermined fibrinogen concentration quantities $C_{T2S}$ and $C_{Tmap}$, and for calculating the difference between quantities $C_{T2S}$ and $C_{TMAP}$ to provide a first differential ($IUX_t$);

h. means, including said computer, for monitoring voltage digital signal values at times $T_2S$ and a theoretical end of test TEOT for respective predetermined fibrinogen concentration quantities $C_{T2S}$ and $C_{TEOT}$, and for calculating the difference between quantities $C_{T2S}$ and $C_{TEOT}$ to provide a second differential ($IUT_t$), wherein the theoretical end of test $T_{EOT}$ for the zero order kinetic corresponds to the substantially complete conversion of fibrinogen to fibrin;

i. means, including said computer, for determining a first value V1 based on a ratio of $IUT_t$ and $IUX_t$;
j. means, including said computer, for determining a value V2 based on a fractional portion of the start time ($T_2S$); and
k. means, including said computer, for taking the product of V1 and V2, with the product thereof being the new anticoagulant therapy factor (nATF) expressed by the following relationship:

$nATF = V1 * V2.$

44. The apparatus of claim 43, wherein said liquid sample is a body fluid sample.

45. The apparatus of claim 43, further comprising an article for deriving said new anticoagulant therapy factor (nATF), the article including storage media with stored instructions which can be read and processed with a processor to determine said nATF value for a sample.

* * * * *